(12) United States Patent
Zimmerman et al.

(10) Patent No.: US 8,307,785 B2
(45) Date of Patent: Nov. 13, 2012

(54) METHOD AND SYSTEM FOR MONITORING AND REDUCING RUMINANT METHANE PRODUCTION

(75) Inventors: Patrick R. Zimmerman, Rapid City, SD (US); Robert Scott Zimmerman, Rapid City, SD (US)

(73) Assignee: C-Lock, Inc., Rapid City, SD (US)

( * ) Notice: Subject to any disclaimer, the term of this patent is extended or adjusted under 35 U.S.C. 154(b) by 40 days.

(21) Appl. No.: 13/087,051

(22) Filed: Apr. 14, 2011

(65) Prior Publication Data

US 2011/0192213 A1    Aug. 11, 2011

Related U.S. Application Data

(63) Continuation-in-part of application No. 12/469,882, filed on May 21, 2009, now Pat. No. 7,966,971.

(60) Provisional application No. 61/342,644, filed on Apr. 16, 2010, provisional application No. 61/401,466, filed on Aug. 13, 2010, provisional application No. 61/055,933, filed on May 23, 2008, provisional application No. 61/209,179, filed on Mar. 4, 2009.

(51) Int. Cl.
*A01K 5/00*    (2006.01)
*A01K 29/00*   (2006.01)

(52) U.S. Cl. ..................... 119/51.02; 119/174

(58) Field of Classification Search ............ 119/51.02, 119/174, 417, 418, 421
See application file for complete search history.

(56) References Cited

U.S. PATENT DOCUMENTS

| | | | | |
|---|---|---|---|---|
| 4,830,010 A | * | 5/1989 | Marshall | 600/300 |
| 5,265,618 A | * | 11/1993 | Zimmerman | 600/531 |
| 6,270,462 B1 | * | 8/2001 | Mottram et al. | 600/529 |
| 6,488,635 B1 | * | 12/2002 | Mottram | 600/551 |
| 6,743,440 B1 | | 6/2004 | Ballinger, Jr. | |

(Continued)

FOREIGN PATENT DOCUMENTS

| | | |
|---|---|---|
| KR | 20060019062 A1 | 3/2006 |
| WO | 0126482 A1 | 4/2001 |

(Continued)

OTHER PUBLICATIONS

PCT International Search Report, International application No. PCT/US2009/044990; mailed Jan. 19, 2010.

(Continued)

*Primary Examiner* — Yvonne Abbott
(74) *Attorney, Agent, or Firm* — Kent A Lembke; Marsh Fischmann & Breyfogle, LLP

(57) ABSTRACT

A method and system for reducing methane emissions by ruminants. The method includes providing a feed dispenser for feeding ruminants nutrient supplements, and the feed dispenser includes a gas analyzer where a ruminant places its head. The method includes determining a particular ruminant has accessed the feed dispenser such as by reading an identifier from an RFID ear tag and operating the feed dispenser to provide a ration of methane-controlling nutrient supplement. The method includes using the gas analyzer to determine levels of carbon dioxide and methane and operating a data analyzing station to determine a ratio of methane to carbon dioxide and modify the type or amount of nutrient supplement for the ruminant for a next feeding to control methane production or achieve an animal production goal, such as by operating a hopper with supplement compartments. The unit can be monitored remotely and controlled through an Internet connection.

25 Claims, 15 Drawing Sheets

U.S. PATENT DOCUMENTS 7,350,481 B2 * 4/2008 Bar-Shalom .................. 119/859
2009/0285931 A1 11/2009 Shelby et al.

FOREIGN PATENT DOCUMENTS

WO 2004072801 A2 8/2004
WO 2009151927 A2 12/2009

OTHER PUBLICATIONS

International Search Report; PCTUS2011032531; date of mailing Dec. 20, 2011; Korean Intellectual Property Office; Applicant C-Lock Inc.

* cited by examiner

| DATE | COW 1 | COW 2 | COW 3 | COW 4 | COW 5 | COW 6 | COW 7 | COW 8 | COW 9 | COW 10 | COW 11 | COW 12 | COW 13 | COW 14 | AVG |
|---|---|---|---|---|---|---|---|---|---|---|---|---|---|---|---|
| DAY 1 | 0.79 | 0.67 | 0.76 | 0.60 | 0.64 | | 0.68 | 0.56 | 0.59 | 0.49 | 0.62 | 0.40 | 0.48 | 0.51 | 0.60 |
| DAY 3 | 0.86 | 0.86 | 0.86 | 0.88 | 0.82 | 0.53 | 0.93 | 0.64 | 0.70 | 0.67 | 0.71 | 0.59 | 0.50 | 0.45 | 0.71 |
| DAY 5 | 0.77 | 0.59 | 0.69 | 0.77 | 0.93 | 0.62 | 0.68 | 0.68 | 0.65 | 0.60 | 0.62 | 0.56 | 0.55 | 0.57 | 0.66 |
| DAY 7 | 0.72 | 0.83 | 0.72 | 0.69 | 0.73 | 0.61 | 0.73 | 0.68 | 0.60 | 0.61 | 0.69 | 0.57 | 0.40 | 0.47 | 0.65 |
| DAY 40 | 0.95 | 1.06 | 0.74 | 0.96 | 0.73 | 0.90 | 0.78 | 0.82 | 0.53 | 0.78 | 0.45 | 0.80 | 0.70 | 0.42 | 0.76 |
| DAY 42 | 0.87 | 0.87 | 0.75 | 0.80 | 0.87 | 0.70 | 0.82 | 0.78 | 0.78 | 0.67 | 0.90 | 0.68 | 0.63 | 0.57 | 0.76 |
| DAY 44 | 0.88 | 0.92 | 0.96 | 0.93 | 1.03 | 0.92 | 0.79 | 0.90 | 0.76 | 0.70 | 0.89 | 0.87 | 0.70 | 0.64 | 0.85 |
| DAY 46 | 0.91 | 1.02 | 0.90 | 0.81 | 0.78 | 0.88 | 0.89 | 0.93 | 0.92 | 0.76 | 0.95 | 0.70 | 0.65 | 0.82 | 0.85 |
| DAY 48 | 1.04 | 1.07 | 0.89 | 0.78 | 0.77 | 0.90 | 0.84 | 0.82 | 0.85 | 0.89 | 0.91 | 0.74 | 0.78 | 0.43 | 0.83 |
| DAY 50 | 0.95 | 0.92 | 0.85 | 0.80 | 0.94 | 0.80 | 0.81 | 0.82 | 0.78 | 0.82 | 0.96 | 0.80 | 0.69 | 0.65 | 0.83 |
| DAY 52 | 0.90 | 0.87 | 0.84 | 0.87 | 0.90 | 0.95 | 0.72 | 0.73 | 0.91 | 0.74 | 0.85 | 0.90 | 0.71 | 0.50 | 0.81 |
| DAY 54 | 1.01 | 0.98 | 1.07 | 0.91 | 0.74 | 1.15 | 0.81 | 0.86 | 0.79 | 1.00 | 0.95 | 0.81 | 0.75 | 0.52 | 0.88 |
| DAY 56 | 1.00 | 0.93 | 1.00 | 0.83 | 0.85 | 0.96 | 0.87 | 0.96 | 0.83 | 0.81 | 0.88 | 0.83 | 0.75 | 0.58 | 0.86 |
| AVG | 0.90 | 0.89 | 0.85 | 0.82 | 0.82 | 0.83 | 0.80 | 0.78 | 0.74 | 0.73 | 0.80 | 0.71 | 0.64 | 0.55 | 0.78 |

METHOD AND SYSTEM FOR MONITORING AND REDUCING RUMINANT METHANE PRODUCTION

CROSS-REFERENCE TO RELATED APPLICATIONS

This application claims the benefit of U.S. Provisional Application No. 61/342,644, filed on Apr. 16, 2010, and of U.S. Provisional Application No. 61/401,466, filed on Aug. 13, 2010, and the application is a continuation-in-part of U.S. patent application Ser. No. 12/469,882, filed May 21, 2009, which claims the benefit of U.S. Provisional Application No. 61/055,933 filed May 23, 2008 and of U.S. Provisional Application No. 61/209,179 filed Mar. 4, 2009, all of which are incorporated herein by reference in their entireties.

FIELD OF THE INVENTION

The present invention relates to methods of monitoring gaseous emissions of ruminants and of utilizing the information to reduce ruminant methane emissions, to increase ruminant production efficiency, and to monitor the health of individual animals.

BACKGROUND OF THE INVENTION

Carbon dioxide is a principal component of the metabolism of all vertebrate animals. Animals breath air. Oxygen in the air is captured in the lungs by hemoglobin in blood. Oxygenated blood is distributed to cells throughout the animal where it supplies key building-blocks to cells, and the oxygen is used to metabolize or "burn" carbon compounds, supplying energy required for cell processes. The carbon dioxide produced during this aerobic metabolism is then transported back to the lungs with deoxygenated blood and respired as carbon dioxide (and a few other gaseous waste products) in the animal's breath. In addition to lungs, ruminant animals have a digestive tract compartment called the rumen which harbors microbes that process grass in the absence of oxygen. This anaerobic fermentation produces large amounts of microbial protein. The end result is that ruminants are able to convert very low protein plant material into building blocks that are subsequently assimilated by the ruminant as the feed and microbial residue passes through the digestive tract.

Since the fermentation of forage material in the rumen is largely completed in the absence of oxygen, large amounts of methane and carbon dioxide are formed. These gases build-up in the rumen and create pressure that must be relieved. As a ruminant animal (such as a cow) exhales, the gaseous contents are forced from the rumen into the aesogophagus where it is exhaled (eructated—belched) preceeding an exhalation. These eructations or belches are not optional. For a well-fed animal they must occur approximately every forty seconds or the animal will bloat. Most of the gas produced in the rumen is eructated through the animal's nose. A small amount is dissolved in the blood and much of that is released through the lungs. The process is ecologically significant because it allows ruminant animals to utilize relatively-low-quality forage as food and to process it anaerobically, creating nutritious by-products and microbial protein that are used by the animal to produce high quality meat and milk. Ruminant gas fluxes are influenced by animal genetics, feed composition, consumption and behavior. As a result, changes in any of these parameters are likely to be quickly reflected in the fluxes of methane and carbon dioxide that are emitted in the course of the ruminant animal's breathing and eructations.

Routine measurements of ruminant methane and carbon dioxide emission fluxes and the fluxes of other metabolic gases, if possible and cost-effective, would provide very sensitive indicators to monitor and tune animal function. This would be much like using engine exhaust analysis to monitor performance and to tune fuel flow, combustion timing, and air mixtures to maintain optimal performance of a car engine. Changes in the fluxes of methane and carbon dioxide could inform management of optimal feed composition, the genetic feed efficiency of individual animals, and changes in animal health and behavior. In addition, methane emissions, although necessary, still represent a significant potential feed efficiency loss of roughly five to ten percent of the animal's gross energy intake. That equates to about one third to about one half a pound of lost potential weight gain per day. Therefore, changes in management that reduce methane fluxes can also potentially result in a net reduction of several dollars in feed costs per animal per day.

In modern, high-volume, low margin CAFOs (concentrated animal feeding operations), thousands of animals are housed and fed in very close quarters with a minimum labor force. Under these conditions, it is difficult or impossible to individually monitor the health of each animal. However, intensive observations and individualized monitoring can be economically important. For example, many diseases if not diagnosed and treated quickly can rapidly create epidemics within a confined herd. New equipment in modern dairies can be used to monitor milk production and other physical characteristics for each animal. However, by the time a problem is detected in the final products of an animal's metabolism, it is often too late to avert the loss of an individual or to prevent the spread of disease to others in the herd. Clearly, new technology is needed to effectively monitor each individual in large confined populations under crowded conditions.

Independent of disease monitoring, operator awareness of individual animal behavioral changes that are reflected in changes in grazing behaviour and animal activity can be economically important. For example, the research literature indicates that when an animal comes into heat (estrus) her grazing intake decreases and her general movement activity increases. These changes signal the optimal time for insemination of the animal to achieve pregnancy. These changes in behavior are thus also likely to be quickly reflected in methane fluxes and methane and carbon dioxide emission ratios. Similarly, changes in feed quality or composition that can occur when feed ingredients are modified or when cattle are moved to new pastures are likely to impact both the fluxes and the ratios of metabolic gas emissions.

In western feedlots, distiller's grain, which is a bi-product of methanol production from corn, is a preferred feed. However, ethanol plants often use sulfur-containing compounds to clean and disinfect plant facilities. Residue from these compounds can contaminate a distiller's grain. When feedlot cattle subsequently consume the grain, hydrogen sulfide is produced in the rumen. If not recognized immediately, the result often is the death of the animal. Routine monitoring of the animal's breath for hydrogen sulfide could, therefore, lead to early detection of contaminated feed and prevent large economic losses to the CAFO industry.

Individual monitoring to continually assess animal performance in rangelands can likewise be problematic. It is often difficult for producers and operators to assess the quality and quantity of available forage in pastures and to quantitatively determine changes in forage that occur as grazing progresses. The literature has documented that changes in forage quality are reflected in changes in methane and carbon dioxide fluxes from ruminants. Therefore, monitoring fluxes can potentially inform producers to maximize grazing effectiveness and to maintain sustainable productivity.

In rangelands, animals often are not easily approached and handled. In addition, grazing animals have evolved behavioral mechanisms to hide vulnerabilities from potential predators. Therefore, routine and comparative diagnostic observations of animals to assess health and performance are relatively difficult and expensive. Automated monitoring of metabolic gases could inform managers of changes in the health of individual animals. In some rangelands, toxic substances, such as some sulfur compounds, can accumulate in vegetation and water supplies. These substances can result in ruminant mortality. Hence, routine monitoring of specific metabolic gases, such as hydrogen sulfide, that are produced by an animal could alert producers to mitigate adverse impacts to the herd.

Methane is also a powerful greenhouse gas (GHG) with a GHG potential roughly 25 times that of carbon dioxide. Some scientists estimate that livestock contributes up to thirty-seven percent of the total global methane ($CH_4$) budget. Dairies and beef production operations are therefore identified as a very large global producer of GHGs, with the largest component of their emission footprint resulting from methane production in the rumens of animals. As a consequence, the global CAFO community has made a commitment to reduce the GHG impact resulting from the production of animal products such as meat and milk.

Methane emission from bovine sources, of which the majority is through belching, can be significantly reduced through modification of cattle diet and other management actions. Attempts at methane emission reduction typically involve using nutrient blocks or other feed supplements while other efforts have concentrated on modification of the genetic composition of the animal herd. To date, efforts to measure and potentially remediate this source of GHG from ruminants have not been considered feasible or widely implemented in part because of high costs related to monitoring $CH_4$ emission from ruminants in coordination or concurrently with measurement of supplement use.

Prior to the invention described herein, it has been impractical to actually monitor changes in animal GHG production that result from such efforts. The difficulties and expense of current technology, even for scientists involved in this research, has made it impractical and not cost-effective to make more than a few measurements over relatively short time periods for only a few animals and in only strictly controlled research settings. Therefore, since it is difficult to verify that mitigation plans actually result in decreased methane emissions to the atmosphere, few projects to generate carbon credits or greenhouse gas reduction credits for sale in voluntary markets have been attempted. Likewise, the development of GHG reduction programs for ruminant emissions in the regulated GHG markets of countries has also been inhibited because of the lack of suitable monitoring and verification techniques.

The loss of methane is a significant energy loss to the animal. Globally this is equivalent to trillions of dollars of lost dietary efficiency. Animal nutritionists know that the metabolic pathways in the rumen can be modified by diet to reduce methane production and to more efficiently process feed. Several dietary supplements are available, and, in many cases, the cost of the nutrient supplement is easily exceeded by the animal weight gains, making use of supplements attractive to ruminant producers such as the cattle industry. Accordingly, reduction in methane emissions by ruminants can help animals become more productive per unit of forage or feed while also reducing undesirable methane emissions. When animals eat low quality forage, it actually takes a longer time to pass through their gut. Hence, the poorer the quality of forage, the longer it takes the animals to digest the forage, and this results in lower weight gain but more methane production. However, since monitoring of changes in methane performance under actual field conditions has been difficult or impossible to achieve in the past, it is not practical to modify forage composition to minimize methane losses nor to monitor and modify genetic factors that influence ruminant methane production. A system that can monitor changes in relative methane emissions could therefore provide important information to ruminant producers concerning optimal forage and grazing conditions. In addition, since animals fed a highly energetic diet process that feed more quickly, they produce more methane per unit time, but much less methane per unit of production of meat or milk. Therefore, it can also be important to measure methane and carbon dioxide from the rumen as well as carbon dioxide from the animal's breath in order to differentiate rumen processes from catabolic and respiratory processes and to measure their emissions relative to measurements of animal production, such as animal weight gain and/or animal milk production.

U.S. Pat. No. 5,265,618 discloses a system that measures the flux of metabolic gas emissions from cattle or other animals. The system does not require that the animals be confined to a chamber or stall. An animal whose metabolic gas emissions are to be measured is first fed a permeation tube (i.e., a metal tube with a gas-permeable plastic disk in one end). Inside the tube is a tracer that is physiologically inert. The permeation tube is filled with pressurized liquid tracer, which slowly permeates in gaseous form through the plastic disk. In order to measure rumen-produced and respiratory metabolic gases, a sample container, such as an evacuated container or an inflatable collar, is placed on the animal. A small diameter sample tube is attached from the sample container to a halter and terminates somewhere near the animal's mouth. When the animal breathes, it exhales metabolic gases as well as the tracer. A sample of air containing both the metabolic gases and the tracer gas is then collected through the sample tube. Since the permeation rate of the tracer is known and constant, the ratio of the flux of a given metabolic gas to the flux of the tracer gas is equal to the ratio of the mixing ratios of the respective gases in the air sample that is collected. The rate of flux of metabolic gas from the animal's rumen is thus readily calculated by measuring the metabolic gas and tracer mixing ratios in the sample thus collected. This technique is not well-suited for accurate measurements of carbon dioxide fluxes since background concentrations are relatively high and variable. In addition, this technique is difficult to employ for metabolic gases such as hydrogen sulfide or oxygenated organic compounds that degrade during storage in sample containers. This system also requires substantial animal handling and training to be effective. Moreover, it is not practical for animals that do not tolerate a halter, which may include large percentages of a ruminant herd. Also, the system can only provide time-integrated values that represent average rumen catabolic and respiratory processes. The system cannot be used to track short-term changes nor can it isolate rumen processes from respiratory processes related to catabolism.

Schemes to convert increased ruminant metabolic efficiency into marketable GHG offsets have not been financially viable. Though mineral blocks, other effective nutrient supplements, and rumen-modifying antibiotics and ionophores are effective in reducing methane production and in many cases cost only a few cents per day, at the current value of greenhouse gas (GHG) offsets, compliance, documentation, and monitoring costs exceed the value of the GHG offsets that can be generated. Also, animals fed poor-quality forage have lower methane emission rates per unit time than animals fed high quality diets. However the emission of methane as a function of gross energy intake is much higher for an animal fed low quality forage compared to an animal fed a high quality diet. As a result methane per unit of animal production is much higher for low quality and poorly digested forages compared to animals fed a high quality digestible diet. Specific nutrients, missing from low quality forage can be supplemented through the use of nutrient feeders to boost digestibility, resulting in increased efficiency and lower methane emissions per unit of animal production. It can therefore be desirable to document relative changes in methane emission rates and it may not always be necessary to measure fluxes of methane per unit of time. That is changes in ratios of methane compared to carbon dioxide for respiration as well as for rumen gas per unit of production might provide the information required to document animal performance changes that lead to quantifiable methane reductions and can generate carbon credits. However, measurement of emissions of methane and carbon dioxide from the rumen and differentiation of this flux from measurements of carbon dioxide resulting from catabolism over shorter time periods are necessary in order to track energy flows through a specific ruminant and to document the efficiency of production of meat and milk in a way that facilitates interactive treatment to improve productive efficiency and lower methane emissions per unit of production.

SUMMARY OF THE INVENTION

One or more embodiments of the invention provide an implementation of an animal monitoring station that can measure methane emissions and/or emissions of carbon dioxide and/or other metabolic gases such as hydrogen and hydrogen sulfide. Changes in the ratios of methane compared to carbon dioxide may be used to indicate changes in metabolic efficiency, and these measured emission ratios and changes in metabolic efficiencies may then be tracked in some embodiments along with additional data which is subsequently stored for an individual animal and/or on a herd basis in the system's memory or data storage. Further, this data can be routed to a computer where numerical models or other calculations may be performed (e.g., with software programs or modules run by the computer) to transform the data into methane fluxes, fluxes of carbon dioxide, and fluxes of other metabolic gases that can be measured in the animal monitoring station. In addition, either an internal (e.g., from the animal) or an external (e.g., from an external source) tracer can be incorporated into the system. In this case, halters or other devices may not be required, and the animals may not require handling or confinement while methane and carbon dioxide and other metabolic gas fluxes are directly measured from each animal.

For example, in one exemplary but not limiting embodiment of the present invention, a ruminant's gaseous emissions are monitored, methane emissions are determined, and the ruminant's feed supply is adjusted or supplemented or the ruminant is otherwise treated to reduce methane emissions. In some embodiments, non-dispersive infrared instruments monitor carbon dioxide and methane emitted by a ruminant. Alternatively, methane and carbon dioxide and other metabolic gas emission measurements are obtained using methods such as solid-state sensors, tunable diode laser absorption spectroscopy (TDLAS), open-path Fourier transform infrared spectroscopy (FTIR), other infrared-based methods, miniaturized gas chromatography/flame ionization detection (GC/FID), proton transfer reactor mass spectroscopy, cavity ring-down spectroscopy, or other miniaturized mass spectrometry. In other cases, it can even be determined through the collection of periodic gas samples, either in containers or on solid or liquid substrates, subjected to later analysis using gas chromatography or using many other available analytical techniques.

The information thus obtained may be considered by software programs/modules run by one or more computers/processors in the system along with animal statistics available from a database stored in system memory or otherwise accessible (e.g., via wired or wireless connections to a digital communications network such as the Internet or an intranet or the like) and/or from information associated with an RFID tag attached to the ruminant, which may include heritage information, e.g., whether the animal is weaned, its age, its internal body temperature, its weight and other physiological parameters, animal genetic information, and the like (e.g., the RFID tag may have readable memory or may provide an identifier that can be used to retrieve this information from system, or otherwise available/accessible, data storage or memory). Alternative methods for identification of individual animals may include eye/retinal patterns, laser-imprinted bar codes or alphanumeric codes, facial pattern recognition, gases or chemical compounds emitted in the breath or from other parts of the animal. Based upon the emission information and the other information about the ruminant, one or more of the software programs or modules determines a supplement prescription or mix (e.g., particular supplements and amounts of each chosen supplement). The system may then be operated such that one of a plurality of supplements and/or a particular amount of a supplement or of a plurality of supplements is offered to the ruminant by operation of a feeding station (e.g., control signals transmitted by the controller/operator of the methane monitoring and reduction system to supplement/feed dispensing devices of the feeding station).

Alternatively, the animal information may be used to determine the frequency and/or the amount of a supplement feed or any "bait" to be supplied by the feeder in order to attract the animal, to identify the animal, and to entice it to place its mouth and nostrils in the proximity of the air intake of the feeder so that the animal's metabolic gas emissions can be qualitatively and/or quantitatively measured. Alternatively, the metabolic gas sampling system can be integrated into a watering unit, a mineral dispenser, a salt-lick, a supplement feeder, or a bait dispenser, so that the animal places its nose and mouth in a position to result in a measurement of methane, carbon dioxide, and/or other metabolic gases emitted from the animal.

In a method of an exemplary embodiment of the present invention, a ruminant presents itself at a feeding station at which carbon dioxide and methane emitted by the ruminant in its breath are measured. Other measurements may also be taken and routed into the data logger. These data can be provided by individual sensors and stored in a ruminant and methane monitoring database. In other cases, these data may be derived from signals read from the animal's RFID ear tag and read into the data logger. In some embodiments, at least one determination is made about the production of methane by the animal (e.g., by a methane monitoring module run by the computer/processor to determine methane emissions/production and/or to process methane and carbon dioxide emission ratios to determine a current metabolic efficiency for the animal). Additional determinations which may be made include the identification of one or more supplements or a mixture of supplements and an amount or amounts thereof to offer to the ruminant to reduce the determined methane emission which would be expected to subsequently occur should the ruminant's diet not be modified. The data collected at the animal measurement station can be stored in an internal data logger or it can be transmitted through a wired connection or via a wireless signal to a remote location for processing.

According to one aspect, a ruminant methane feed station may be constructed and instrumented to function in several modes. In one example, the feed station includes a hood to restrict the effects of the wind and/or to serve to concentrate the breath of the animal. In this case, an animal, such as a cow, would insert its head into an opening. As the animal approaches the monitoring station, a sensor may be used to read an ear tag (e.g., a tag including an RFID chip or tag) to determine the identity of the animal. Additional information could also be delivered such as the age and type of animal. Based on this information, a specific nutrient mix could be released by selective operation of feed dispensers at the feed station. In one useful embodiment, the mixture is designed to reduce the production of methane by the ruminant. The determinations controlling the type and amount of nutrient performed by software modules run by the computer(s) of the system may be based on input from sensors mounted inside the feed station and on the ground in proximity to the feed station. Information collected could include animal weight in order to determine animal weight gain, methane and carbon dioxide emission ratios while at/near the feed station to determine animal metabolic efficiency, and/or additional measurements as useful to document performance and to generate CERCs (Carbon Emission Reduction Credits).

In one example, the unit is designed to operate based on information gathered in the field. In other examples, the instrument can be programmed remotely and operated by a remote computer containing resident data or the animal monitoring unit can be operated remotely and manually by a human operator. In one example, the human can access the animal metabolic gas monitor and observe its operation via a remote video link and operate the unit remotely in one example accessing the specific unit via the Internet. The operator then can use specially designed software to monitor and control the animal monitoring unit. In one embodiment, the operator can use a smart-cell phone such as a DROID™ available from Motorola, a BLACKBERRY® available from Research In Motion Limited, or any enhanced capability cellphone as an operating interface. In another example, the operator can use a laptop computer or a standard office computer with an Internet connection to monitor and remotely operate the animal measurement system.

In another example, in addition to the measurement of methane and carbon dioxide ratios in the animal's breath, the insertion of the animal's head into a feed hood, stall, feed station, or watering station triggers the release of a specific, controlled flow-rate tracer. The tracer is preferably in some embodiments an inert gas such as sulfur hexafluoride, butane, propane, or other chemical compound that is measured with instrumentation installed in the feed station. The dilution of the tracer is used to correct methane and carbon dioxide measurements for the effects of atmospheric dilution. In this way, the flux of methane and carbon dioxide can be determined in addition to the metabolic methane and carbon dioxide ratios.

In another example or embodiment, the animal's breath is used as a tracer of atmospheric dilution. Because the breath of a ruminant is saturated with water, changes in water vapor measured by a specific sensor provided at the feed station are sometimes used to document mixing. Alternatively, mixing could be determined by monitoring other gases or compounds naturally occurring in ruminant breath such as low molecular weight alcohols and organic acids. From this information, absolute fluxes of methane could be measured/determined by software/hardware provided in an embodiment of the ruminant monitoring system. In another embodiment, diurnal cycles of rumination are captured by locking animals out of the feeder until specific times of the day. For example, an animal might typically approach the GreenFeed system or feeding station at a specific time of day. The system could be programmed/controlled so that no supplement was provided unless the animal approached at a different time. In this case, a visual or audio stimulus is sometimes provided by the GreenFeed system when it is "Live" to dispense the nutrient supplement (or attractant feed). The system is therefore programmed to capture ruminant processes at differing times throughout the diurnal cycle and therefore define/determine methane flux behavior. In another embodiment, the system is programmed so that specific individuals are dispensed supplements on alternate time-period schedules and only a placebo during other time periods. In this way, the changes in methane emissions associated with the application of a specific treatment are more unequivocally determined and stored in memory or in the monitoring/tracking database (e.g., documented).

In a further embodiment, a nutrient block system is provided to monitor methane and carbon dioxide concentrations of tidal breath as well as the eructation of ruminant animals while they are in a pasture. The feed station or system portion of the monitoring system looks similar to a hooded salt-lick mounted on a short post. The nutrient block may be surrounded on all but one side by a cover. The uncovered side has an opening large enough for an animal to insert its head and access a nutrient block or container(s) of one or more nutrients. Mounted under the hood is an RFID tag reader for activating and reading/receiving information about each animal from its RFID ear tag. The nutrient-block station may further include a methane/carbon dioxide monitor, a data logger, and/or a communication device (e.g., a Bluetooth transmitter, a cell phone with a modem, or the like). The station may in some cases contain a global positioning satellite (GPS) chip to obtain and collect information about location of the unit and the time of day that it was accessed by the animal. Again, this information may be stored by the datalogger at the feeding station or at a differing data storage device, such as a centralized datastore used to store a database collected from a plurality of such feeding stations and/or for a set of animals or a monitored herd of ruminants. In some cases, the system is powered by batteries recharged by solar cells, although other power sources may readily be used.

In one operating method for a methane monitoring and production control system, when an animal approaches the nutrient block station of an embodiment of the present invention, the system turns on for a specified time-period to monitor and document methane/carbon dioxide ratios, the animal's identification number (such as read from an RFID-based ear tag), the time (from a system clock at the feeding station), and/or the location of the station (from a feeding station identifier and look up, from a GPS chip, or the like). Based on information collected and obtained and based on determinations made based on the information by system software, a supplement is made available via selective operation of feed dispensers at the feeding station to the animal to control, reduce, or maintain methane emissions at a presently desired level (e.g., a goal methane emission level may be stored in system memory for each animal in a monitored herd and the system may compare a currently determined emission rate with the goal level to determine whether one or more supplements should be provided and in what amounts to increase, decrease, or maintain methane emission levels for the feeding animal). In some cases, it is likely the animals will consume one to two ounces of supplement per day, and the amount of supplement consumed per animal may be controlled by modifying the salt content of the supplement (e.g., not only prescribing/controlling supplements and their amounts but also controlling additives provided with such a supplement mix to encourage the supplement(s) to be consumed).

In another operating method for the methane monitoring and production control system, methane measurements obtained when the animal is visiting the animal monitoring unit are compared with archived methane and metabolic gas emissions for this specific animal. If the currently-measured fluxes fall outside of prescribed limits, a data flag is produced and a message is sent to the producer/manager notifying him or her that the animal is not functioning normally. In another operating method, when the process described above takes place, the animal is tagged with a visual or an electronic tag. For example, the animal monitoring unit may be coupled to a container that dispenses paint. When an animal's metabolic gas fluxes or its composition falls outside of specified boundary, the paint unit dispenses paint so that the specific animal is readily identified for closer examination by workers.

In another operating method for the animal metabolic gas monitoring system, measurements for an individual animal may indicate an increase in carbon dioxide emissions with or without a corresponding decrease in methane emissions. If the changes in the ratios of metabolic gas components and or the changes in the fluxes of the metabolic gas components fall outside of specified limits for this animal, an alert is sent and or the animal is marked to indicate to managers that the animal is in heat (or estrus) and that the optimal time for breeding is near.

In yet another method of operating the animal monitoring unit, the data for each individual animal is combined to determine trend data for the entire herd. If, for example, data indicates that methane and carbon dioxide are decreasing for the herd in spite of a consistent diet, then the data may alert a manager that key nutrients may be missing thus decreasing forage utilization despite a constant feed source. Alternatively, long term trends for monitored metabolic gases that change for the entire herd can be used to document changes in efficiency that lead to decreased methane emissions and, potentially, to the generation of carbon emission reduction credits.

In another method of operating the animal monitoring unit, the data for each individual animal is compared to her historical data and/or to the herd average date. If, for example, the animal's methane production drops below specified limits for a specified number of monitoring periods, the animal is flagged for closer examination. For example, these changes could signal the early onset of mastitis.

In another method of operation, the data from the animal monitoring unit can be combined with data from other independent sensors, and the data is processed to identify and advise operators and managers. For example, the animal monitoring unit could contain a floor-mat within an alley leading up to the unit. If pressure sensors detect a change in the animal weight distribution coupled with a change (likely a decrease) in rumen methane and carbon dioxide and (possibly an increase) in respiratory carbon dioxide, the animal is marked and the operators are notified that closer inspection for lameness is warranted.

In another example, the animal monitoring unit can be deployed in a feedlot. Sensors can include a solid-state sensor or other sensor to monitor hydrogen sulfide in the animal's breath. If specific fluxes of hydrogen sulfide are detected, the operators will be immediately alerted, for example, through a cell phone that the feed might contain dangerous levels of sulfur-containing compounds and the feeding regime must be immediately changed.

In practice, the station may be placed strategically in a field near a point of congregation such as a water source with a typical feeding station serving a relatively large number of animals such as a station serving 40 to 100 animals. The system may be loaded with a placebo mineral block to document the baseline methane emissions for the herd and the pasture. In this way, the mineral supplement may be added to document GHG reductions, so that each animal, as well as the whole herd, may be monitored in a very cost-effective way. If exact or more accurate emission rates of methane and carbon dioxide are found useful (e.g., instead of relative changes in metabolic efficiency), an optional tracer release system can be incorporated into the system. The tracer release system utilizes a third chemical species (e.g., butane, propane, or an inert fluorocarbon that would be emitted at a defined rate). The dilution of the tracer is then utilized to correct for limited atmospheric mixing that may occur when the animal's head is "under the hood." This may not be used in some implementations, though, since concentrations of methane and carbon dioxide under the hood will likely be many times greater than ambient concentrations and efficiency gains can be documented with the ratio of the two gases without the absolute emission rate.

In one preferred implementation of the tracer technique, a solenoid valve is activated by an operator or remotely through an automated program. The tracer release system incorporates a flow-control system so that the flow rate from the tracer reservoir remains constant. Tracer gas is directed to be released near the mouth and nose of the animals when they are in the correct position for accurate measurements. At a set interval, the tracer flow is switched to a release point inside the air-collection pipe that collects animal mouth and nose emissions. Because the flow rate is constant, differences in the ratios of the tracer concentration values determine the metabolic gas capture efficiency. This capture efficiency is used to convert the metabolic gas concentration data into mass flux data. In this example it is not required that the exact flux of the tracer is known as long as it is constant. If, however, the mass flux of the tracer is determined through periodic weighing of the tracer reservoir or other methods, the data can be used to independently assess the flow rate through the system and/or changes in instrument calibration. If a tracer is used that is detected by one of the sensors (such as the NDIR methane sensor), then the tracer flow release can be controlled to determine mass flow rate and to determine changes in the calibration of the methane sensor.

In addition to the generation of high value GHG offsets, the system may serve as a livestock management tool. The methane/carbon dioxide ratios obtained provide valuable information about the condition of the animal and of the pasture. Methane and carbon dioxide mass fluxes can be used along with numerical models to estimate dry-matter intake, digestibility, and animal efficiency. This data can be used along with production data to select breeding stock that produces more meat and milk on less feed resulting in lower emissions of greenhouse gases and improved animal welfare and global sustainability.

Concentrations under the hood of the animal monitoring system when an animal is present are normally fairly high, i.e., much above ambient, so that measurements of metabolic gas concentrations are facilitated. This allows an embodiment of the system to employ OEM NDIR instruments. Although the cost of this type of sensor can reach several thousand U.S. dollars, the GreenFeed station or feeding station will still be cost effective. The fast, sensitive, and automated detection of animal behavior, animal efficiency, and animal health is likely to improve animal welfare, decrease animal loses, improve animal genetics for increased efficiency and improve the economic sustainability of the operation. Since the station is automated, the monitoring costs per animal will be quite low. Because one station can be shared among many cattle or other herd animals, the cost per animal is also relatively low.

With a GreenFeed feeder, the cow's head only needs to be near the plenum to measure fluxes. It does not have to be in a specific location, and free movement is allowed and it is still possible to measure mass fluxes. The feeder is relatively open to the atmosphere compared to past designs. Numerous intake holes are used in a plenum to capture breath as the cow's head moves around. The animal is not required to put their nose in a small restricted area where the intake somehow aligns with their nose. The airflow through the GreenFeed feeder is much larger than what is emitted from the cow (about 8 to 10 times (or more) higher). A powered fan is used to induce this air flow over the food tray or through the feeder hood/manger in the absence of the animal (for background measurements) or about the animal when one is present (for breath measurements).

Significantly, the GreenFeed system is configured to measure the background gas concentrations and gas concentrations from the animal to determine the increase in concentrations. In this manner, mass fluxes from the animal can be calculated at the GreenFeed station or a remote data analyzing station/server by using the increase in concentrations and the total airflow through the system. In this regard, total airflow through the collection pipe is measured, which includes the animal's breath. Because the animal's breath only makes-up a small part of the total flow, the GreenFeed system is not configured to directly measure the gas flow from the animal. Instead, gas mass fluxes from the animal are determined by using the concentration sensors along with the pipe airflow sensor and by applying values from the tracer measurements to the measurement in the presence of the ruminant. Specifically, because the system is more open, a tracer system can be readily and effectively used to quantify the capture rates of the cow's breath into the collection pipe. This allows mass (or volume) fluxes to be accurately determined even if all of the breath is not captured.

An infrared or ultrasonic head sensor is used to measure distance of the animal's nose from the intake. Later, the data can be sorted to determine when the animals head was in the feeder and how far it was from the intake. In practice, the GreenFeed feeder's measurement and flow system is active most of the time, even when a cow is not present (except when the system is conserving batteries). This allows the data analyzing software to determine background concentrations of gases without the cow, so that mass (or volume) fluxes can be determined when a cow is present by taking the difference between the measurement without the cow and the increase when the cow is visiting the feeder. In many applications, food is used to just get the animal to the feeder, but the feeder is relatively open with the animal coming to the feeder in a voluntary way and without any handling by an operator (or restrictions on where the animal's head is held during emission measurements).

In one particular embodiment, a method is provided for managing methane emissions from a ruminant. The method includes providing a mechanism for dispensing feed to a ruminant into a food tray, and then first measuring carbon dioxide and methane in air proximate to the food tray to determine a background gas level. The method continues with sensing a ruminant proximate to the food tray in the feed dispensing mechanism and, in response to the sensing of the ruminant, second measuring carbon dioxide and methane in air proximate to the food tray. The method then further includes, with a data analyzing station, processing the first and second measured carbon dioxide and methane concentrations to determine an increase in carbon dioxide and methane concentration. Then, with the data analyzing station, the method includes determining carbon dioxide and methane fluxes for the ruminant based on a total airflow and on the determined increase in the carbon dioxide and methane. In some cases, the method may include operating the data analyzing station to determine, based on the determined carbon dioxide and methane fluxes, a supplement to be presented in feed dispensed by the dispensing feed mechanism to the ruminant to control methane emitted by the ruminant.

In some embodiments, the feed dispensing mechanism includes a gas collection pipe with an inlet adjacent the food tray, a fan moving air over the food tray into the gas collection pipe, and an airflow sensor measuring air flow in the collection pipe to determine the total airflow when the ruminant is sensed to be in the feed dispensing mechanism. In such embodiments, the method may include operating a tracer system to discharge a quantity of a tracer in the feed dispensing mechanism, sensing a concentration of the discharged tracer in the gas collection pipe, and, with the data analyzing station, quantifying a capture rate for breath emitted by the ruminant during the second measuring step and applying the capture rate to the determined mass fluxes to generate capture rate-adjusted fluxes for the ruminant.

The gas collection pipe may include a flow distributor providing a mixing of the air flow drawn into the gas collection pipe across the gas collection pipe, whereby mixing of the air flow is provided across a flow path with minimal mixing along the flow path in the gas collection pipe. Further, an inlet plenum to the gas collection pipe inlet may be positioned in the feed dispensing mechanism to extend upward from at least two sides of the food tray, and the inlet plenum may include a plurality of inlet holes for directing ruminant breath and air into the gas collection pipe inlet. The method may further include differentiating emissions of methane and carbon dioxide by the ruminant during eructations from emissions of methane and carbon dioxide in tidal air of the ruminant. In practice, the total air flow may be at least about 8 to 10 times greater than breath emitted from the ruminant. Further, the step of sensing the presence of the ruminant may involve operating an infrared or ultrasonic head sensor to determine a position of the ruminant's head relative to the food tray including a distance of a portion of the ruminant's head to the head sensor.

There are a number of features of the GreenFeed system that make it unique and useful for many applications ranging from dairy tie-stalls, milking robots, and pastures/rangeland settings. The system uses a wedge-shaped polyethylene feeder shell, which may be pivotal in wind to have its opening (for receiving the animal's head or at least nose and mouth) facing away the direction of the wind to limit mixing (e.g., if the wind is from the north, the opening would rotate to face south). The body of the shell may be adapted to receive special "wings" that are inserted on each side of the shell using spacers of the appropriate size so that it can be customized easily to fit specific sizes of animal. For example New Zealand dairy cows are typically 30 percent smaller than United States Holsteins. In a system designed for New Zealand, wider spacers and a lower angle for the shell on its pivotal mounting would be used so that when the animal approaches, mixing is somewhat restricted.

The feeder utilizes an opening that is designed to keep rain out but to let in light. At the top of the unit, a Lexan™ or other clear to translucent window may be provided because cows do not like to enter or to put their heads into dark places. The feeder/manger may utilize both light and sound to indicate to an animal whether or not it is eligible to be measured/fed (e.g., perform RFID-based identification of a cow and determine whether it is due for feeding/emission monitoring). Over the long run, it is believed that this will keep animals that are not due to be measured from blocking the entrance for others.

The system may use measured, dynamic air-flow to sweep metabolic gases through the system and to mix them across the flow path but to minimize mixing along the flow path. This allows second-by-second resolution of data so that methane, carbon dioxide, and other metabolic can be monitored and gases from tidal air (lungs) can be readily differentiated from gases that originate in the rumen (eructations). This provides important information about lung function, rumen function, metabolism, and anaerobic fermentation processes, and such differentiation provides very important diagnostic information (such as when a cow may be ready for breeding, when a ruminant is ill and should be treated, when a dietary change such dry matter intake or pasture quality has changed, and so on).

The GreenFeed system may monitor ratios of key gases, but, significantly, many embodiments of the GreenFeed system are also configured to perform quantitative measurements of fluxes of the metabolic gases of interest. Flux is defined as the mass (or volume) of a compound, such as methane, emitted per unit time. The reason the system is able to monitor flux is because it acts to monitor key variables that define the flow-rate and the capture rate as well as the ambient conditions and the animal's position with independent sensors. Further, the GreenFeed system is adapted to constrain the mass flow through the system by periodically releasing a repeatable quantity of a tracer. The tracer (e.g., propane) can also be used as a surrogate to independently verify calibration of methane sensors.

In some cases, the system can operate autonomously outdoors using solar power and indoors using batteries. Batteries can be effectively recharged by many sources of low-quality power. It is often a problem to obtain high-quality consistent power in a rural area or in a dairy, where large fans and other equipment periodically cycles and creates voltage drops and surges. High-resolution data may be stored within the unit and periodically transmitted to centrally-located computers where resident programs process the data to produce results and reports relevant to specific operators. Reports provided to a worker could include a simple alert to take a close look at a specific animal (such as for health or breeding reasons). Reports to the dairy or feedlot nutrition manager could highlight trends in dry-matter intake, digestibility, efficiency, breeding, and the like. Reports to the farm operator might identify animals with key performance characteristics.

One difference between GreenFeed systems and methods and anything ever done before is that they are highly automated and animals require little or no training to voluntarily use the system. Further, the GreenFeed systems and methods are quantitative. The resolution of the data provides second-by-second resolution so that rumen metabolism can be differentiated from aerobic metabolism. The system is redundant, and flow rates are monitored directly. Flow rates can be calculated independently from internal tracers (carbon dioxide and water vapor for example) and/or external tracers (propane). Propane releases can also serve as a surrogate for methane in the NDIR methane sensor so that calibration can be tracked and measurement problems can be quickly identified. The tracer release can be qualitative as long as it is constant the release inside the sampling pipe and near the animal's mouth and nose provides the capture ratio. The tracer release can also be quantitative, as the system may be operated to periodically weigh the tracer container to determine tracer loss. Additionally, the system may operate to monitor the times when the tracer is released, such that its software processes can accurately calculate the average of the tracer mass loss per unit time (i.e., the tracer release). The system and/or a suite of systems can be operated remotely either through wired connections or through wireless connections. The system may utilize an Internet or other network interface. The system is designed to be intuitive so that results can be quickly visually interpreted and key operating parameters can be manipulated by relatively untrained operators.

The system is typically designed to operate an auxiliary sample system to automatically collect samples conditionally. Any of the variables routinely measured by the system can be selected to trigger sampling. Therefore, samples can be collected that represent the sum of several respiration events wile excluding eructation events. Conversely, samples can be collected that represent several eructation events and exclude as much as possible normal breathing. In addition, the system is designed to collect quantitative subsamples where samples are collected as the gases exit the sampling pipe. At this point, the gases for the subsamples are well-mixed and capture rates and flow rates are very well characterized. However, the samples have passed through the inlet filter, the mixing elements, and the sample pipe. Thus, it is possible that specific components that may be of interest, such as oxygenated organics, and other sticky or reactive compounds could be partially or wholly scrubbed from the subsample air stream.

Therefore, the system also has the capability to collect qualitative subsamples at the manifold inlet very close to the animal's nose and mouth. At this point, gases of interest have not had a chance for significant interaction and scrubbing by surfaces; however, subsamples have not had a chance to become uniformly mixed with air flowing through the sampling pipe such that the determination of precise fluxes for the qualitative subsample is more uncertain. However, the qualitative subsamples are useful for exploratory research to determine the presence of specific compounds of interest. If the qualitative subsamples indicate that a compound of interest is emitted by an animal but the quantitative subsamples indicate the compound is scrubbed by the materials used in the GreenFeed unit, the materials of construction of the GreenFeed unit can likely be modified to minimize interferences so that quantitative fluxes can be measured in the future. For example, to be compatible with sticky volatile organic compounds, the sample pipe can be constructed of specially passivated stainless-steel and the stainless steel can be coated with fused-silica. If, for example it is determined through comparison of the quantitative samples and qualitative samples that the compounds of interest are lost in the particulate filter located at the beginning of the air pipe, the filter could be replaced by one made of materials compatible with the compound of interest, particles could be removed with an inertial impactor, or the gas of interest could be collected on gas-denuder tubes or other specialized analytical techniques commonly used to differentiate or to reduce interferences could be used if necessary. GreenFeed systems utilizing special materials compatible with more difficult to handle compounds of interest are likely to be very expensive to build and are likely to require more maintenance.

In general, many GreenFeed systems are designed to be easily portable. For example, the tie-stall unit can be easily moved from stall to stall by one person. This system could also be used in free-stalls or in feedlots. The GreenFeed pasture unit is mounted on a trailer that can be easily transported from paddock to paddock, and quickly set up for operation. The unit built into the robotic milking system is not designed to be quickly moved.

Greenfeed data processing systems are designed to be flexible and to allow integration with other sensors and data. For example, GreenFeed systems are designed for easy installation and integration into many brands of robotic milking systems, automated mineral feeders, and systems designed to monitor animal weight, animal food consumption and/or animal water consumption. Briefly, some common elements to each embodiment are: a system designed to restrict atmospheric mixing; sensors to quantify air flow rates; tracers to characterize breath capture rates under various atmospheric conditions and animal head positions; the potential for the conditional delivery of a specified feed, supplement, or water at specified times or when specified conditions occur; and the ability to use the data in near-real time to identify animals that do not meet performance boundaries (set for each individual or set for the entire herd). These elements together facilitate quick remediation activities such as delivery of specified supplements to individual animals or to the herd, identification of specific animals for expedited inspections, changes in the formulation of general rations such as the daily total mixed rations (TMR) (which often comprises the bulk feed for confined animals), and moving the animals to a different paddock or pasture.

With these above features in mind, one embodiment provides an apparatus for monitoring methane emissions from a ruminant. The apparatus includes a system or assembly adapted to entice a ruminant to voluntarily place its nose and mouth in a position that facilitates measurement of exhaled breath. The apparatus further includes a gas collection manifold with an inlet near the nose and mouth position in the ruminant enticement mechanism, and the gas collection manifold draws a flow of air into the inlet (such as with a fan in a collection pipe or the like). The apparatus includes a methane monitoring device monitoring methane in the gas collection manifold, including methane concentrations in exhaled breath of the ruminant and in air in the absence of the ruminant. Further, the apparatus includes a data analyzing station processing the monitored methane concentrations to determine methane emitted by the ruminant from rumen metabolism. A container is provided to dispense a supplement into the ruminant enticement mechanism for consumption by the ruminant, and the container is typically operable to dispense the supplement in response to the determined methane emitted during rumen metabolism. In some embodiments, the supplement is adapted to reduce emission of methane in the exhaled breath of the ruminant.

The ruminant enticement mechanism may include a feeder shell with an opening for receiving the nose and mouth of the ruminant, and the feeder shell may include a wedge-shaped body mounted to be pivotal in wind such that the opening faces away from a direction of the wind to limit mixing in the feeder shell. The ruminant enticement mechanism may include an animal identifier for identifying the ruminant, and a light and sound assembly for selectively emitting light and sound when the identified ruminant is eligible for monitoring or feed via the apparatus. In some cases, the determined methane emitted by the ruminant is a measure of a flux of methane in the exhaled breath, and the measured flux is determined based on total flow in the gas collection manifold. The apparatus may also include an airflow sensor measuring the total flow and a tracer release mechanism for selectively discharging a quantity of a trace gas. In such embodiments, the data analyzing station may further operate to determine a capture rate for the exhaled breath via the inlet based on a monitoring of the trace gas and the measured total flow. In some applications, the data analyzing station further operates to initiate a report on health, dry matter intake, or breeding status for the ruminant based on a comparison of the determined methane to a threshold methane value.

BRIEF DESCRIPTION OF THE DRAWINGS

FIG. 11 illustrates a table 1100 of the daily averaged $CH_4$/$CO_2$ ratios for a set of 14 cows over a 54-day study at the same dairy and during the same test as shown in FIG. 10;

DETAILED DESCRIPTION OF PREFERRED EMBODIMENTS

The methods and systems described herein are expected to substantially reduce the parasitic GHG emissions from livestock and increase grazing efficiency. These techniques for monitoring and reducing/controlling ruminant methane production are further expected to have substantial economic potential. In addition to animal efficiency gains, actual methane emission reductions expected based on the wide range of literature values may, for example, produce GHG offsets worth from $1 to $20 (US dollars) per animal per year depending on diet and animal genetics.

Figure 2:
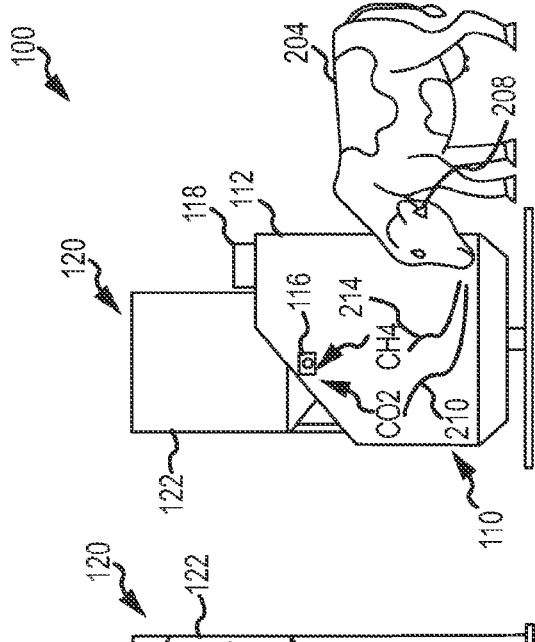
FIGS. 1-3 illustrate front, sectional, and top views, respectively, of one embodiment of a system for monitoring and controlling ruminant methane production/emission (or a GreenFeed system)
Figure 3:
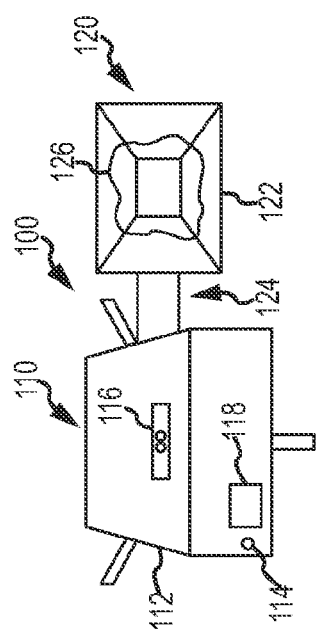
Figure 1:
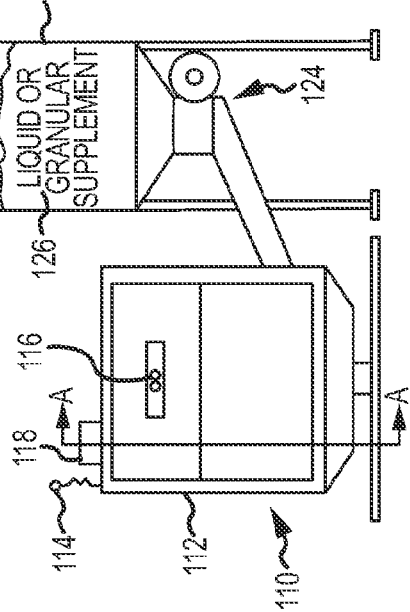

FIGS. 1-3 illustrate exemplary components of one embodiment of a system 100 for monitoring and controlling ruminant methane production/emission. The illustrated system 100 may incorporate a ruminant ear tag reader 114 (e.g., a reader adapted for reading an RFID tag 208 placed on an ear of an animal 204) so that animals 204 with ear tags 208 can approach the station 110 and be identified with the shown RFID reader 114 that provides data to the data logger 118, with the reader 114 and data logger 118 being mounted on the hood/manger 112 of the station 110 in this example system 100. The GreenFeed system 100 (with "GreenFeed" system being used interchangeably herein with labels such as system for monitoring and controlling ruminant methane production/emission and the like) is in some cases designed to dispense custom formulations into the manger 112 for each specific animal 204 by selectively controlling/operating one or more feed system 120 or its dispensers/hoppers 122 with feed/chute control mechanisms/assembly 124.

For example, the dispenser/hopper 122 may include liquid or granular supplement 126 and may be selectively operated. This hopper 122 may have one or more compartments (with only one shown for ease of illustration but not limitation) each containing one or more differing supplements 126, and these compartments may be separately operated by the output mechanisms 124 of the automated nutrient dispenser 120 in response to methane and carbon dioxide emission determinations (such as by the illustrated $CH_4$ and $CO_2$ analyzer 116 that may process releases 210, 214 of $CO_2$ and $CH_4$ within the hood/manger 112 and provide data or control signals to the automated nutrient dispenser 120 and, in some cases, determinations of present/real time metabolic efficiency of the feeding animal 204. The system 100 (or its software programs or modules not shown but run by one or more onboard/local processors or remotely located processors) may also make decisions based on measurements of animal temperature (e.g., measured by way of a sensor placed inside the animal's ear canal (not shown in FIGS. 1-3)) and/or based on animal metabolic gases measured by the GreenFeed system 100. Numerical computer models resident in a computer module of the system 100 (such as in the analyzer 116, data logger 118, automated nutrient dispenser 120 but not specifically shown) interface with the data logger 118 either built into the system 100 or operated remotely.

Figure 4:
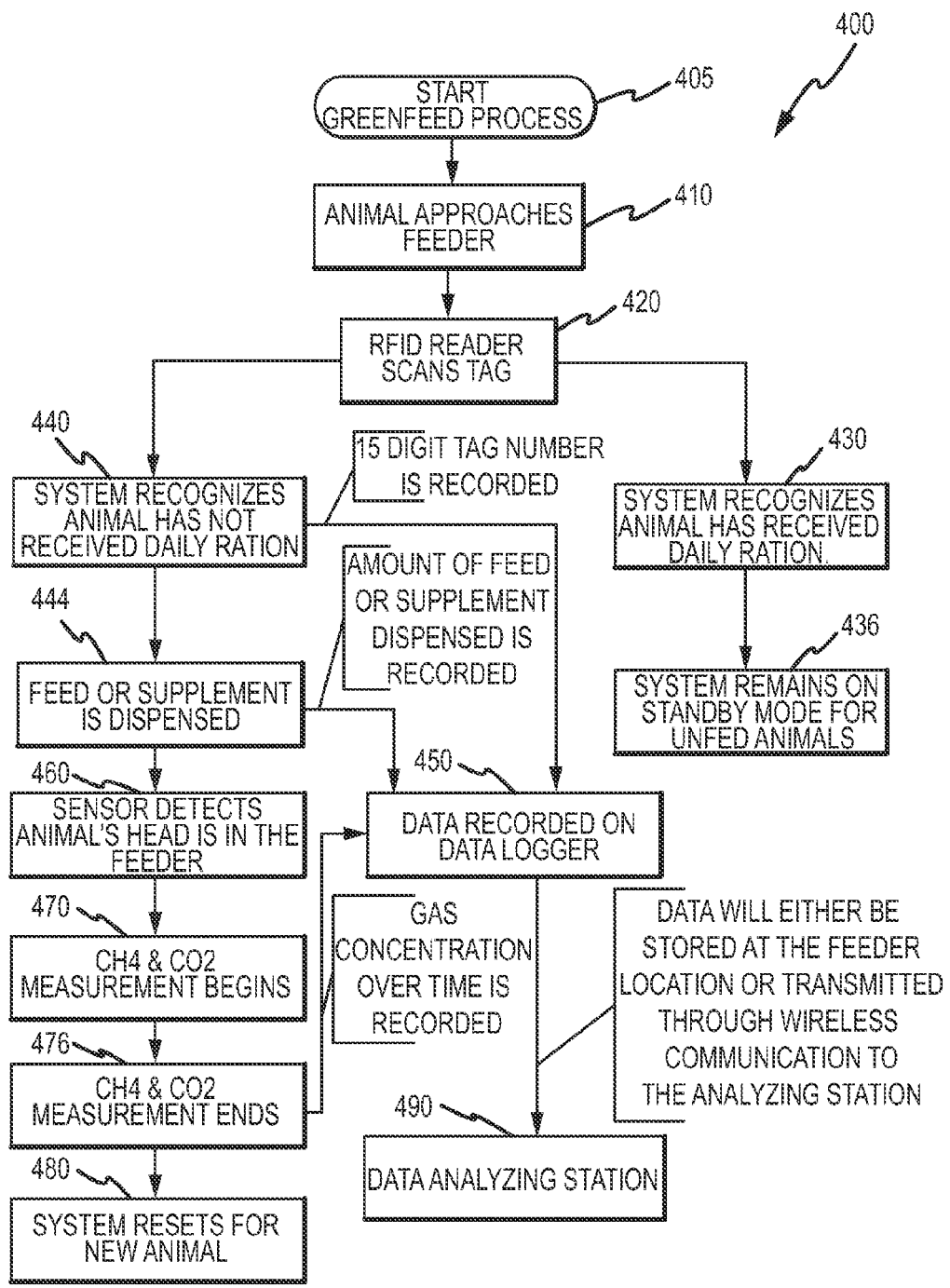
FIG. 4 illustrates a method of monitoring and controlling ruminant methane production and/or emission such as may be implemented, wholly or in part, by operation of the system shown in FIGS. 1-3.

The following sequence describes exemplary operation of the illustrated GreenFeed system 100 during an animal measurement cycle with at least some of these steps being illustrated in the example flow chart for a GreenFeed process 400 in FIG. 4.

A GreenFeed system, such as system 100, may include: one or several dispensers (such as dispenser 122) for specific feed supplements (such as liquid or granular supplements 126); a monitoring system for metabolic gas emissions from animals (such as NDIR $CH_4$ and $CO_2$ analyzer 116 and data logger 118 of system 100); an RFID reader (such as reader 114) to read data from each animal's ear tag (as shown at 208 in FIG. 2); sensors built into a ground-mounted weight scale to record the approaching animal's weight (not shown in FIGS. 1-3 but may be provided in system 100); solar panels to supply power when main power is not available (not shown in FIGS. 1-3 but also may be included in system 100); and batteries that are recharged by the solar panels residing in a pasture (again, these are not shown in FIGS. 1-3 but are included in some systems 100 to practice embodiments of the invention). The process 400 starts at 405 such as by providing the animal feed stations and nutrient dispensers within a pasture or feeding area for ruminants, and step 405 may also include loading processing software/modules in the system to analyze monitored emissions data and, in response, to operate the nutrient dispenser for a particular animal (such as animal 204) or the monitored/controlled herd.

Periodically, the system (such as system 100) turns on and makes measurements of ambient air inside the manger portion of the GreenFeed system (such as the hood/manger 112 of feed station 110 shown in FIGS. 1-3 where the animal 204 inserts its head). These air samples are the background samples, and sampling may be performed by the analyzer 116 or other devices of a system (such as system 100). The GreenFeed system may incorporate optional front and side curtains (not shown in system 100 of FIGS. 1-3) to restrict mixing of ambient air under extremely windy conditions. Alternatively or additionally, the GreenFeed system manger/feeder unit (such as unit 110 of system 100) may be made to pivot so that its opening is always aligned downwind. This will help to restrict atmospheric mixing that could cause dilution of metabolic gas emissions and concentrations. The system may include sensors to monitor animal head position when under the hood, wind speed, wind direction, air temperature, relative humidity, air flow rate through the air sampling pipe, and other sensors. Data from any or all of these sensors may be used to determine mass fluxes of metabolic gases through the system and animal breath capture rates under typical conditions. The data may also be stored and used to select measurements accurate to defined specifications.

When an animal approaches at step 410, the system monitors its ear tag with a tag or RFID reader at 420 and such reading may awaken the feeding system. A computer program run by a processor(s) may be provided in the GreenFeed system that monitors the time of day and determines whether or not to dispense a specific feed material based on the time of day and/or the particular animal such as based on the ear tag determination. In some cases a placebo feed, one that attracts the animal but has no significant metabolic effect can be dispensed. The placebo documents the baseline for the performance of the specific animal. As shown, the system may determine at 430 that the animal linked in a database with the read ear tag has received their daily ration, and, if so, the method 400 continues at 436 with the system operating in a standby mode for additional approaching animals, e.g., unfed animals to dispense appropriate nutrients. The animal may be provided an indication of its eligibility to receive feed material by a system of visual and/or audio cues. Visual cues can include specific colors. Audio cues can include specific tones. Tones and colors can be associated with specific animal monitoring unit operations.

After the RFID tag is read at 420, the system (or its monitoring software) may determine at 440 that the animal associated with the read ear tag has not received its daily ration of the methane controlling or other nutrients. In some cases or implementations of process 400, the tag number of the ear tag (e.g., a 15-digit number or the like) may be recorded in the data logger as shown at 450. At 444, based on a lookup in a database for the particular animal, the automated nutrient dispenser may be operated to dispense feed and/or nutrient supplements, and the amount of feed and/or supplements dispensed may be recorded to the data logger or other data storage device in the GreenFeed system as shown at 450.

At 460, a separate sensor/detector associated with the feed station or the RFID reader may trigger the gas and/or other monitoring instrumentation to turn on. The monitors (such as analyzer 116 in system 100) can either be mounted within the GreenFeed hood and/or they can be located remotely, and air samples collected from within the GreenFeed hood and manger can be routed to the analytical instruments. In one implementation, measurements are made as shown at steps 470 and 476 of methane, carbon dioxide, and water vapor such as with the sensor and/or measurement devices shown in FIGS. 1-3. In addition, animal weight, animal milk production, animal core temperature, and other data can be routed to the data logger (such as data logger 118 of system 100) and computer system of the illustrated feeding station of FIGS. 1-3.

These data may then be transferred to a computer program or series of programs in which numerical models are run such as within the data analyzing station 490 to result in or produce decisions about the types and amounts of specific antibiotics, and/or nutrient supplements to dispense at step 444 in the next or current feeding of animal or access of a feed station (e.g., provide a particular "prescription" or "diet" of supplements and the like to dispense at this time to this particular animal based, typically, on the methane emissions detected and/or on metabolic efficiency of the animal). Alternatively, these data may be used to identify individual animals that are at risk or in the early stages of diseases. In other cases, these data may be used alone or in combination with other external data to identify animals that are likely to be in heat. In still other cases (or additionally), these data may be used alone or in conjunction with other data to identify animals that achieve higher production efficiencies and, thus, could, for example, be useful for future breeding programs. The gas concentration over time as measured in steps 470 and 476 may be recorded by data logger as shown at 450 concurrently with or prior to transfer to the nutrient supplement selection program module or programs at data analyzing station 490. The data may either be stored at the feeder location or transmitted through wireless or wired communications to the analyzing station 490.

As shown in method 400, based on the supplement determinations by data analyzing station 490, the GreenFeed system (such as system 100) dispenses the required (or determined useful for controlling methane production) nutrient supplements and/or antibiotics or a placebo into the manger by operation of the feed dispenser/hopper (e.g., the hopper 122 with liquid or granular supplement 126 to meter out a particular amount of one or more supplements/feeds 126 as shown in FIGS. 1-3).

The analytical measurement system (e.g., analyzer 116, data logger 118, and data analyzing station 490 and the analyzing stations software modules) measures changes in methane and carbon dioxide ratios. When an eructation occurs, methane concentrations will spike. Carbon dioxide from aerobic respiration will tend to increase linearly as the animal breathes while its head is in the space indicated by the head-position sensor to be optimal for measurement (i.e. within the restricted space). Since little methane is emitted in an animal's breath, aerobic and anaerobic respiration can be differentiated. FIG. 3 illustrates a typical pattern of ruminant animal breath and eructation cycle. This data can then be compared to data obtained from the baseline case by the data analyzing station 490, for example, for the individual to determine relative changes in methane emission rates. A numerical model (e.g., software module run by station 490) describing animal metabolic functions can then be initialized with this data either on a remote computer or on a resident computer of data analyzing station 490 to calculate greenhouse gas reductions.

The methane monitoring and emission control or GreenFeed system may incorporate a telemetry system to transmit data to a remote computer (or data analyzing station 490 as shown in FIG. 4) where it may be stored in computer memory or data storage (such as in a database with supplement and methane emission data collected at the data logger for each animal) and/or further processed for a plurality of animals and/or stations as shown in FIGS. 1-3. The GreenFeed system may include a resident computer (using a processor(s) to run one or more software programs/modules not shown but provided in some embodiments in the data analyzing station 490 to cause the computer(s) or their processor to perform particular functions) to process data and aggregate the collected and logged data to generate a report of emission reductions and performance efficiency for each individual animal. In some embodiments, the system and its data analyzing station may function to aggregate data for individual animals and/or for the entire herd. The GreenFeed system may, in some embodiments, be linked to other systems, such as but not limited to the C-Lock Technology and/or GreenCert™ (U.S. Pat. Nos. 7,457,758 and 7,415,418, which are both incorporated herein in their entirety by reference). In some embodiments providing linkage between the GreenFeed system and other systems, the ruminant monitoring and emission control data may be transformed into carbon credits (e.g., C-Lock certified carbon credits or the like) that may be transparent and verifiable. In other embodiments, the system might send an electronic alert to managers or it might physically mark an animal with suitable paint or a marker to indicate that the animal requires individual attention.

A tracer release can be incorporated into the GreenFeed system so that a known quantity of an easily-measured trace gas, not generally produced by ruminants is released into the GreenFeed manger area (e.g., into the hood 112 of feed station 110 in system 100 of FIGS. 1-3 for measurement by analyzer 116 or a separate trace gas analyzer). Exemplary tracers include butane, propane, ethane, sulfur hexafluoride and/or many other compounds that are typically readily available and easy to measure. Propane is preferable since it is easy to purchase and it is a liquid under pressure so it has a very high gas storage density. Commercial propane contains an odorant such as diethyl sulfide to which humans are sensitive so that leaks can be detected by the human nose. In some cases, it is desirable to include a scrubbing cartridge containing a material that absorbs or that transforms the odorant and traps it to remove this compound from propane so it does not disturb the animal using the animal monitoring unit. Measurements of the decay of the selected tracer gas may be used to calculate dilution from mixing with ambient air. Alternatively, the tracer release can be continuous over a long enough time-period so that the steady-state concentration can be used to estimate dilution of the metabolic gas emissions from animals (by the analyzer 116 or data analyzing station 490 and its software/processing modules). In other embodiments the flow of the tracer is alternated from release at the entrance of the animal monitoring unit in proximity of the animal's breath where it is diluted by ambient air (A), to release inside of the air sampling tube where air flow rates are independently measured, such as with a hot wire anemometer or a pitot tube system or other device. In this case (B), 100 percent of the tracer is captured. The ratio of the two concentrations (A/B×100) defines the breath capture efficiency and can be used to correct capture rates for non-ideal conditions where A is less than B. Alternatively, (or preferably) in addition, an animal head position sensor can be used inside the hood to indicate when the animal's mouth and nose are in optimal position for quantitative measurement. The head-position sensors suitable for monitoring head position include ultrasonic sensors and infrared sensors.

Figure 5:
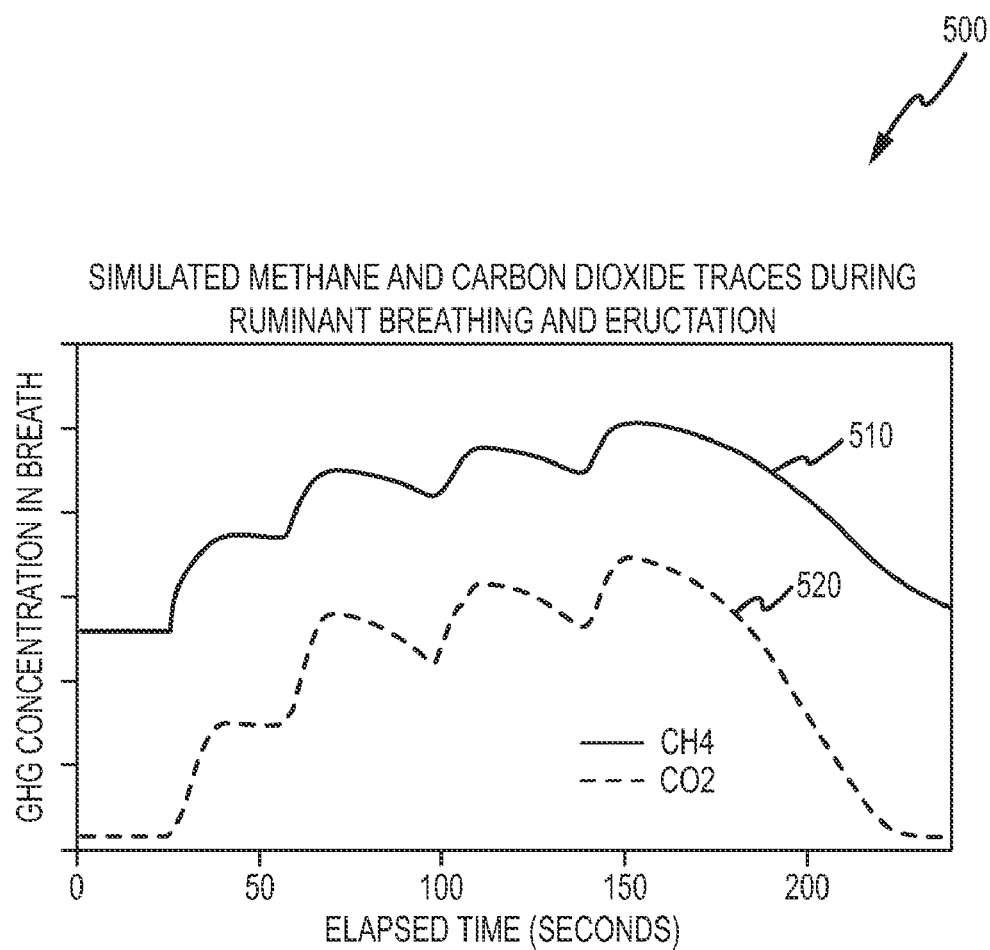
FIG. 5 is a graph illustrating a typical pattern of methane and carbon dioxide traces that may be measured within a manger/hood of a feed station in a GreenFeed system in accordance with an embodiment of the invention in a ruminant's breath (e.g., during an eructation cycle or the like)

In this way, absolute mass fluxes of methane and carbon dioxide can be measured or determined (by, for example, the data analyzing station 490). FIG. 5 illustrates a typical pattern 500 of ruminant animal breath and an eructation cycle that may be measured or monitored by the NDIR $CH_4$ and $CO_2$ analyzer 116 and/or determined by data processing software/modules of the data analyzing station 490 as part of process 400. Line 510 represents measured or determined concentrations of $CO_2$ in a ruminant's breath (as may be measured in a manger or hood 112 in a system 100) while line 520 represents measured or determined concentrations of $CH_4$ in the same ruminant's breath.

When the animal removes its head from the GreenFeed system (or a hood 110), the system may in some embodiments be set to continuously monitor the air within the manger area (or hood 110) of the system to monitor the decay of methane and carbon dioxide concentrations to ambient levels due to mixing with the atmosphere (such as by operation of an analyzer 116 and data logger 118 as described in the method 400 and by processing of collected/monitored data from the animal as described for data analyzing station 490 and its processing modules).

For rangelands where many hundreds of animals could be present, a monitoring and emission control system may sometimes be set up to only allow selected individuals to have access to the GreenFeed monitoring system (or to only monitor and control emissions from such animals based on identification of this subset of the ruminants via ear tag/RFID or other animal identification). The nutrient treatment may then be delivered to all animals, with the system being used to collect data from a representative sampling of individual animals (e.g., the same ones used to set the nutrient treatment or a differing set). The results may then be extrapolated through numerical models to quantify the results for the whole herd. In this way, one unit could serve several hundred animals and not every animal would have to be sampled all of the time (but, they may be in other implementations). Similarly, this approach might be useful in a dairy where several hundred or several thousand animals are housed. Selected individuals might be monitored to indicate overall feed efficiencies, health trends, and methane emissions from the herd. Alternately, if all animals are equipped with RFID tags, the system may be programmed to select individuals from among the entire herd for random or routine sampling. In this case, the system can utilize light and/or sound to indicate to approaching animals their eligibility to utilize the system.

In brief, systems according to embodiments may be described as useful for monitoring changes in relative emission rates. It can supply data to numerical models to estimate methane fluxes and to calculate GHG emission reductions that may then be converted to or used to determine carbon credits. The system may use an internal or an external tracer to measure mass fluxes of methane, carbon dioxide, and other metabolic gases. The system may be configured in many ways.

Figure 6A:
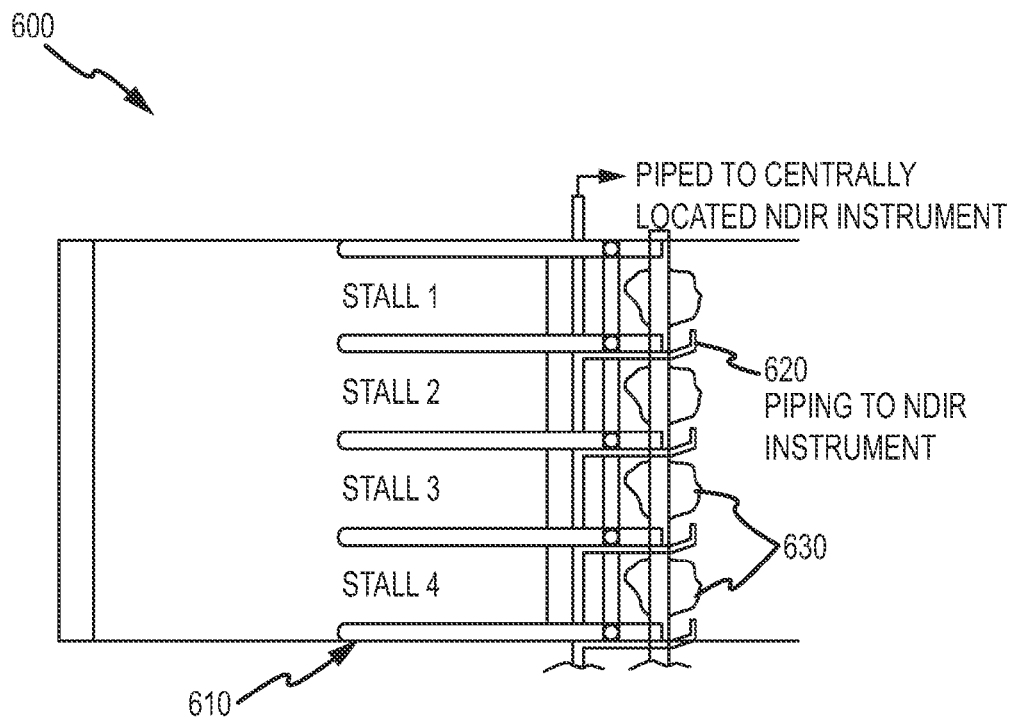
FIGS. 6A and 6B illustrate a portion of an embodiment of a GreenFeed system using a tie stall configuration to monitor and control GHG emissions of ruminants.
Figure 6B:
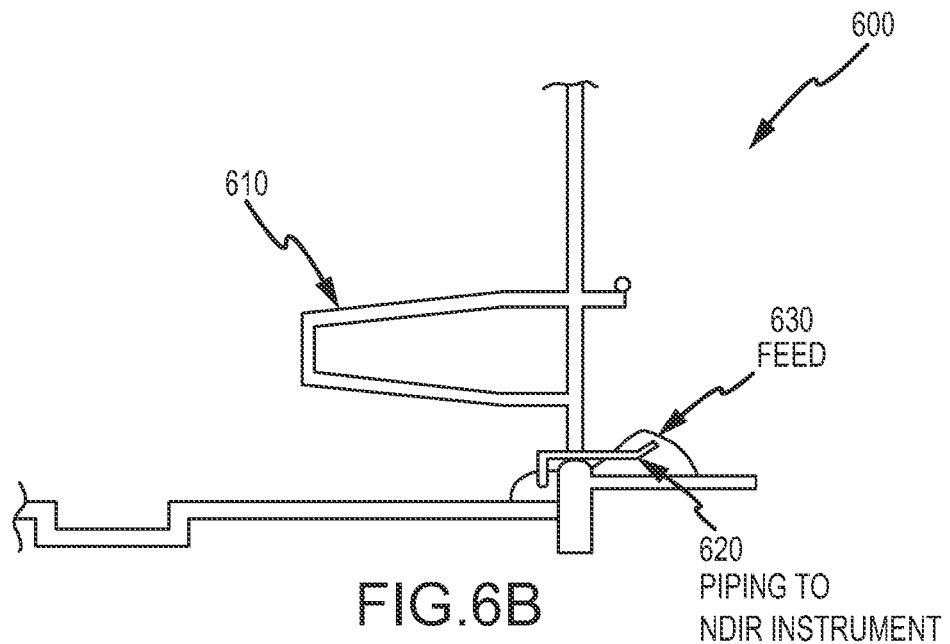

For example, as shown in FIGS. 6A and 6B (top and side views), a GreenFeed system 600 may be used in a group setting such as in a milking parlor or barn to measure all individuals at once. For example, the system 600 may be incorporated into headstalls 610 or other devices used to restrict animal movement. The system 600 includes piping 620 to move or transfer breath/gas samples from a feeding area (which may be hooded) in which the animal's head is located when provided feed 630 to one or more NDIR or similar analyzers/instruments. As discussed with reference to FIGS. 1-5, the feed 630 may be selectively modified in system 600 based on monitored levels of methane and/or carbon dioxide (as detected by operation of a $CO_2/CH_4$ analyzer and/or a data analyzing station and its running software modules) and/or be supplemented with select nutrients to reduce GHG production/emission.

In other embodiments (not shown), the monitoring and/or supplement dispensing portions of the inventive system are added to automated robotic milking machines to monitor methane and carbon dioxide ratios and/or fluxes of methane, carbon dioxide, and/or other metabolic gases while animals are being milked. As will be appreciated, the monitoring and control or GreenFeed systems may be used in nearly any setting where ruminants access food or water or otherwise place their heads in a certain position for an acceptable period of time to obtain breath monitoring measurements (e.g., the feed station of FIGS. 1-3 may be replaced by the stalls of FIGS. 6A and 6B, be replaced or used within an automated milking system in which ruminants are typically placed in a position for milking and are often concurrently fed or provided nutrients/supplements, and so on). Other places cattle and other ruminants may be forced to or willingly congregate (and which lend themselves as monitoring/nutrient dispensing stations) and where mixing of their breath in the atmosphere is somewhat restricted may include water founts or watering stations (that may be hooded or protected from winds and mixing as discussed above for the feed stations) and nutrient/salt lick-type stations, and the like. In other words, the terms "feeding station," "hood," and "manger" are intended to be construed broadly and may generally cover any device or arrangement in which a ruminant may place their head for a period of time and their breath may be monitored with at least some limitation on mixing with ambient air, and, at least in some cases, where nutrients/supplements may be dispensed to control or reduce GHG emissions and at least in other cases where the "bait" operates simply as an enticement for the animal to place its head in the appropriate position for monitoring.

One illustrative system in accordance with an embodiment of the present invention includes a comprehensive measurement and validation system for reduction of bovine methane emission. The system includes a methane ($CH_4$) measurement technology, e.g., one with the accuracy and reliability that may be used for generation of carbon credits, with one embodiment of the system including dual gas (methane and carbon dioxide ($CO_2$)), infrared measurement detectors. When incorporated into a nutrient block station, feed station, milking station/parlor, water fount, or similar implementation and, optionally, combined with a standardized emission credit determination system, the system for monitoring and controlling/reducing ruminant methane production provides a valuable tool for the reduction of methane emissions from bovine and other ruminant sources.

In operation of an embodiment of such a system, a ruminant's gaseous emissions are monitored, methane emissions are determined, and the ruminant's feed supply is adjusted or supplemented or the ruminant is otherwise treated to reduce methane emissions. In some cases, non-dispersive infrared instruments monitor carbon dioxide and methane emitted by a ruminant. The information thus obtained is considered (e.g., processed by software running on a system computer or by a system processor) along with animal statistics available from a database in system data storage and/or from information associated with an RFID tag attached to the ruminant, which may include heritage information, e.g., whether the animal is weaned, its age, and the like. Based upon the emission information and the other information about the ruminant, one or more of a plurality of supplements and/or a particular amount of the one or more supplements is offered or dispensed to the ruminant.

In an exemplary but not limiting method, a ruminant presents itself at a feeding station at which carbon dioxide and methane emitted by the ruminant in its breath are measured. Other measurements may also be taken. Along with information obtained from memory such as a ruminant tracking/monitoring database or from receipt of signals containing information stored on the animals RFID ear tag, at least one determination is made about the production of methane by the animal. Additional determinations which may be made include identification of one or more supplements or a mixture of supplements and amount or amounts thereof to offer to the ruminant to reduce the determined methane emission which would be expected to subsequently occur, should the ruminant's diet not be modified.

A ruminant methane monitoring and control feed station (e.g., a GreenFeed system or GreenFeed station) may be constructed and instrumented to function in several modes. In one example, the feed station includes a hood located over the feed manger to restrict the effects of the wind and serve to isolate and concentrate the breath of an individual animal. In this case, the animal, such as a cow, inserts its head into an opening in the hood or feed manger. At that time, a RFID or other reader or sensor reads an ear tag to determine the age and type of animal. Based on this information, a specific nutrient mix may be released. In a more typical embodiment, the mixture is designed specifically to reduce the production of methane by the ruminant or to meet a goal level of such emissions (such as to achieve a particular weight gain). The determinations controlling the type and amount of nutrient are in some cases based on input from sensors mounted inside the feed station and on the ground in proximity to the feed station. Information collected from such sensors may include animal weight in order to determine animal weight gain, methane and carbon dioxide ratios to determine animal metabolic efficiency, and additional measurements as useful to document performance (e.g., performance with regard to methane emission reduction/control and/or with regard to more optimum weight gain or weight maintenance such as for a mature dairy cow) and, in some cases, to generate CERCs (Carbon Emission Reduction Credits.)

In another example, in addition to the measurement of methane and carbon dioxide ratios in the animal's breath, the insertion of the animal's head into a feed hood, stall, or feed station of the present invention triggers the release of a specific, controlled flow-rate tracer. The tracer, for example, may be an inert gas such as sulfur hexafluoride, butane, or other chemical compound that is measured with instrumentation installed in the feed station. The dilution of the tracer is used to correct methane and carbon dioxide measurements for the effects of atmospheric dilution. In this way, the flux of methane and carbon dioxide can be determined as well as the metabolic methane and carbon dioxide ratios.

In another example of the present invention, the animal's breath is used as a tracer of atmospheric dilution. Because the breath of a ruminant is saturated with water vapor and is released at very close to the same temperature as the internal body temperature of the animal, both water vapor and temperature (latent and sensible heat) can be measured. A solid-state or similar sensor can be used to measure temperature and humidity of ambient air and also to measure the temperature and humidity of the air that includes the animal's breath inside the GreenFeed manger, other at least partially enclosed space, or even an open space in some applications. Since the animal's breath is saturated with water vapor, the difference between the water vapor mixing ratio of ambient air and that of the air inside the manger of the GreenFeed system can be used in some implementations to monitor mixing of air inside the feed hood of the GreenFeed system. This measurement of mixing can then be used to calculate the dilution of the animal's metabolic gas emissions and, therefore, the fluxes of methane and carbon dioxide can be determined. Alternatively, fast measurements can be made using eddy correlation technology. A fast eddy co-variance flux instrument that measures latent and sensible heat flux can be incorporated into the instrument suite of the feed station, allowing the measurements to be used to calculate dilution due to mixing of the animal's breath with the air inside the feed hood. Dilution is calculated, and the fluxes of methane and carbon dioxide from the animal are measured and documented in addition to determinations of metabolic efficiency ratio (e.g., a ratio of methane to carbon dioxide).

In a further embodiment, a nutrient block feeder system (not shown but similar in arrangement as the system 100 in FIGS. 1-3) can be deployed to monitor methane and carbon dioxide concentrations of tidal breath as well as the eructation of ruminant animals while they are in a pasture. The system looks similar to a hooded saltlick mounted on a short post. The nutrient block in some embodiments is surrounded on all but one side by a cover. The uncovered side has an opening large enough for an animal to insert its head and access a nutrient block or container(s) of one or more nutrients. Mounted under the hood is an RFID tag reader for reading/receiving information about each animal from its RFID ear tag. The nutrient block station further includes a methane/carbon dioxide monitor, a data logger, and, optionally, a communication device (e.g., a Bluetooth transmitter, a cell phone with modem, or other wireless/wired communication device). The station sometimes contains a GPS chip to obtain and collect information about location of the unit and the time of day that it was accessed by the animal. The system may be powered by batteries such as those recharged by solar cells but other battery-based power sources or power sources may be utilized in the GreenFeed systems described herein.

In one method for monitoring and controlling/reducing methane production of a ruminant, when an animal approaches the nutrient block station, the system turns on for a specified time-period to monitor and document methane/carbon dioxide ratios, the animal's identification number, the time, and/or the location of the station. Based on information collected and obtained and determinations made based on the information by the system's software modules or programs, a supplement is made available (by computer-based control of feed/supplement dispensers) to the animal to control, reduce, or maintain methane emissions at a presently set or defined level, which may be stored in a database and associated with the animal's ID (which, in turn, may be stored on their RFID ear tag or accessible via an ID code on their ear tag). Normally, animals may consume one to two ounces of supplement per day. The amount of supplement consumed per animal may be controlled by the GreenFeed system by modifying the salt content of the supplement (e.g., releasing additional salt with the supplement, releasing a supplement with a higher salt component, or the like).

In some cases, the station is placed strategically in a field near a point of congregation such as a water source or water fount. A station may be used to serve up to 40 to 100 or more animals. The system may be loaded with a placebo mineral block to document the baseline methane emissions for the herd and the pasture. In this way, the mineral supplement may be added to document GHG reductions, so that each animal, as well as the whole herd, is monitored in a very cost-effective way. If more exact emission rates of methane and carbon dioxide are useful (instead of relative changes in efficiency), an optional tracer release system may be incorporated into an embodiment of the monitoring and control system. The tracer release system utilizes a third chemical species (e.g., propane, butane, or an inert fluorocarbon that would emit at a defined rate). The dilution of the tracer is then utilized to correct for limited atmospheric mixing, which occurs when the animal's head is "under the hood." This may, in some cases, not be necessary, however, since concentrations of methane and carbon dioxide under the hood will often be many times greater than ambient concentrations, and efficiency gains may be documented with the ratio of the two gases not the absolute emission rate. The data is then transmitted or linked to a computer in which a resident numerical or processing module can determine methane emission reductions and, optionally, convert those reductions into verifiable carbon credits.

In addition to the generation of high value GHG offsets, the system may serve as a livestock management tool. The methane/carbon dioxide ratios obtained provide valuable information about the condition of the animal and of the pasture. In addition to the generation of high value GHG offsets, the system may serve as a livestock management tool. The methane/carbon dioxide ratios obtained provide valuable information about the condition of the animal and of the pasture. Methane and carbon dioxide mass fluxes can be used along with numerical models to estimate dry-matter intake, digestibility, and animal efficiency. This data can be used along with production data to select breeding stock that produces more meat and milk on less feed resulting in lower emissions of greenhouse gases and improved animal welfare and global sustainability.

Methane and carbon dioxide concentrations under the hood of the mineral block monitoring system are expected to be fairly high, i.e., much above ambient, such that measurements can be made with relatively inexpensive and well-tested equipment. For example solid-state sensor equipped instruments designed to control air quality in buildings or instruments designed to detect explosive or toxic gases may be useful in GreenFeed animal measuring units. If preferred, however, an embodiment of the system may use an OEM NDIR instrument. Since the station is automated with computer-based controls for collecting data, processing the data, and selectively dispensing feed/supplements, the monitoring costs per animal may be quite low. Because one station can be shared among many cattle or other ruminants, the cost per animal may also be relatively low.

Useful parameters to be evaluated for methane and $CO_2$ include a detection limit, a detection range, a response time, repeatability, and selectivity. To determine a detection limit and range, in one non-limiting example, methane concentrations of 100 ppm (parts per million) to 2% (well below the LEL) and $CO_2$ concentrations of 400 ppm (ambient background) to 5% are evaluated. Response times may be calculated by generating a response curve and analyzing the curve to determine the time for the detector to reach 90% of its peak value based on a step change in gas concentration. Repeatability of the detector is determined by exposing it to step changes between a specific concentration and a background without challenge gas multiple times. The standard deviations of the responses may be calculated to provide a quantitative measurement of repeatability. Detector selectivity is proven by exposures to other gases likely to be present. These gases primarily include alcohols from the animal's breath (in the sub-10 ppm range) and the water vapor in their breath. A potential interferent gas may be ammonia from animal waste.

Information from the detector and the tracking system is typically transmitted from the nutrient block station or other collection station to a central location where data may be collected from multiple stations. Wireless networking technology is used in some implementations, with some embodiments using a commercially available wireless communication solution or technology such as Bluetooth or 802.11g (WiFi). Each of these technologies has advantages and disadvantages, and the appropriate solution for a given application is highly dependent upon the details of a specific application. The 802.11g standard is relatively inexpensive due to its wide commercial use and acceptance. This standard uses direct sequence spread spectrum technology and is somewhat susceptible to RF noise and interference. The Bluetooth standard is also low cost and is less susceptible to RF noise and interference because it uses a frequency hopping spread spectrum technology. A preferred central data collection unit is a PC or similar computing devices with conventional and well-known data storage/memory devices.

In brief, use of the methane production monitoring and control techniques and devices described herein is expected to reduce the parasitic GHG emissions from livestock and increase feed efficiency. Changes in methane and carbon dioxide ratios and/or fluxes for individual animals over short time periods may also identify animals in need of individual attention for breeding or that are at substantial risk of being in the early stages of illness. Use of these systems and methods is further expected to have a desirable and even substantial economic potential. In addition to animal efficiency gains, actual methane emission reductions expected based on the wide range of literature values may produce GHG offsets worth from $1 to $20 (U.S. dollars) per animal per year. Actual methane reductions that can be accomplished can depend on diet, including antibiotics and/or other mineral or nutrient supplements, and animal genetics.

In some embodiments, a precision ruminant feeding and greenhouse gas performance monitoring system is provided that includes a plurality of individual feeding or GreenFeed systems, e.g., that may be spread about a field for access by a herd of ruminant such as sheep, cattle, dairy cows, undomesticated animals such as deer or elk, or other non-ruminant animals such as pigs and horses. Each station of the system may include: a feed/supplement delivery system and hopper; a feeding station; an RFID tag and reader system (e.g., an RFID panel reader for use with conventional RFID ear tags for cattle and other domesticated animals); a data logger and instrument controller; and a nondispersive infrared sensor (NDIR) or similar device for determining presence/quantities of methane and carbon dioxide (and other gases). Each grain/supplement delivery system and hopper may take a number of forms with one example being a metal or plastic hopper (e.g., with up to a two-ton capacity or the like) combined with a feed delivery system/dispenser mechanism for selectively delivering feed and/or supplements. The hopper/delivery system may be an enclosed feeder station that is, for example, capable of delivering up to about 4 pounds or more of feed per second. The individual feeding stations or hoods fed by such a delivery system may take the form of one-piece molded poly feeders or the like with, for example but not limitation, a heavy steel base or other devices for substantially rigid mounting. In some cases, each feeding station with its hood and manger is able to hold about 50 pounds of feed and/or supplement.

The animal monitoring portion of the system may include components able to identify each animal (such as a tag attached to an ear with an RFID tag storing an ID associated with the animal, a tag with a readable number, a tag with a barcode, or the like) and may also include a temperature monitor such as one that may be mounted with the ID tag or separately on the animals ear (e.g., a thermistor with electronics, an antenna, and battery for sensing and transmitting the animals temperature information wirelessly to a receiver on or near the feeding station/feed delivery system in the GreenFeed system/station). The processor/controller used to run software modules for processing methane, carbon dioxide, animal data, and the like and for controlling the feed delivery system may take a number of forms to practice the invention and, in one case, the controller is a Phidgets SBC Linux-embedded computer available from Phidgets, Inc. Likewise, the analyzer used to obtain methane and carbon dioxide (and other gas) measurements may take numerous forms to practice the invention, with one embodiment using an NDIR analyzer (e.g., a $CO_2$/$CH_4$/$H_2O$ Analyzer distributed by Sensors, Inc. or the like) that provides a real time, trace gas monitor able to measure carbon dioxide and/or methane, with parts per million (PPM) sensitivity).

Figures 7A, 7B:
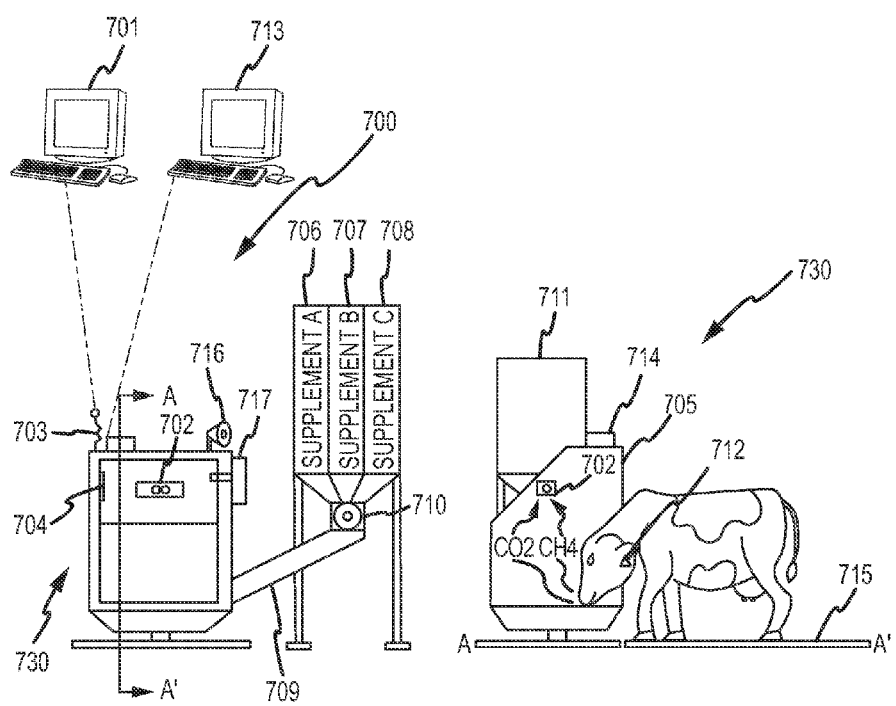
FIGS. 7A and 7B illustrate, similar to FIGS. 1-3, an embodiment of a system for monitoring and controlling ruminant methane production/emission (or another embodiment of a GreenFeed system)

FIGS. 7A and 7B illustrate another embodiment of a GreenFeed system 700 that may be utilized to provide precision ruminant feeding to control GHG emissions and other parameters (such as ruminant weight gain and the like) and to provide GHG performance monitoring. The system 700 includes a number of the features or aspects of system 100 of FIGS. 1-3 and the description of system 100 may be applicable or relevant to system 700.

The system 700 includes a data analyzing station 701 (e.g., that may provide the functionality of data analyzing station 490 of FIG. 4). Data from a remote feeding station 730 may be transmitted via wireless communication to the data analysis station 701. The wireless data analyzing station 701, which may be a computer with a processor, I/O devices, a monitor, memory, and software (e.g., programs useful for providing the processing and other functions described herein), may operate to analyze and store the following data in local or remote memory or data storage: (i) ambient temperature; (ii) ambient pressure; (iii) relative humidity; (iv) wind speed; (v) time and date; (vi) $CH_4$ and $CO_2$ concentrations over time (e.g., ambient and for individual animals); (vii) tracer gas type and amounts released; (viii) C-Lock carbon credit type information which may include, for example, data useful for a C-Lock Ruminant Module such as emissions baseline, change in emissions baseline, uncertainty, and incremental GHG reductions; (ix) animal identification through RFID technology; (x) animal body temperature; (xi) animal production statistics (e.g., beef statistics (e.g., current weight, gained or lost weight, rate of weight gain, estimate of future weight, feed efficiency compared to methane production, and $CO_2$ emissions per pound of gross animal weight) and dairy statistics (e.g., current milk production, increase or decrease of milk production, feed efficiency compared to methane production, and $CO_2$ emissions per unit of milk produced); (xii) animal genetics tracking (e.g., tracking and record of genetics bloodlines as it relates to methane production); (xiii) record of feed type and ration; and (xiv) formulation of future feed mixture and amount.

The system 700 may further include one or more nondispersive infrared sensors or other devices 702 useful for measuring $CO_2$ and $CH_4$ releases from a ruminant when their head is placed within the hood/manger of feeding station 730 (it should be noted that the feed station or its hood may be replaced by other stations such as milking stations in which a ruminant may insert their head or have their body/head in a particular position for a period of time allowing breath analysis). In one embodiment, the sensor(s) 702 may include a 3-beam optical design for $CH_4$, $CO_2$, and reference gas within a single light pipe or the like.

The system 700 may also include a wireless data communication device 703 mounted on or near the feed station 730. The communication device 703 may include a cellular digital modem or common technology to transmit stored or real time data from analyzer 702 and/or data logger 714. An ear tag scanner 704 such as a radio frequency identification (RFID) tag scanner may be placed or provide on or near the feed station 730, and the scanner 704 may scan and record individual animal data (in its own memory or data logger 714).

The feed station 730 may include an animal feeder such as a hooded manger or the like that is associated with hopper or gravity feed supplement bin 711. The bin 711 may have a number of separate compartments or bins for selectively providing a like number of nutrients and/or supplements to control GHG production/emission or achieve other goals such as weight gain. As shown, the hopper 711 includes three separate compartments with a first compartment 706 used to store/contain Supplement A (such as a first formulated supplement to reduce methane and/or increase animal production), a second compartment 707 used to store/contain Supplement B (such as a second formulated supplement to reduce methane and/or increase animal production), and a third compartment 708 used to store/contain Supplement C (such as a third formulated supplement to reduce methane and/or increase animal production).

The system 700 further includes a conveyer or gravity shoot 709 linking the bin 711 with the hood/manger 705 of feed station 730, and the gravity shoot/conveyor 709 supplies animal feeder 705 with feed supplement mix, which includes one or more of the supplements/nutrients from compartments 706, 707, 708. The system 700 includes a supplement measurement and mixing device 710 at the outlet of the supplement bin 711 (e.g., controlling output of each compartment 706, 707, 708 and its contained supplements), and the mixing device 710 mixes and measures individual animal ration from three or more store feed supplements, such as in response to control signals from the data analyzing station 701 (or software/hardware on the feed station 730 such as part of data logger 714 or the like). Each ruminant (or select ruminants within a herd) may be tagged (such as in the ear) with an individual animal radio-frequency identification tag 712, and the tag identifies individual animals to the system 700 (such as by reading by the tag scanner 704 that may provide the data to the logger 714 and/or the data analyzing station 701 for look up of the animal's ID, information, and the like and/or for storage of collected data corresponding to the animal's accessing the station 730). In some embodiments, the tag 712 also acts to monitor temperature of the animal, and this data may be read by the scanner 704.

In some embodiments, the system may also include a metabolic gas intake manifold to collect the animal's breath and rout it to an air sampling pipe through which air is pulled by a fan and from which metabolic gases are measured. The air flow inside the air sampling pipe may be mixed with mixing devices to improve plug flow and to reduce the variability of the flow rate across the pipe. The airflow through the pipe can be determined by measuring the flow rate with a hotwire anemometer or with a pitot tube system such as the EE66 air velocity transmitter available from JLC International or the like. Air flow rates through the pipe can be determined by releasing a known tracer gas within the pipe and monitoring its dilution. Similarly, the capture efficiency of the animal's breath can be determined by releasing a known tracer near the animal's mouth and nostrils as documented by a head position sensor.

In some embodiments, the system 700 may include a hardwired data analyzing station 713 in place of or to supplement station 701. Data from a remote feeding station may be transmitted via wireless or wired communication to the data analysis station 713. The hardwired data analyzing station 713, which may be a computer with a processor, I/O devices, a monitor, memory, and software (e.g., programs useful for providing the processing and other functions described herein), may operate to analyze and store the following data in local or remote memory or data storage: (i) ambient temperature; (ii) ambient pressure; (iii) relative humidity; (iv) wind speed; (v) time and date; (vi) $CH_4$ and $CO_2$ concentration over time (e.g., ambient and for individual animals); (vii) tracer gas type and amounts released; (viii) GreenCert or other carbon credit type information which may include, for example, data useful for a C-Lock Ruminant Module such as emissions baseline, change in emissions baseline, uncertainty, and incremental GHG reductions; (ix) animal identification through RFID technology; (x) animal body temperature; (xi) animal production statistics (e.g., beef statistics (e.g., current weight, gained or lost weight, rate of weight gain, estimate of future weight, feed efficiency compared to methane production, and $CO_2$ emissions per pound of gross animal weight) and dairy statistics (e.g., current milk production, increase or decrease of milk production, feed efficiency compared to methane production, and $CO_2$ emissions per unit of milk produced); (xii) animal genetics tracking (e.g., tracking and record of genetics bloodlines as it relates to methane production); (xiii) record of feed type and ration; and (xiv) formulation of future feed mixture and amount.

The system 700 may further include a data logger 714 on/near each of the feed stations 730 provided in the system 700 (e.g., the system 700 may include 2, 3, or more stations 730) or at another location in system 700. Each data logger 714 may function to record and store data such as: (i) ambient temperature; (ii) ambient pressure; (iii) relative humidity; (iv) wind speed; (v) time and date; (vi) $CH_4$ and $CO_2$ concentration over time: ambient and individual animals; (vii) tracer gas type and amounts released; (viii) animal identification through RFID technology; (ix) animal body temperature; (x) animal production statistics (e.g., beef statistics (such as current weight, gained or lost weight, rate of weight gain, estimate of future weight, feed efficiency compared to methane production, and $CO_2$ emissions per pound of gross animal weight) and dairy statistics (such as current milk production, increase or decrease of milk production, feed efficiency compared to methane production, and $CO_2$ emissions per unit of milk produced); and (xi) record of feed type and ration.

In some embodiments, the system 700 may further include a scale or other weight determination device 715 to determine and record individual animal weight (or pass the information to the data logger 714 for storing in memory or to the station 701, 713 for storage or processing). The scale 715 may be used to record gross weight of individual animals located at the feeding station 730. Some embodiments of the system 700 may also include an audio/visual indicator 716 (on the animal feeder 705 or elsewhere). The indicator 716 may be operated by the stations 701, 713 or by other control mechanisms to signal animals for feeding time or other events. Further, some embodiments of the system 700 may include a tracer gas release apparatus 717 in or near the animal feeder or hood 705. The release apparatus 717 may function (in response to control signals from the station 701, 713, a local controller such as in the analyzer 702, or the like) to release a tracer gas as a point of reference in measuring $CH_4$ and $CO_2$ by the analyzer 702 and/or data analyzing station 701, 713.

Figure 8:
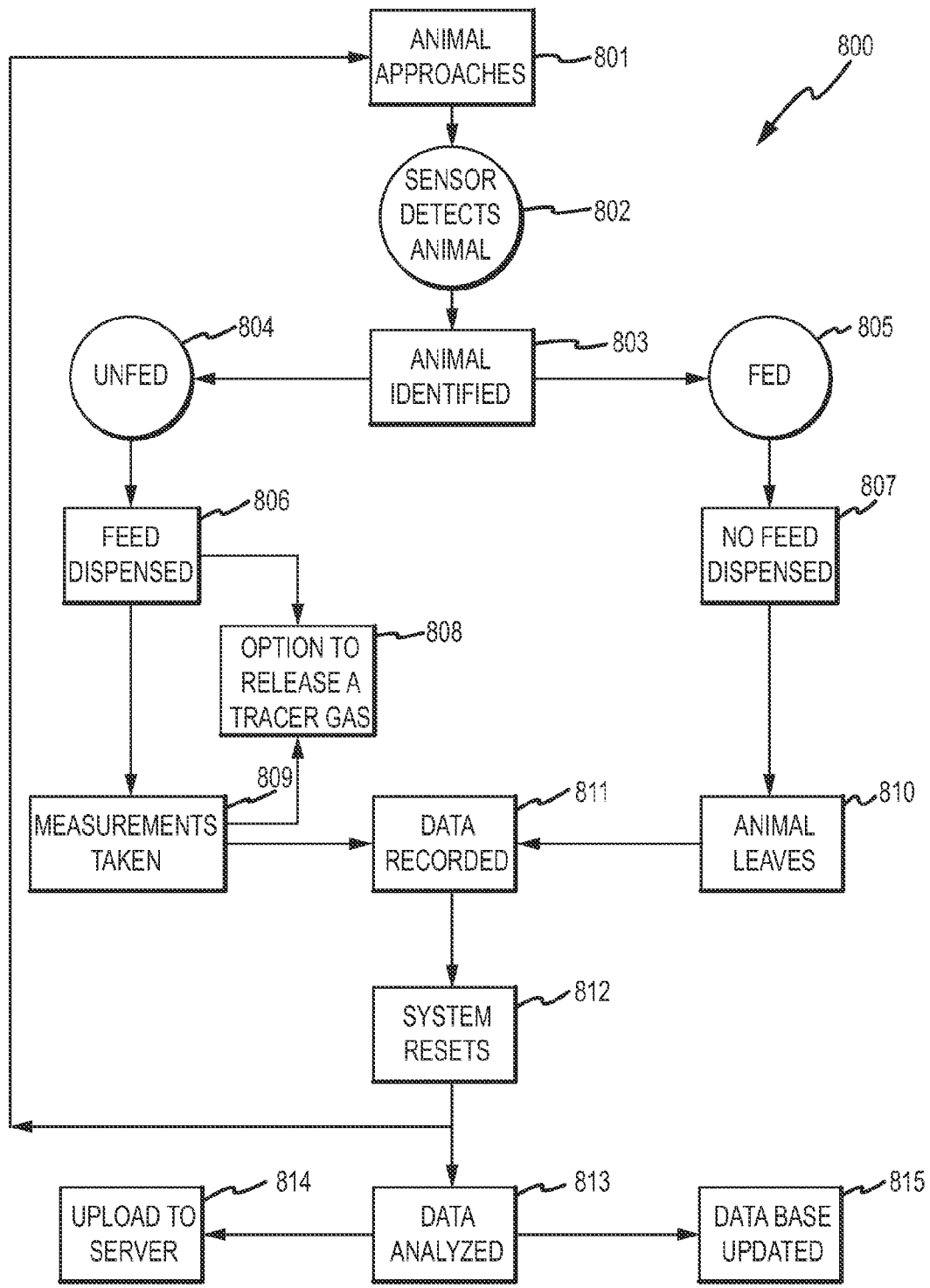
FIG. 8 illustrates a method of monitoring and controlling ruminant methane production and/or emission such as may be implemented, wholly or in part, by operation of the system shown in FIGS. 1-3, the system of FIGS. 6A and 6B, and/or the system of FIGS. 7A and 7B.

FIG. 8 illustrates a method 800 for monitoring and controlling GHG emissions (and other animal parameters in some applications) as may be practiced by operation of one or more of the GreenFeed systems described herein. At 801, an animal approaches a feed station or other monitoring location such as a stall or portion of an automated or other milking station/parlor. At 802, a sensor may detect the presence of the animal (e.g., a scale, a tag reader, a motion detector, or other animal detection device), and, at 803, the animal is identified such as by use of an RFID tag reader to read an ear or other ID tag on the animal. A look up may be performed for the identified animal to determine whether the animal has been fed at 805 or unfed at 804. If fed, the feeding or other monitoring station is not operated to dispense food/nutrients as shown at 807, and the animal later leaves as shown at 810. Data may still be recorded at 811 regarding the animal and their access of the monitoring station (e.g., their temperature, their weight, and other animal monitoring information discussed herein).

If at 804 it is determined that the identified animal has not been fed within a particular time period, a light may turn on and/or a tone may sound to alert the animal that they are eligible to be fed. At 805, the air sampling pipe and fan are turned on to pull air at a known flow-rate through the animal feed unit. When the animal inserts its head into the correct position as monitored by an infrared or sonic sensor or the like, a feed station or the like is operated at 806 to dispense feed. The feed may be chosen based on a prior breath analysis for the animal to try to control GHG production/emission or to control animal production. The dispensed feed, for example, may include a particular mixture of two, three, or more feeds and/or supplements that have been determined by a data analyzing station as appropriate for the identified animal in controlling their GHG emissions (or achieving an animal production goal such as weight gain, milk production, or the like). At 808, a trace gas release mechanism may optionally be operated to release a particular quantity of a known trace gas or gases for use in analyzing GHG in the animal's breath (as discussed in detail above). At 809, the feeding station, and its NDIR analyzer or other gas analyzing equipment, is operated to take measurements of the contents of the animal's breath including GHG emissions.

At 811, the measured data (and other animal data) may be recorded in a local data logger and/or after transmission to a data analyzing station. At 812, the feeding station resets 812 and awaits another animal. At 813, the method 800 continues with the data monitored at the individual feed or other station being analyzed by software/hardware provided at a data analyzing station (or locally at the feed station or other station in some cases). In step 813, the amounts of $CH_4$ and $CO_2$ may be determined for the animal along with ratios useful for determining which supplements and supplement/nutrient ratios may be used to control GHG production/emission by the animal. At 814, the data may be uploaded to a server (e.g., the data analyzing station, a server in a network with the analyzing station, or the like) and at 815, the database storing GHG and other monitored/analyzed data for each animal is updated to reflect the most recent feeding and monitoring of the animal with the collected/analyzed data being linked to the animal's ID (e.g., a record may be maintained for each animal with fields for each type of tracked information).

With the above description in mind, numerous other embodiments and particular implementations will be readily understood by those skilled in the arts. For example, it will be understood that the measurement device may be attached to any place where an animal congregates and mixing is restricted such as a passage way or a water fountain. In some embodiments, the system and/or method may be adapted to support calculating the methane and carbon dioxide flux from the decreases in concentration after an animal moves away from the feeder. In such cases, for example, the decay in methane and carbon dioxide concentrations may be used to establish a dilution factor that may be applied to the ratios to correct them for mixing.

In some implementations, the differentiation of metabolic carbon dioxide from ruminant carbon dioxide is tracked/measured so that these two processes can be quantified and differentiated. For example, in practice, when an animal is present (e.g., near a feed station, a milking stall/station, or the like), carbon dioxide from her breath will begin to immediately increase as she respires. Methane and carbon dioxide will likely both spike when an eructation occurs and carbon dioxide will likely reach an equilibrium concentration between breaths. The slope of the increase, corrected for mixing, then gives the metabolic (muscle) carbon dioxide. The spike includes this but is dominated by rumen methane and carbon dioxide, and in some implementations, the metabolic component may be subtracted to more accurately determine the rumen component. Note, methane in metabolic air results from methane produced in the hindgut, dissolved in blood, and exchanged with ambient air in the blood. This methane can be visible under optimal conditions in some GreenFeed applications.

Figure 13:
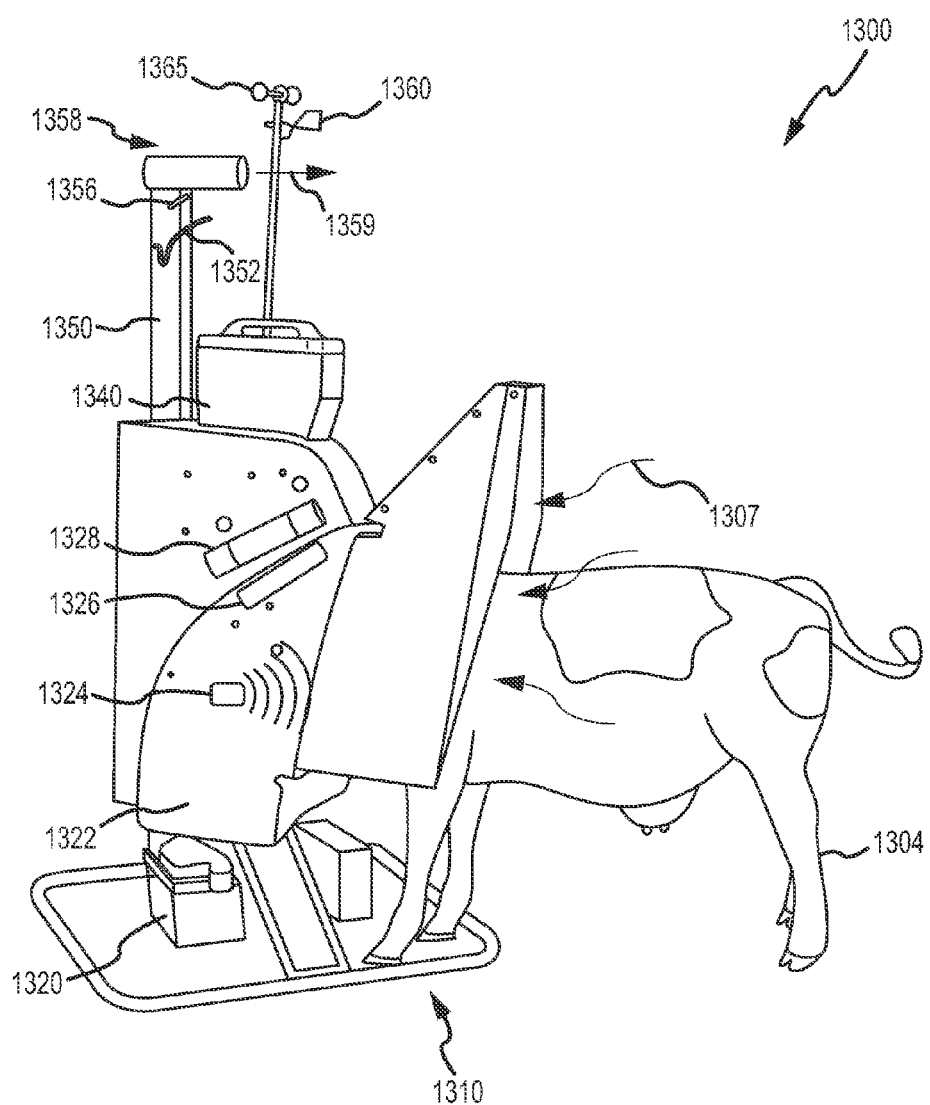
FIG. 13 illustrates another embodiment of a system for monitoring and controlling ruminant methane production/emission (or another embodiment of a GreenFeed system) such as may be used in a pasture or range for cattle or other ruminants.

In some embodiments, measurement of specific volatile organic compounds may be important or useful. For example, acetone may be utilized as a measure of acidosis. The inventor has made GCMS measurements of rumen gas and found it to contain a large number of volatile organics, any one of which could be an important marker for a specific process or condition and for which a dedicated sensor may be developed and/or included in the systems described herein. In some present embodiments or cases, the GreenFeed unit can include a system to conditionally collect a whole air sample in an appropriate container made of Teflon™ film or of specially-passivated stainless steel or in a specially-designed solid absorbent cartridge to provide a sample for later analysis in a research mode. In this case, the sample pump can be controlled by the computer so that it only samples conditionally when the animal's head is in the correct position. Alternatively, the system can be set to sample only when the animal's head is in the correct position and the methane detector is detecting an eructation. In this way, the sampling system can be controlled so that it only includes eructations or so that it only collects tidal breath samples and excludes eructations. A diagram of the GreenFeed conditional sampling system is shown in FIG. 13. Analytical instruments specific for specific gases of interest may be attached to the GreenFeed sampling tube. However, to support commercial viability, a less specific but much lower cost in-situ sensors may be developed and/or used. Further, it will be understood by those skilled in the arts that it may, at least in some applications, it will be useful to measure background methane and carbon dioxide in the air when the animal is not present in order to define the background concentrations present near the sensor. Such background measurements may allow these background concentrations to be subtracted from the elevated concentrations that occur due to the specific animal being measured to enhance accuracy of the described processes and systems.

In some embodiments it is desirable to utilize two NDIR instruments with different selectivities and sensitivities at the same time. Typically, one instrument will have a longer pathlength so that it is more sensitive, offset by a very narrowband filter so that it is more selective. The other sensor will have a shorter path length and a coarser filter. Therefore, it may have similar sensitivity, but it will be less selective for methane. Utilizing these two sensors simultaneously allows a potentially-interfering tracer such as propane to be used and since each detector has a different sensitivity for propane, the potential interference can be mathematically eliminated (e.g., this results in two equations with two unknowns, so the interference equation is solvable). This system offers the additional advantage that if the cows are producing VOCs that could potentially interfere with methane quantification, the responses of the two instruments will diverge and the condition will be quickly noted.

With the above understanding of systems and methods understood, it may be useful now to further discuss exemplary GreenFeed systems including those with data analysis tools (which may be web-based or network-based) to allow users (such as dairy operators) to view and manipulate data produced by the GreenFeed system. In the following discussion, a number of specific tests and field experiments that have been performed by the inventors will be discussed as these are believed useful for further explaining monitoring methods and techniques for adjusting feed and/or supplements to reduce GHG emissions and/or to increase ruminant growth or production levels and/or to monitor animal health.

Figure 9:
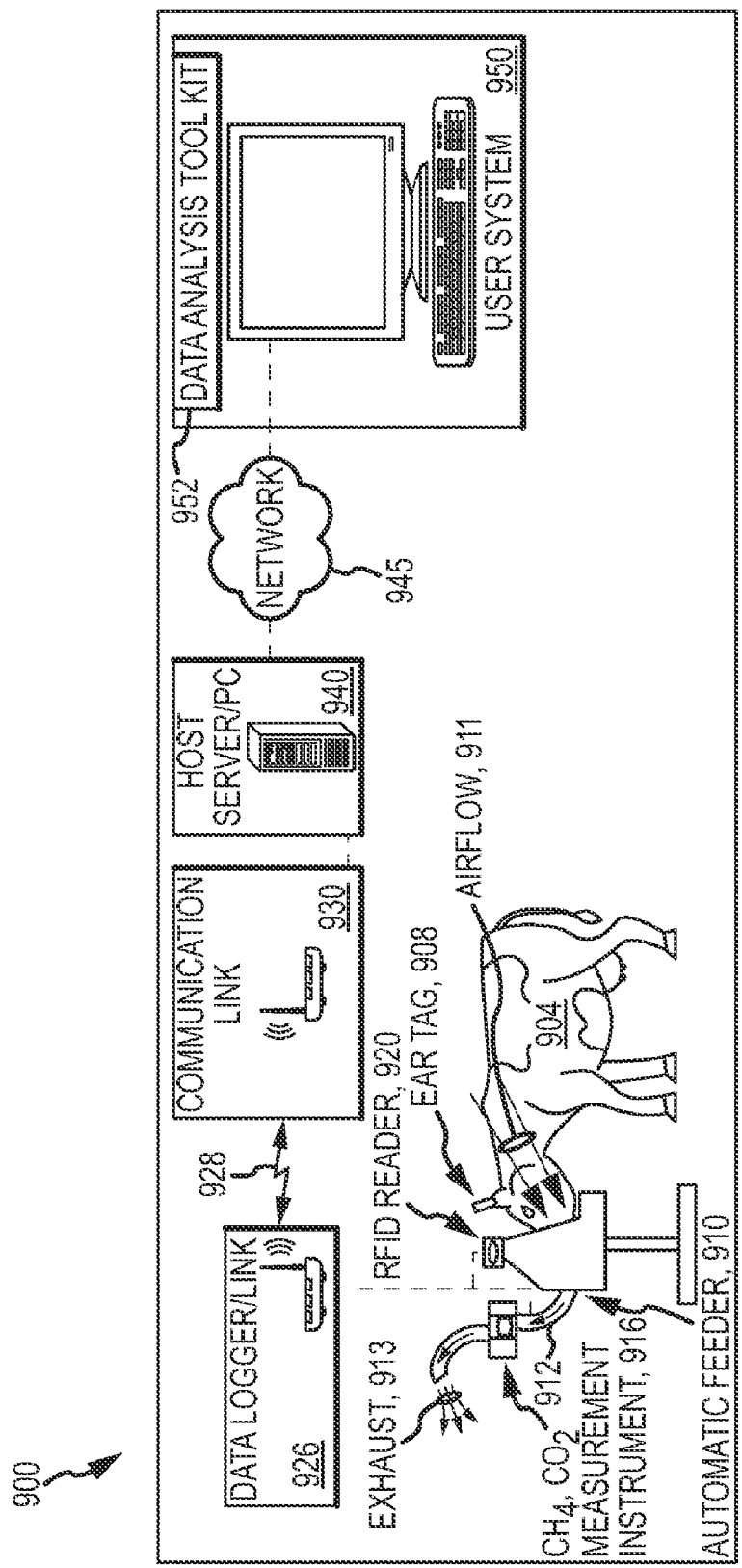
FIG. 9 illustrates schematically another representative GreenFeed system of the invention.

For example, FIG. 9 illustrates a GreenFeed system 900 in a schematic or functional block form. The GreenFeed system 900 is useful for monitoring methane and carbon dioxide emissions from a ruminant such as a dairy cow 904. The GreenFeed system 900 includes an automatic feeder 910 with a hood/manger for receiving the head of the ruminant 904 such as via an opening or hole through which airflow 911 may be drawn during feeding (and breath monitoring operations). The ruminant 904 has been tagged with an identifier such as an ear tag 908 with an RFID chip, and the GreenFeed system 900 includes an RFID or ID tag reader 920 for interrogating the tag 908 to retrieve information pertaining to the ruminant 904 (such as an identifier or code assigned to the ruminant which allows its monitored data to be linked to the ruminant and to allow supplement and feed information for the ruminant to be tracked and later retrieved/updated).

The Greenfeed system 900 also includes an exhaust or outlet plenum 912 through which airflow 911, which includes the breath of the ruminant 904, is drawn out, filtered, and exhausted at 913. As shown, though, the sampled or exhausted air 913 (which includes the ruminant-expelled gases) is passed through (or is processed during flow by) a measurement instrument 916 such as one configured to determine levels or concentrations of $CH_4$ and $CO_2$. These concentration data along with capture efficiency data and flow-rate data are used to quantitatively determine metabolic gas mass fluxes. The data gathered by the RFID reader 920 and the measurement instrument 916 may be logged or stored by the data logger 926 at the gathering site. Then, the data logger/communication link 926 may operate to wirelessly transmit all or portions of the gathered data 928 to a communication device/link 930 associated with a GreenFeed host server (computer system) 940 that is adapted to provide the data analyzing station functions described herein.

Further, there may be many applications where it is desirable for a user such as a cattle rancher, dairy farmer, or the like to be able to remotely monitor their herd or ruminants. To this end, a user computer system or network node 950 may be included in the GreenFeed system 900 to allow a user to operate their system/node 950 to access the host server 940 via a digital communications network (such as the Internet). The user system 950 may use their web browser to access a website hosted by the server 940 and/or use a data analysis tool kit 952 running on their system 950 to process data downloaded from the host server 940. Examples of data processing that may be performed by the host server and/or the data analysis tool kit 952 are described in detail below, and the following discussion also provides a number of graphs and/or screens that may be provided to or generated by the user system 950 (e.g., displayed on a monitor with use of their web browser and/or the data analysis tool 952).

The GreenFeed system 900 may be tailored to fit unique and very specific needs for individual operators, for example, operators across the cattle and dairy industries. It allows farmers or operators to measure methane emissions from individual cows 904, which may be significant as tests have shown that certain individual cows within a same herd (and that are similarly fed) may emit up to 40 percent more methane than others in the herd. The GreenFeed system 900 allows farmers to identify changes in methane emissions from their herd (average levels or cumulative amounts) and/or for individual ruminants over time. This is especially useful to monitor animal health and to provide an early indicator of illness or disease. It also allows users to measure baseline performance (e.g., without supplements or changes in diet) and then monitor the changes in emissions as management changes are implemented (e.g., with one, two, or more supplement mixes, with differing diet changes, and so on), which may be particularly useful in projects aimed specifically at reducing methane emissions. The GreenFeed system 900 also can be used to determine when their pasture food (or other food supply) has undergone a change in quality (e.g., the methane to carbon dioxide ratio has declined indicating a lower quality pasture food source).

The GreenFeed system may be used to measure, with instrument 916, $CH_4$ and $CO_2$ emitted from the mouth of the cow 904 during discrete sampling periods. For example, with use with dairy cattle, samples may be taken while a cow 904 is milking, two or three times per day. When used with other animals, a sample may be analyzed at a feeding or watering station at timed intervals. The required or desired sampling intervals typically are dependent upon specific management variables. For example, it may be adequate with continuously-fed animals to use an aggregate sampling time of fifteen to thirty-five minutes per day so as to define emission profiles and changes for individual dairy cows (with these calculations/determinations performed by software on the host server/PC and/or the data analysis tool kit 952 (e.g., with web-based emission analysis software)).

The GreenFeed system 900 layout may be easily modified for specific locations based on the existing infrastructure and site-specific requirements. For example, in dairies with automatic milking robots, the $CH_4$ and $CO_2$ sensor(s) may be installed in the robots such that a separate feeder/hood is not required in the system 900. Specific data links (provided by link 926, link 930, and the like) and server requirements (provided by server 940) may be easily integrated with existing software or supplied as useful for a particular implementation. The data analysis toolkit 952 may be configured to provide a user-friendly web-based data analysis tool that allows a user operating the system 950 to examine the gathered and processed/generated data and to track the performance (e.g., performance achieved or found for each monitored animal) from any location (e.g., any location with a connection to Internet 945).

Figure 10:
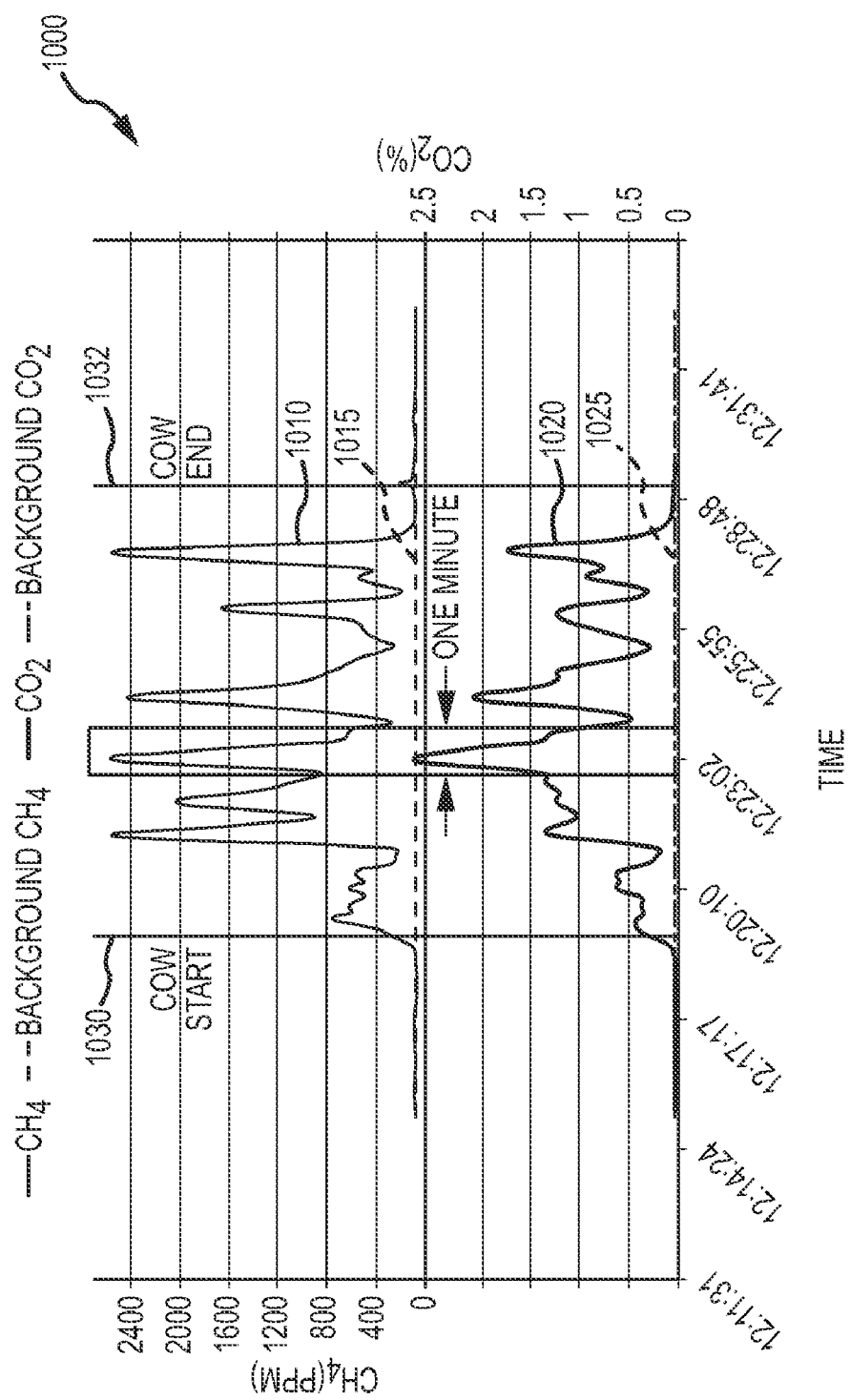
FIG. 10 illustrates a graph of monitoring results obtained during operation of a GreenFeed system, such as that shown in FIG. 9, to monitor methane and carbon dioxide emissions from a dairy cow.
Figure 12:
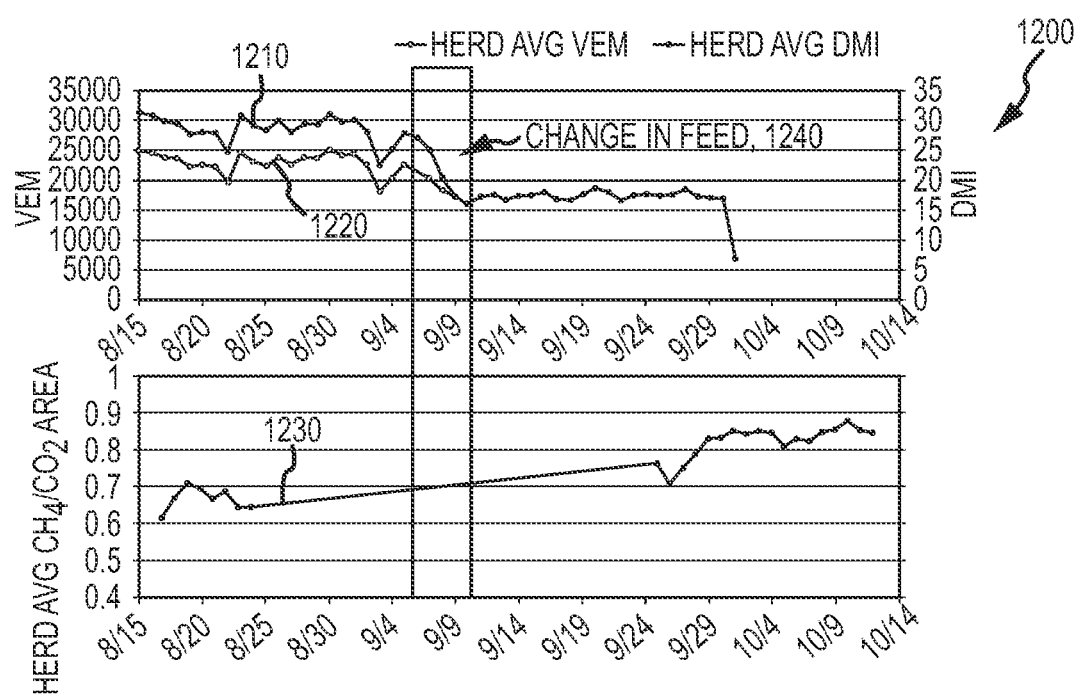
FIG. 12 is a graph plotting dry matter intake (DMI), caloric intake (VEM), and methane to carbon dioxide ratios for a herd over time to illustrate how management of feed can be used to vary and control methane production.

FIGS. 10-12 provide results in graph and tabular form that were obtained from a study completed with a GreenFeed system (such as system 900 of FIG. 9) placed in a dairy. In this study, the GreenFeed system instruments were installed in a milking robot. $CH_4$ and $CO_2$ emissions (breath plus eructations) from each cow were automatically collected during milking. The milking times ranged from 5 to 15 minutes and occurred two to three times per day. No major maintenance or adjustments were required for the GreenFeed system over the course of the test.

FIG. 10 illustrates a graph or plot 1000 illustrating typical measured values with the $CH_4$, $CO_2$ measurement instrument over time. In the plot 1000, the cow entered the robot or milking started at the time shown by line 1030 and the cow left the robot or milking ended at the time shown by line 1032, which in this example was about 9 minutes. Line 1010 illustrates typical measurements of raw $CH_4$ with line 1015 showing background levels, and line 1020 illustrates typical measurements (concurrently taken with the $CH_4$) of raw $CO_2$ with line 1025 showing background levels. As shown, each peak of the $CH_4$ and $CO_2$ corresponds to an eructation event for the cow and lasts about 1 minute.

FIG. 11 provides a table 1100 of the daily averaged $CH_4$/$CO_2$ ratios for a set of 14 cows over a 54-day study at the dairy. As can be seen, the cows to the left in the table 1100 have higher ratios, which show that the ratios of $CH_4/CO_2$ may differ significantly within a single herd of animals being fed and otherwise treated similarly. In this test "Cow 1" was 38 percent higher than "Cow 14" on average. The effect of a change in feed is also shown by the data of table 1100 as the feed was changed between Day 7 and Day 40.

FIG. 12 provides a graph 1200 that plots dry matter intake (DMI) with line 1210 over time and also plots caloric intake (VEM) with line 1220. To allow the effect of changes in the DMI and/or VEM on methane to be monitored, the graph 1200 also plots values for the herd average $CH_4$ to $CO_2$ ratio over the same time period (and for the same monitored herd). Also, the plot shows where a change in feed occurred at 1240 to allow an operator of a GreenFeed system to readily identify effects of changes in herd management on the $CH_4$ to $CO_2$ ratio. As shown for this set of test data, the herd-averaged $CH_4/CO_2$ ratios increased when feed was changed (i.e., DMI and VEM were decreased at 1240). The results of the operation of the GreenFeed system shown in graph 1000, table 1100, and graph 1200 show that the system (such as system 900 of FIG. 9) may be used to effectively monitor $CH_4$ differences and trends over time. The information output by the GreenFeed system can be used by a farm operator to achieve higher feed efficiencies, lower greenhouse gas emissions, and higher profits.

In general, the GreenFeed system may be thought of as including an instrumented feeder station that measures real time $CO_2$ and $CH_4$ emissions from ruminant's nose and mouth such as a dairy cow's nose and mouth. A GreenFeed system may include an RFID or other identification system to identify individual animals such as particular cattle in a herd for monitoring and for control of feed and supplements to that particular animal. Each GreenFeed system may include a software tool(s) that functions to record and analyze specific ruminant's $CH_4$ and $CO_2$ emissions and other available process parameters (e.g., time of day, animal weight, animal temperature, and so on). One design goal of a GreenFeed system is to provide a cost effective tool and method for farmers and ranchers to use in monitoring the health and in managing the feeding and production of their ruminant herd.

Expanding upon the above-discussed study performed at a dairy, the dairy used an automatic milking robot that allowed the cows to milk on demand. Each cow was fed a uniquely tailored blend of food and concentrate (supplements), with "continuous" feed over the day. The following data was collected for each cow: (a) milk volume (per milking period); (b) cow weight (per milking period); (c) daily food intake (e.g., DMI, VEM, food mixture by weight (such as Type 1, Type 2, Type 3, Type 4, Type 5, and Type 6), and concentrate weight (Type A ... Type E or the like)); (d) calving date for each cow; and (e) $CO_2$ and $CH_4$ emission as measured/determined with the GreenFeed system instruments.

Regarding $CH_4$ and $CO_2$ emissions measurements during the dairy test, a $CH_4$ and $CO_2$ sampling probe was placed or positioned in the robot to be near the cow's nose when a cow was using a feeding trough of a milking robot. In this test, the $CH_4$ and $CO_2$ sensors were sensors available from Madur Electronics of Vienna, Austria. $CH_4$ and $CO_2$ instruments were operated to measure concentrations on a one-second basis, 24 hours per day, including during each milking period and also while cows were not present to obtain background levels for these gases. The GreenFeed generated and stored records of each cow visit to a milking robot, with entrance and egress times documented, and this allowed measured emission concentrations to be correlated with or assigned to specific cows within the dairy's herd. During the test, 25 days of emissions measurements were obtained for 39 different cows, with 26 of the 39 cows remaining in the study for the entire period.

As discussed above, FIG. 10 provides a graph 1000 plotting exemplary $CO_2$ and $CH_4$ concentrations that were measured for a milking period during the test. The GreenFeed system included data analysis software that calculated background concentrations of $CH_4$ and $CO_2$ (see lines 1015 and 1025 in graph 1000), and these concentrations were found to change over the test period (e.g., a fixed background level typically should not be assumed or used in $CH_4$ and $CO_2$ calculations). The GreenFeed system then calculated the areas under the $CH_4$ and $CO_2$ curves for each milking period (i.e., area under line 1010 between start 1030 and stop 1032 and area under line 1020 between start 1030 and stop 1302 in graph 1000). For example, the methane area would be a summation over the milking period of: $\Delta_{time}*(CH_{4Avg}-CH_{4Background})$, where $\Delta_{time}$ may be 1 second, $CH_{4Avg}$ is the average concentration of methane, and $CH_{4Background}$ is the background concentration of methane. A similar area calculation is used for carbon dioxide. Then, the ratio of the $CH_4$ and $CO_2$ areas was calculated such as on a daily averaged basis for each cow (with 1 to 3 milking periods). While not performed in the test, it is expected that many implementations of the GreenFeed system will also measure/determine the mass flux of $CH_4$ and $CO_2$.

With reference to FIG. 10 and graph 1000, it may be noted that normalizing $CH_4$ by $CO_2$ concentrations and trending over time is a useful practice if certain assumptions are made. First, such normalizing assumes that changes in respiration rates over time are small when compared with changes in rumen $CO_2$. Second, from the test and graph 1000, respired $CO_2$ appears to be relatively small in magnitude when compared to the $CO_2$ released from rumen as measurements show clear $CO_2$ peaks from each eructation. Third, it was determined in the test that $CO_2$ and $CH_4$ background concentrations typically will vary enough (e.g., one to two tenths of a percent variation or more over time) during monitoring by a GreenFeed system that it is desirable to process monitored data taking into account these background level changes.

At this point, it may be useful to further discuss results of the data analysis provided by the GreenFeed system in the performed test. FIG. 12 provides a graph 1200 that may be generated by the GreenFeed system and displayed (or output) to a user computer system (e.g., in a GUI on a monitor) communicating with the GreenFeed host server. The graph 1200 plots daily herd methane to carbon dioxide ratio averages over time. A change in feed occurred at time 1240, and, in the test, the change in feed was from a corn/grass mixture to a grass/alfalfa mixture. As shown with graph 1200 and line 1230, the most significant occurrence relative to $CH_4/CO_2$ ratios was the change in feed at 1240 as the $CH_4/CO_2$ ratios increased 24 percent after the feed was changed. The particular feed change is not as significant for the GreenFeed system as is the effectiveness in monitoring the $CH_4/CO_2$ ratios over time to determine the effect of feed types and mixtures (which often will include supplements to control methane emissions and/or increase production).

As shown with table 1100 of FIG. 11, the GreenFeed system and its data analysis system/software may be used to track for each individual cow of a herd (or a monitored subset) the methane to carbon dioxide ratio over time. In table 1100, the data was sorted such that the cows with the higher ratio values (by average) were placed to the left such that the average ratios increase from left to right. Again, this data is useful for showing a dairy operator that ratios may vary greatly among cows (which may be an indicator of a genetic factor that may be used over time to reduce methane emissions or increase herd productivity). Also, the table is useful for showing that the herd average ratio significantly increased with a change in feed (in September in this test), which is useful for providing readily understandable data for use in selecting feed and feed quality to obtain desired results.

The data analysis system may also be used to provide a variety of other graphs, plots, and data as its output such as for display in a GUI or screen of the user system 950 in GreenFeed system 900 (e.g., via operation of the data analysis toolkit 952). For example, the toolkit 952 may operate to produce or display a plot of the methane to carbon dioxide ratios versus caloric intake or VEM. Such a plot was provided during the above test and provided herd average ratios versus VEM by date (e.g., the ratio for a day was plotted versus a VEM average for the herd for a day). Such a plot may be useful as it links the effect of changes in VEM over time to changes in the methane to carbon dioxide ratios. In the test, for example, this plot indicated graphically or visually that the ratios increased with a food switch.

Similar or different plots may be provided on a cow-by-cow or animal-by-animal basis. For example, the test included operating the GreenFeed System to output graphs that plotted the methane to carbon dioxide ratios versus DMI (over time) for specific cows. In the test and with the change in feed, there were no positive slopes found (or all were negative slopes over time). The GreenFeed system may be well suited for determining the effect of changes in feed supplements, and the system may be used to plot methane to carbon dioxide ratios for the herd (or for a particular cow) against amounts or amounts of a particular concentrate or supplement.

In the test, herd ratio values were found to decrease with increases in a first type of supplement but increase with increase with a second type of supplement (although this second finding may have been obscured or altered by the concurrent change in feed). Plots may also be provided for differing types of food supplement rather than simply increasing amounts of the supplement. In other words, the ratios may be determined for a cow or for a herd and the supplement and/or the feed makeup may be changed based on the determined ratios (e.g., try a first supplement, increase or decrease its amount to achieve a desired ratio, try a second supplement, increase or decrease its amount to achieve a desirable (optimized ratio for the supplement), and then choose which of the two supplements is preferable and deliver at the amount that provides the optimized ratio).

In the study, the GreenFeed system was also used to provide a graph plotting the methane to carbon dioxide ratios versus VEM with each point in the graph representing a different cow and its study period averages. This plot was used for "normalizing" for the food switch by averaging each cow's daily emissions and VEM over the trial or test period. The relationship of $CH_4/CO_2$ to VEM when comparing cows was different than the relationship for the same cow over the trial or test period. This plot showed that the cows that ate more were less efficient in terms of $CH_4/CO_2$ ratios, which may be a useful factor to consider in managing a herd using a GreenFeed system. Further, the GreenFeed system was also used to monitor what occurred with cows in the days or period following calving. This tracking involved graphing the daily $CH_4/CO_2$ ratios for these cows in the days following calving, and also graphing the milk production for this same time period. In this test, the $CH_4/CO_2$ ratios were found to decrease over time after calving. This is yet another example of the type of information that can be readily provided with the GreenFeed systems due to the ongoing measurement of methane and carbon dioxide levels for each cow.

To summarize the results of the dairy-based test of the GreenFeed system, the instrumentation and software/hardware-based processes functioned as expected (and as described above with reference to FIGS. 1-12). The instrumentation produced reliable $CO_2$ and $CH_4$ concentration measurements over the study period with minimal human interaction. The determined ratios of $CH_4/CO_2$ varied as much as 38 percent between individual cows with some cows producing consistently higher ratios and others producing consistently lower ratios (which may encourage breeding of particular cows to provide a more desirable herd with relation to methane emissions). For the herd, the $CH_4/CO_2$ ratios increased by about 24 percent and VEM decreased by 29 percent for the same time period when the food source and amount was changed. According to test results, cows that ate more feed were less efficient in terms of gas production (e.g., higher $CH_4/CO_2$ ratios). In the days following calving, the $CH_4/CO_2$ ratios were affected. Significantly, changes in $CH_4/CO_2$ ratios seem to be strongly or directly related to changes in VEM and DMI, and there are also effects from concentrates/supplements and feed type.

The following is a further explanation of the GreenFeed system including discussion of its uses and advantages. The following explanation then discusses additional embodiments of the feed/monitoring stations that may be used in a field (e.g., a standalone, automated feeder and monitor for use with cattle or other similar ruminant operations) and in a dairy setting (e.g., in a milking station or robot to provide feed/supplements and monitor gas emissions during milking). The explanation also discusses data that may be gathered and processed and exemplary screens that may be provided to a user through use of the GreenFeed system.

The GreenFeed system provides components that operate in conjunction to monitor the metabolic gas composition of animals in a cost-effective, non-intrusive way. Its design and measurement capabilities may be tailored to the measurement of metabolic gases emitted from ruminants. For example, the GreenFeed system may be optimized to quantitatively capture the breath of cattle and to analyze the emitted gasses for trace constituents including methane ($CH_4$), carbon dioxide ($CO_2$), and water-vapor. As a result, the GreenFeed system provides an important tool for research scientists as well as for those responsible for the husbandry of animals, especially ruminants, because it provides data that allows scientists and producers to remotely monitor trace gas emissions, with a high time-resolution in near-real time, from a large number of individual animals. The trace gas composition and flux rates are important and useful for monitoring because they can reflect or directly indicate changes in the animal's physical and biological condition. This can lead to improved animal health, higher feed efficiency, lower GHG emissions, increased production and lower costs to operators and to society.

Consumptive, digestive, excretive, assimilatory, and dissimilatory processes are immediately reflected in the composition of emitted metabolic gases that is determined by the GreenFeed system. For example, ruminants emit $CH_4$, almost all from the head-end of the animal. The emission of $CH_4$ represents an energy cost to ruminant animals. Ruminant production rates of $CH_4$ and $CO_2$ as well as rumen emission ratios of $CH_4$, $CO_2$, and other trace gases are calculated by the system to provide important diagnostic data with respect to animal health, as well as data to help determine each individual animal's or group of animals' production (for example meat, milk and calf production) efficiency. Periodic monitoring of $CH_4$ and $CO_2$ gas emission ratios and fluxes via use of the GreenFeed system can potentially provide data which can be combined, by the GreenFeed system or by the user of the system, with other routine measurements (for example, animal weight gain, feed composition, milk production, core body temperature, and the like) to track dry-matter intake, changes in rumen function, and changes in aerobic respiration due to changes in animal activity for each individual animal. As will be appreciated, the emissions data can be combined with other data sources to better understand the condition of each animal and to monitor any changes that have occurred over time.

Measuring and understanding $CH_4$ and $CO_2$ emissions could potentially be beneficial for a number of purposes. For example, use of the GreenFeed system to monitor gaseous emissions and to modify feed or supplements (or taking other management actions) may translate into efficiency improvements, early disease detection, more certain estrus detection, improved animal health indicators, and reduced $CH_4$ emissions. The GreenFeed system monitors the composition of the metabolic gases emitted from ruminant animals to track and more quickly identify optimal strategies that reduce $CH_4$ losses and improve efficiency. Before the availability of the GreenFeed system, it had been impossible to monitor emitted metabolic gases without extensive laboratory and analytical facilities, skilled technicians, and intrusive animal handling facilities.

With regard to FIG. 13, the GreenFeed system 1300 includes the following components. First, the system includes a "station" 1310 (such as a hood or manger or the like) where an animal is likely to voluntarily visit or a place where an animal can be attracted or placed for several minutes during a day. The "station" 1310 may be, as shown, a feeding station that supplies feed or a mineral or other supplement. Alternatively the "station" 1310 could be a water fount where the animal approaches to get a drink.

The "station" 1310 may be designed to minimize mixing of the animal's breath with the atmosphere; however, atmospheric air 1307 is also entrained into the system or station 1310 and dilutes the emissions of a visiting animal 1304. The GreenFeed "station", chamber, hood, or manger 1310 is designed so that turbulent mixing is minimized. The system 1300 does not require an air-tight seal as is attempted with a respiration chamber or a bag or chamber placed over the animal's head. The GreenFeed system 1300 works by attracting an animal 1304 to place its head into an apparatus 1310 shaped specifically to minimize the dead volume of the apparatus and to reduce turbulent mixing with ambient air. In one example, the opening of the station 1310 is large enough to accommodate the animal's head.

In the GreenFeed "Rangeland" unit or embodiment of the manger or feeding unit 1310, the unit is roughly wedge-shaped. As the animal 1304 approaches, its body helps to block the opening of the wedge. Therefore, when the animal 1304 continues to move forward to reach the reward (e.g., feed, supplement, water, or other attractant), its shoulders and head somewhat block the opening of the station 1310. Further blocking could be accomplished with flexible side-curtains of a flexible plastic or rubber material or with a device such as an air-curtain, similar to those used to minimize mixing in building openings. The wedge or station 1310 can also be designed so that it is able to pivot into the wind. Therefore, air flows smoothly toward the point of the wedge and over the top and sides of the animal 1304.

In some applications, a fan or air pump 1358 is used to pull a quantified amount of air 1307 over and around the animal's head through an inlet and through a sample manifold consisting of a series of inlet plenums or of a single inlet plenum connected to a central sample pipe 1350 and for output into the atmosphere as shown at 1359. Primarily, samples are routed through continuous analytical instruments to measure metabolic gas concentrations real-time (such as with $CH_4$ and $CO_2$ sensors 1322, which are positioned in hood/station 1310 and powered by batteries or a solar power supply 1320). In addition, air samples can be collected from the pipe 1350 via sample port 1356 for later analysis from individual animals or the aggregate for the herd.

In one application of system 1300, the instruments 1322 include non-dispersive infra-red analyzers for $CH_4$ and for $CO_2$ for continuous gas measurements. Additional analytical instruments could be included to measure concentrations of a wide range of trace gases. Additional measurements could include ambient air wind speed with device 1365, wind direction with device 1360, relative humidity with device 1359, the direction that the GreenFeed station 1310 is facing with respect to wind direction, the temperature and humidity of the air in the sample pipe 1350, and other measurements (with device 1359) that can be used to determine the mass flow of air through the sampling system and the dilution that occurs due to mixing with ambient air 1307.

A tracer can be incorporated into the station 1310 via tracer compartment 1328 so that when an animal 1304 inserts its head in the correct location as indicated by an infra-red proximity, an ultrasonic sensor, or other sensor 1324 designed to indicate the position of the animal's head inside the station, a trace gas is released near the animal's nostrils. The resulting tracer concentrations are then measured in the collection pipe 1350. Thereafter, the same trace gas flow is inserted directly into the collection pipe 1350 and measured. The ratio of concentration of the release near the animal's nose compared to that inserted into the collection pipe 1350 can be used to calibrate the capture rate of the animal's breath when it is utilizing the GreenFeed system 1300. In one example, propane is used as a tracer. When propane is used, a cartridge containing an odorant scrubber is inserted so that the odor does not distract animals using the GreenFeed unit. However, other gases such as butane or $CO_2$ could also be used. The flow of the tracer can also be modulated so that the tracer signal can be differentiated from the emission of $CH_4$ and $CO_2$, although the $CH_4$ sensor 1322 may also respond to propane.

In another example, a separate sensor that only responds to the tracer gas is used. In a third example, two sensors 1322 that respond to $CH_4$ but have different responses to the tracer gas can be used to differentiate the tracer from the $CH_4$ emitted by the ruminant. In this case, the data is plugged into two separate equations with two unknowns. In other applications, a chemical filter can be used to differentially remove the tracer gas at periodic intervals so that both the tracer and the $CH_4$ emitted from the ruminant can be calculated. In another example, $CO_2$ can be used as the tracer and released at intervals that differ from the release intervals of the animal and therefore the release frequency is modulated so that the tracer signal can be identified and removed from the animal emission signal.

Data are collected on a local data logger or computer or transmitted to a remote computer. Data transmission can utilize an internet connection, cell phone connection, a wireless internet connection, or connection with low earth orbiting communications satellites. Data processing can be all or partially completed on site using computing systems in residence in the GreenFeed unit 1310 or the raw data can be stored on site and periodically transmitted to a remote computing facility or any combination of the two schemes.

Computer software is used to analyze the data and to flag data that might be uncertain because of animal head position, wind speed, wind direction, excessive mixing, or other problem detected by the GreenFeed instrumentation. Software modules are designed to operate the GreenFeed unit, monitor operational variables and collect data from all sensors. Additional software modules to process data, to display the data to users, and to interface with users in an intuitive way has also been designed. A GreenFeed control interface allows remote operation of the GreenFeed system through a computer with an internet connection, or in addition through a "smart" cell phone capable of connecting to the internet. Alternatively, data could be stored on media local to the GreenFeed unit for periodic collection and or download.

The GreenFeed system can be powered by line electric power. Alternatively, the GreenFeed system is powered by two 12-Volt deep-cycle batteries 1320. The batteries 1320 can be recharged from line current, or in one example, the batteries are recharged via a solar panel (not shown in FIG. 13). In one example, the GreenFeed system collects sensor data at a resolution of approximately one second. The station 1310 includes an RFID sensor 1326 for reading a tag on the animal 1304 such that the animal identification information can be logged and/or sent to a data analysis station to allow the gas monitoring and other monitored data to be linked to particular animals 1304. Additionally, the station 1310 includes a feed bin 1340 that may be automated to dispense feed and/or supplements of a particular amount and type to suit the identified animal 1304 (e.g., feed and/or supplements provided by type and amount in response to previously tracked gas emissions such as methane to carbon dioxide ratios or other monitored information).

In some embodiments, the GreenFeed system is tailored to take advantage of, or to create specific locations where animals voluntarily visit, periodically throughout the day, for a period of minutes during each visit so that quantitative measurements can be made of emitted metabolic gases. In the following example, the GreenFeed system includes an automated feeder that attracts the animals. However, as discussed above the GreenFeed system may also be incorporated into a milking robot, and a unit based on the same principles and instrumentation can readily be adapted to work in conjunction with watering facilities such as troughs and founts.

While the animals are at the feeding station (or the milking station or other location), ambient air is drawn past the animal's nose at a measured, specified flow-rate and through a sampling plenum or sample manifold into a sample collection pipe. A subsample of this gas is routed to gas analyzers capable of continuous analyses. Alternatively, the subsample could be conditionally routed into a sample collection device for later analysis of trace gases in a laboratory. That is, the computer can control the gas sampling system based on independently monitored variables. For example, gas samples may be collected only during eructations or, alternatively, gas samples can be collected only in the absence of eructations. In one example, air is drawn over the animal and past the animal's head and nostril region at a rate of about 100 cubic feet per minute through an air sampling manifold or air sampling pipe fitted with an air pump or exhaust fan. From this pipe, air samples are drawn through instruments. For example, NDIR (non-dispersive infrared) instruments that are capable of continuously analyzing the trace gas concentrations flowing through the pipe at a resolution of about one second may be used, but other analytical instruments based on other principles of operation could also be used. The flow rate through the pipe and the mixing with ambient air are designed to create mixing ratios that are optimal for the specific instruments chosen for measurements. In the example described above, the mixing ratios of $CH_4$ typically range from 1 part $CH_4$ per 1,000 parts air while $CO_2$ ranges from 1 part $CO_2$ per 200 parts air. These values are high enough so that in most cases, background concentration variations do not greatly influence the measurements from individual animals.

Additional sensors that can be used in the GreenFeed System include solid-state sensors to measure trace gases such as $CH_4$ or volatile organic emissions, to measure other trace gases such as acetone or hydrogen sulfide, or to measure other trace metabolic gases of interest. In one embodiment, a sensor is included specifically to monitor the tracer gas that is released into the GreenFeed unit close to the animal's nostrils. In one example, the flow rate of the trace gas can be accurately set using, for example, an accurate gas pressure regulator and a flow-control valve. The change in weight of the trace gas container can be accurately measured over a specified time interval. From this data, the mass of tracer released per unit time can be accurately determined, and the mass of tracer collected into the sampling pipe can also be calculated from the instrument responses. From this data, the "capture" rate of gas that is pulled into the collection pipe can be calculated.

In another example, the tracer release rate does not have to be known exactly, and it is constant over time. In this case, the tracer is released near the animal's nostrils, when the proximity detector indicates that the animal's head is in the correct position to collect a sample of the metabolic gases emitted by the animal. Periodically, the tracer release is switched so that it is released inside the collection pipe. The ratio of the two values can be used to quantify a capture rate of the animal's emissions, and the mass emission rate of the tracer does not have to be known. In one example, the tracer does not have to be released for each animal. Rather, the capture rate measured other animals under specific conditions can be used to accurately estimate the capture rate of an animal under similar conditions. From this data, the numerical relationships can be established to predict capture rates without the tracer release for all of the animals. External sensors can also be added at a station including a sensor to detect wind speed and direction and an external (ambient air) moisture sensor. The GreenFeed system implements a number of independent methods, each with independent uncertainties that when combined ensure that the uncertainties in flux measurements are minimized. The GreenFeed system is also designed to obtain uniform flow measurements and also to obtain well-mixed, representative analytical measurements.

In addition to real-time analysis of trace gas concentration in the collection pipe, in one configuration, subsamples of gases are collected from the air flow pipe and stored in containers such as stainless-steel canisters or Teflon® or Tedlar® bags for further analysis by appropriate analytical instruments such as gas chromatographs equipped with flame ionization detectors to measure $CH_4$ and other volatile organics. The subsample is conditionally routed into a sample collection device for later analysis of trace gases in a laboratory. That is, the computer can control the gas sampling system based on independently monitored variables. For example, gas samples may be collected only during eructations or, alternatively, gas samples may be collected only in the absence of eructations. In another configuration, samples are collected directly from the air flow pipe and analyzed directly, without sample containers, by gas chromatography, mass spectrometry or other appropriate analytical instruments.

With ever-changing wind currents and movement of the animal's head, the ratio of the ruminant animal's breath that travels up the air-flow pipe compared to the ratio that is mixed into background air or otherwise lost to the system can change. In a preferred embodiment, additional data is collected in order to quantitatively characterize the "catch" rate of the animal's breath that is pulled into the air flow pipe. Specifically, in a preferred embodiment of a GreenFeed system, several independent strategies are implemented to quantify the catch rates and mixing conditions inside the feeder, including: (a) the profile of the GreenFeed system and the feed tray are designed to minimize turbulent mixing as air blows over the GreenFeed system and the animal using it; (b) a plenum at the inlet to the air flow pipe and air manifold system using one (or more than one) plenum is designed to efficiently capture emissions from the animal's nose and mouth over a well-defined region monitored by proximity sensors, and the GreenFeed system air sample pipe is designed to minimize dead volume and to enhance the "plug flow" of the gases emitted by the animal traveling through the system; (c) an air filter is placed adjacent to the inlet plenum to remove particulates that can affect measurements and sensors and help to create uniform mixing; (d) a "honeycomb of tubes are placed in the airflow pipe to create a uniform cross-sectional flow and to enhance mixing across the cross-section (alternatively, stainless-steel mixing elements designed to create multiple terminal mixing vortices and mixing with minimal pressure drop are placed within the airflow pipe (FIG. 14)); (e) sensors to monitor wind speed and direction and to document the direction which GreenFeed is pointing relative to the ambient air currents are utilized; (f) a sensor or a system of sensors, preferably an ultrasonic sensor, is used to measure the proximity of the animal's nostrils in relation to the GreenFeed air intake plenum; (g) continuous measurements of $CO_2$ mass mixing ratios in the GreenFeed air flow pipe are made; (h) continuous measurements of the mass mixing ratio of $CH_4$ and/or other metabolic gases emitted by an animal are made of a subsample of the air passing through the GreenFeed sample pipe; (i) continuous measurements are made of the changes in water vapor within the air flow pipe compared to the water vapor concentration of ambient air (since an animal's breath is saturated with water vapor, changes in the water vapor concentrations measured in the air flow pipe can be compared to ambient water vapor measurements and to the total air flow through the pipe to calculate the total flow of metabolic gases through the sample pipe); (j) continuous measurements of the air flow rate through the GreenFeed sampling pipe are made, for example, by using a pitot tube and measuring a change in pressure when the air passes through the sample pipe or by using a hotwire anemometer to measure air velocity across the sample pipe; and (k) the periodic release of a small, known quantity of a non-toxic tracer gas can be made inside the GreenFeed system to calculate total air flow rates and to define animal metabolic gas capture rates.

With regard to this final strategy, to minimize the potential for calibration errors to affect the calculation of the capture rate, the flow of tracer may be periodically switched from being released in close proximity to the animal's nostrils to the release of the tracer directly into the sample pipe. The ratio of the two values is the capture rate. This capture rate can then be used to calculate the capture rate of the animal's breath. For example, if the concentration of the tracer measured in the air flow pipe when injected directly near the animal's nostrils is 8 and the concentration of the tracer measured at the same point in the air flow pipe when injected directly into the pipe is 10, then the GreenFeed station is capturing about 80 percent of the animal's breath. Therefore, to calculate the total mass emission from the animal, the concentrations of metabolic gases (mass or mixing ratios) measured in the air flow tube are multiplied by the flow rate through the air flow pipe multiplied by a capture rate of $^{10}/_8$ or 1.25.

The GreenFeed unit (e.g., station or feeder 1310) can be designed to pivot so that it faces the wind similar to a weather vane. The shape of the GreenFeed unit typically is also designed aerodynamically to minimize turbulent mixing of air in the feeder unit so that a high percentage of the gases emitted from the animal's breath is captured under a wide range of environmental conditions.

Figure 14:
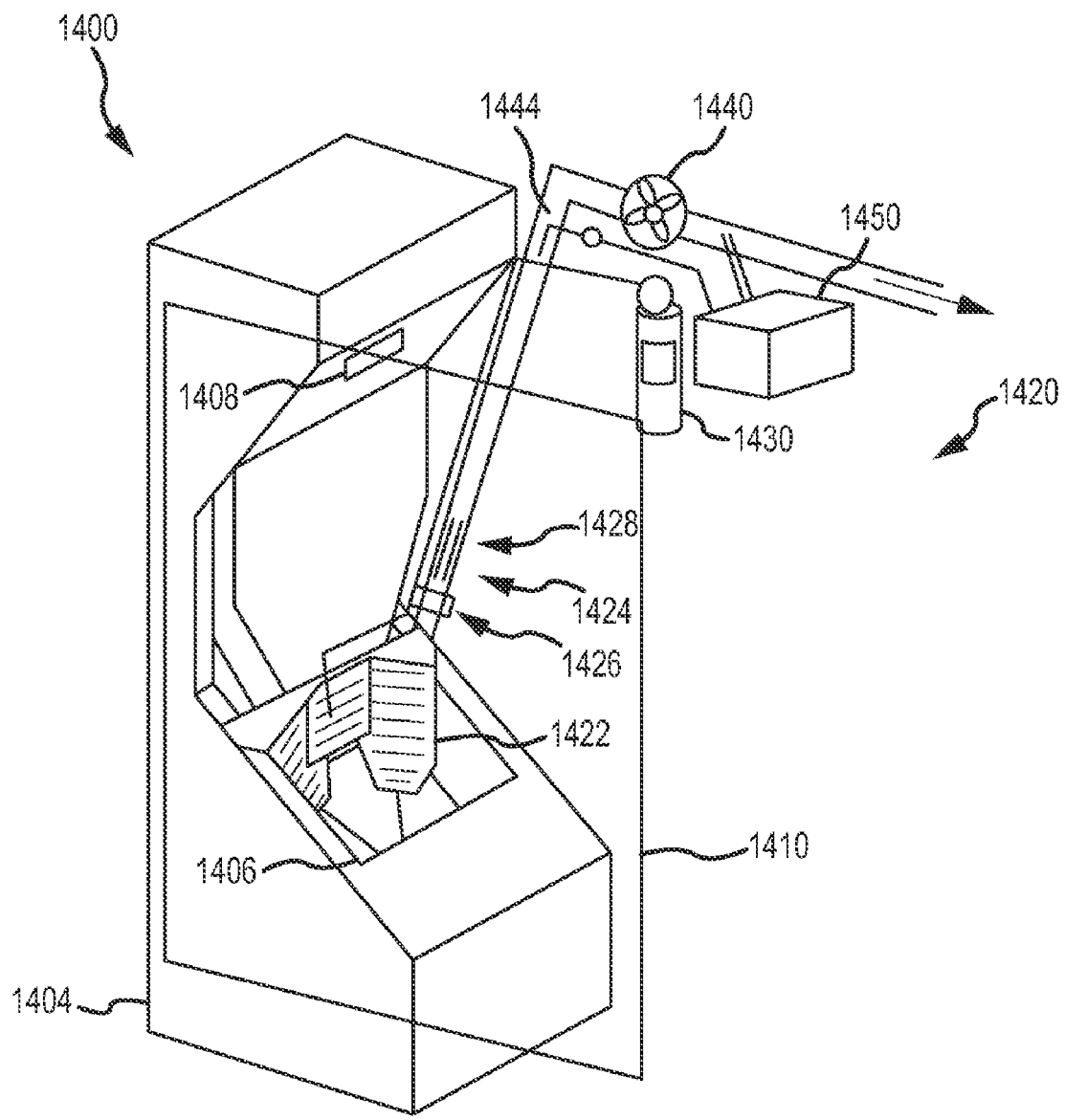
FIG. 14 illustrates another embodiment of a system for monitoring and controlling ruminant methane production/emission (or another embodiment of a concentration feeder) such as may be used with a milking robot.

GreenFeed sensors can also be retrofitted to the automatic concentrate feeder within an automatic milking robot. FIG. 14 illustrates a concentrate feeder 1400 with a body 1404 for supporting a concentrates dispenser as well as other components useful in a GreenFeed system incorporating the feeder 1400. The body 1404 is configured for receiving an animal's head and provides a feeding tray or trough 1406 in a lower portion and a head position sensor 1408 above the tray/trough 1406 for detecting when an animal has inserted its head in the feeder 1400. At this point, operation of other components useful for gas sampling or other sampling is triggered. A sheet or pair of air flow blocks or barriers 1410 may be provided on one or both sides of the head-receiving trough 1406 to reduce air flow rates and mixing to facilitate collection of the animal's breath while feeding at the trough/tray 1406. Note, the feeder 1400 may also be used as a stand-alone unit without the robot, and the GreenFeed sensors can also be incorporated into this device.

As shown, a milking robot is retrofitted with sample intake manifolds in close proximity to the animal feeding unit 1404. Specifically, the feeder 1400 includes a gas sampling assembly 1420 including an intake manifold/plenum 1420 is provided immediately above and adjacent to one, two, three, or more sides of the tray/trough 1406. The gas sampling assembly 1420 further includes a sample collection or air flow pipe 1424 with a dust collector/filter 1426 at a location upstream of sampling instruments. The pipe 1424 may further include a flow distributer 1428 to control air/gas flow through the pipe 1424.

A tracer gas input mechanism 1430 is provided to selectively (with controls that allow switching) provide tracer gas into trough/tray area 1406 for collection with an animal's breath and into the pipe 1424 (as discussed above). The assembly 1420 further includes a fan 1440 for drawing air/breath gases into the plenum 1422 and through the pipe 1424 at a desired flow rate. A flow meter 1444 may be included to determine or measure flow rate of the sampled gas on an ongoing or periodic basis. The assembly 1420 further includes one or more electronic devices/sensors such as for measuring methane, carbon dioxide, tracer gases, and other information (as discussed throughout this description).

During operation of the feeder 1400, a representative subsample is routed through the real-time analytical instruments 1450. In addition, a subsample of gas could be collected in a container (not shown) for later laboratory analyses. The specific subsample can be conditionally controlled by the computer to collect specific components of the animal's breath. For example, it can conditionally sample eructations or it can conditionally sample lung emissions, avoiding eructations other conditional samples can be set. The gas manifold 1420 is equipped with an exhaust fan or other device 1440 to pull air from the proximity of the animal's nostrils while in the dairy robot. The air flow is calibrated, preferably by direct measurement of the velocity using a device 1444 such as a hot wire anemometer or by measuring the pressure in the manifold using a device such as a pitot tube to measure pressure drop across a restriction.

In some cases, only the ratios of the metabolic gases emitted by animals are measured, such as the ratio of emitted $CH_4$ to emitted $CO_2$ as determined by operation of sensors 1450 and/or software in electronics 1450. However, in cases where it is desirable to measure mass fluxes of metabolic gases, the mass flow of air through the manifold 1420 and pipe 1424 is determined, and the capture rate of metabolic gases emitted from the animal is determined. The capture rate can be determined through the use of an external tracer 1430 in the same way as described for the GreenFeed feeder system 1300 of FIG. 13. Alternatively, the capture rate could be determined through the release of a tracer attached to the animal or emitted by the animal. As a further alternative, the capture rate could be determined for each specified set of atmospheric conditions, ambient wind speed, wind direction, and other variables. Then these variables can be used to develop correlations that are indicative of specific metabolic gas capture rates. In this case, the tracer system could be deployed intermittently in order to test and confirm the predicted metabolic gas capture rates. If a tracer gas is used which can be measured by sensors that also measure methane, it is also useful to document methane sensor calibration. Interference of the tracer gas with methane measurements can be eliminated by modulation of the tracer gas and/or by including two methane sensors with differential sensitivity to the tracer.

Basically, the GreenFeed feeder 1400 is a semi-enclosure system that is not designed to be air tight or to collect 100 percent of the animal's gas emissions all of the time, but within which, air flows and gas exchanges can be accurately quantified under most field conditions. The air exchange in the GreenFeed system feeder 1400 is optimized so that it is low enough to minimize mixing and, therefore, produce concentrations from individual animals that are much higher than the background and that can, therefore, be measured with relatively inexpensive, continuous analytical instruments 1450. However, flows are high enough so that a high and well-quantified proportion of the metabolic gases emitted by individual animals are captured under a wide range of conditions. In addition, because of the redundant nature of the measurement sensors (e.g., sensors measuring wind speed, wind direction, relative humidity, air flow, tracer release, animal nose position, $CO_2$, and $CH_4$), the GreenFeed station 1400 and an associated system with an analysis station and/or user system produces data which can quickly be processed and qualified. It is recognized that under specific conditions where there is erratic and very large mixing, resulting in relatively low capture ratios, the data will be more uncertain than data collected under ideal conditions. The GreenFeed system monitors enough variables so that data suspected of having high uncertainty can be quickly identified and sorted so that it does not inaccurately skew the results.

Figure 15:
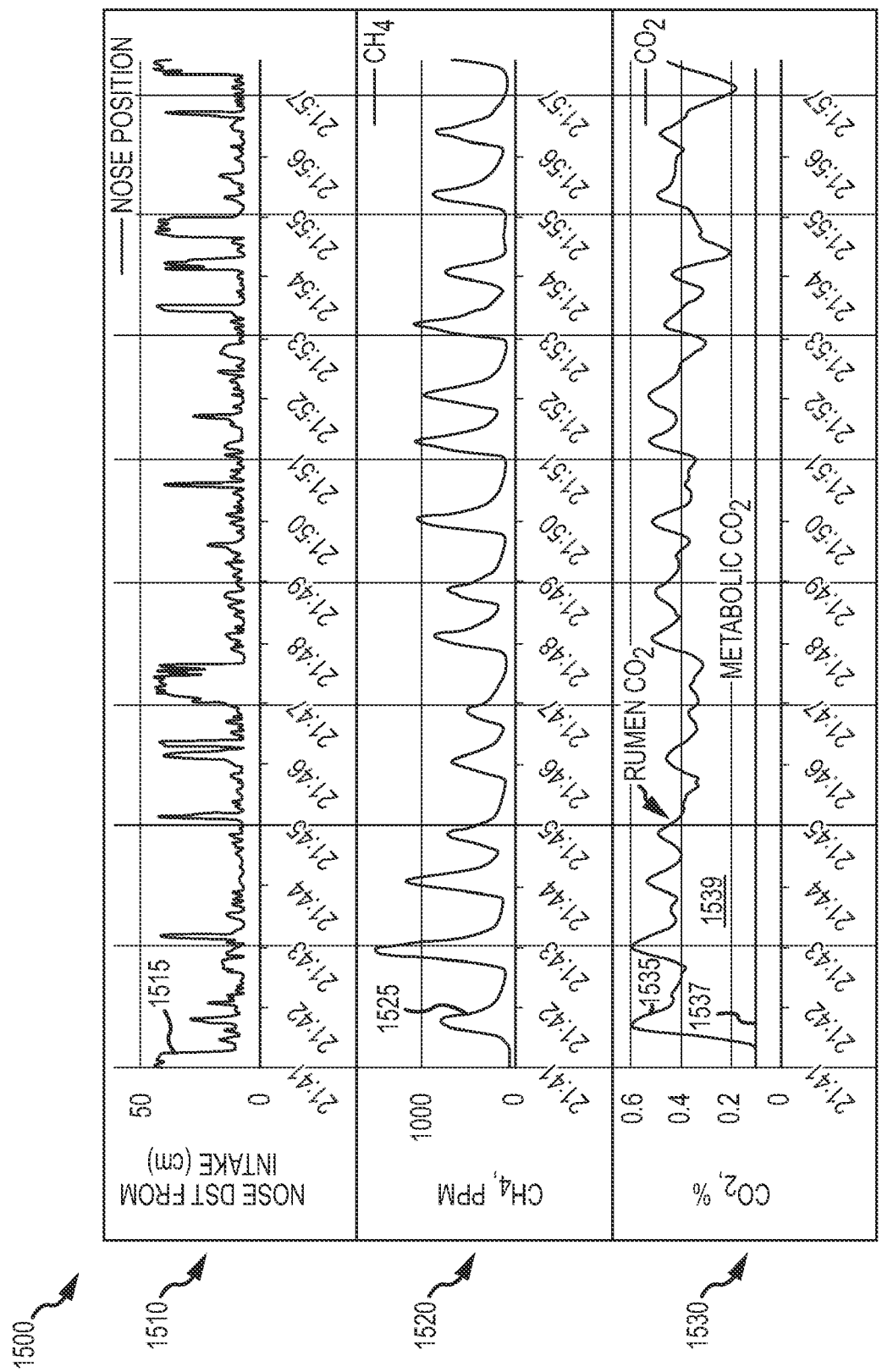
FIG. 15 is a combined graph showing, over a time period (such as a milking session), a ruminant's measured nose distance from a plenum inlet, measured methane, and measured carbon dioxide.

FIG. 15 is a combination graph 1500 showing with graph 1510 sensed/measured nose distance with line 1515 from the intake of a GreenFeed feeding station (such as stations 1310, 1400), with graph 1520 providing line 1525 showing measured methane, and with graph 1530 providing line 1535 showing rumen carbon dioxide and line 1537 showing background carbon dioxide over a test period (e.g., a milking operation with a milking robot and concentrate feeder 1400). As shown, FIG. 15 includes a 20-minute snap shot of "Nose Position" with graph 1510 and of "$CH_4$" and "$CO_2$" concentrations from the unit 1400 with graphs 1520, 1530. This data represents a series of different animals. As GreenFeed systems are used in the field, new potential uses of the data are becoming evident to the inventors. In FIG. 3, each eructation event is apparent in the data from the $CH_4$ concentration peaks (every 30-40 seconds). It is also possible to note the metabolic $CO_2$ emissions rates and $CO_2$ spikes that are emitted with the $CH_4$ peak. It is believed that the $CO_2$ spikes shown in line 1535 are associated with the $CH_4$ peaks shown in line 1525 originated from the rumen, and the difference with background at line 1537 is metabolic $CO_2$, as illustrated. In some embodiments of the GreenFeed system, changes in humidity associated with the animal's breath are also measured over time, and the measured humidity is used to provide an "internal tracer" to determine uniformity emissions measurement from an animal.

Typically, as was shown by testing and graphs by the inventors, a cow enters a GreenFeed feeder and does not immediately eructate. However, the concentration of $CH_4$ increases a small amount before an eructation occurs. It is believed that this increase is associated with $CH_4$ expelled through the lungs, which is a normal part of the physiological process. It, therefore, is possible and practical to estimate the ratio of lung $CH_4$ compared to eructated $CH_4$ so as to provide a more accurate calculation of the $CH_4$ expelled as part of eructation alone (which can be controlled through the management of supplements, concentrates, feed, and the like as described in detailed herein).

Figure 16:
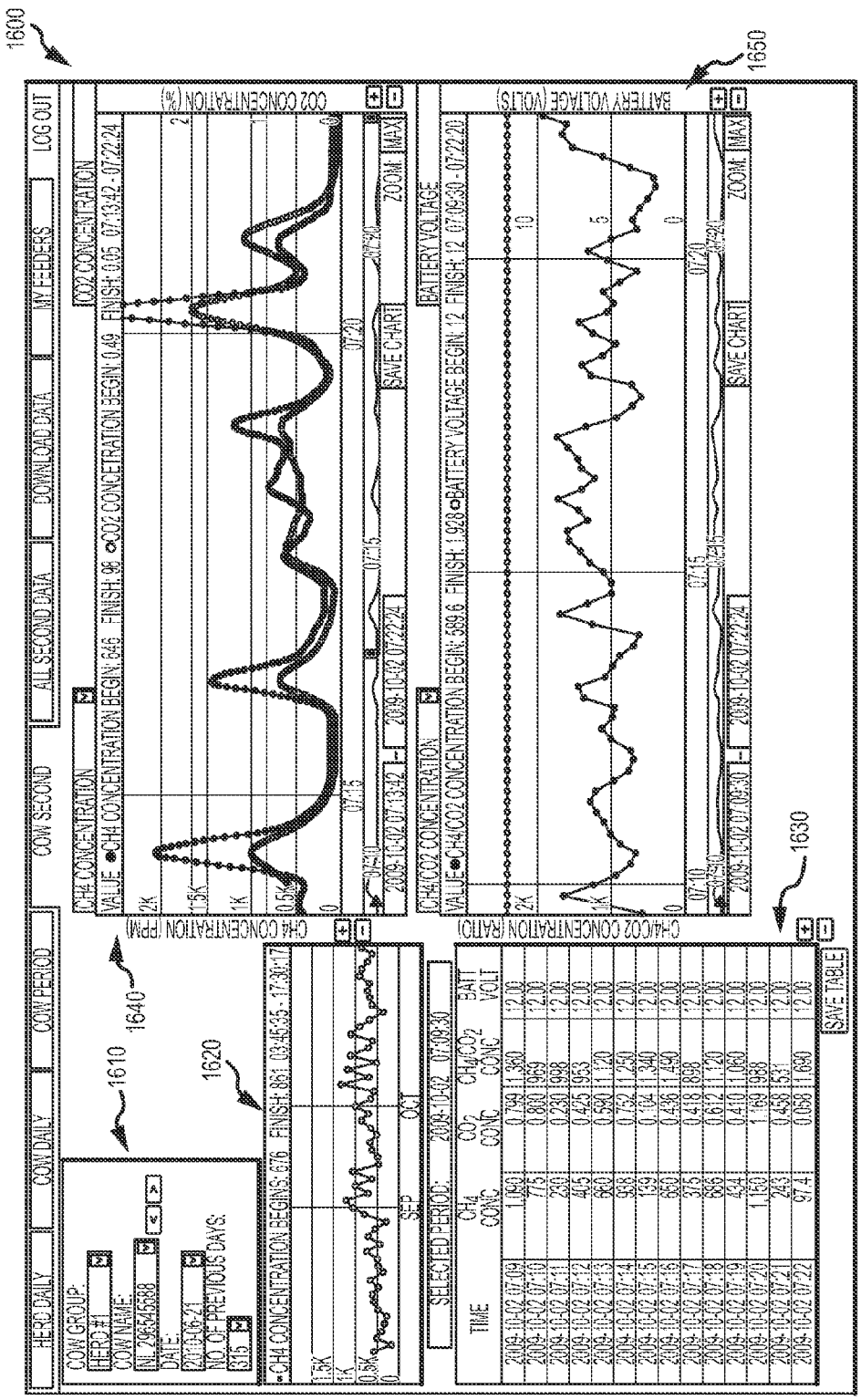
FIG. 16 illustrates an exemplary screen shot of a user interface that may be provided on a user computer system/device accessing a host server of a GreenFeed system (such as the system of FIG. 9)

Through the operation of a GreenFeed system, such as system 900 of FIG. 9, an operator or user of the system may readily view and manipulate monitored or tracked data on their herd. For example, FIG. 16 illustrates a screen shot 1600 that may be displayed on the user system 950, and the screen shot 1600 may be populated by data provided by the host server 940 over network 945. In some embodiments, the data analysis tool kit 952 processes this received data to generate one or more tables and graphs as discussed above and/or as shown in exemplary screen shot 1600.

Once the GreenFeed system 900 collects the data, the data is sent through a wireless link (926 to 930), e.g., over the Internet 945, to secure computer servers 940. The data is then automatically processed and the results are calculated for each animal at host server 940 with data analysis software that functions as described herein. The user with system 950 can access and archive the data in their own database on system 950, through a user-friendly, secure, web-based interface (which may be provided by server 940 and/or tool kit 952). The raw data is also made available in a ".csv" file format from server 940 to user system 950 via network 945 so researchers can complete their own analysis with the data on system 950 with the tool kit software 952.

FIG. 16 shows one exemplary screen-shot of the web-based user interface that is available with a GreenFeed system 900. As shown, the interface provided in screen shot 1600 includes a data selection portion 1610 in which a user of system 950 can select which data to view and manipulate. In this example, the user has selected a set or group of animals which may be an entire herd or a subset of a herd of ruminants. Then, within the selected group of animals the user can use a drop down or other entry device to select all (herd average values and so on) or to choose to inspect a particular animal as shown in FIG. 16. The data selection area 1610 may also be used to select a particular day or range of days (or a time period) for the data to be retrieved and processed via interface 1600 and use of tool kit software 952.

The interface 1600 also includes a window or portion 1620 showing a graph of the monitored methane concentrations for the chosen herd or animal in data selection window/portion 1610 over the time period chosen. Window 1630 is a table populated with times of sampling for the herd/animal and the results of the sampling including methane and carbon dioxide concentrations (which may calculated as discussed above). The table of window 1630 also shows a calculated methane to carbon dioxide ratio for the herd/animal at each sampling time. Additional data may be illustrated in interface 1600 such as the battery voltage (as shown) or other sampling parameters such as humidity, wind speed, animal temperature, and the like.

The user of the system 950 and its data analysis tool kit 952 may further process the received data from the GreenFeed server 940 to generate a number of graphs to provide visual representations of the tracked animal data. For example, the interface 1600 is shown to include a window 1640 with a graph showing methane and carbon dioxide concentrations over a selected time (such as a particular milking period or feeding station visit), and this chart shows the concentrations in an overlapping manner that correlated measured peak concentrations during each eructation. Another window/area 1650 may be used by the tool kit 952 to provide a graph of the calculated methane to carbon dioxide ratios for the herd/animal such as during the same time period used in the graph of window 1640 or another separately selected time period. As will be appreciated, the GreenFeed system provides a powerful tool for not only collecting data on a herd and individual animal basis but also for access, viewing, and manipulating the gathered data to make herd management decisions in a well-informed manner (e.g., change feed or supplements for an animal or herd based on collected and processed data, choose animals for breeding based on genetic factors causing the animals to be more efficient in processing their food and/or having more favorable rumen gas releases, and so on).

At this point, it may be useful to discuss a few of the advantages and useful functions of a typical GreenFeed system. Although the GreenFeed systems and process are entirely new, each component of the system has been extensively-tested and the operating envelopes of each sensor are well-characterized and understood. Also, the inventors' measurements of $CO_2$, $CH_4$, and the tracer with the GreenFeed system can be traced back to gravimetric standards. NDIR instruments have been available for a long time and their performance in humid environments at the concentrations encountered in GreenFeed is well-documented.

GreenFeed systems can operate to provide data that is unique and complimentary to other methods, e.g., GreenFeed systems provide snapshots in time of $CH_4$ and $CO_2$ emissions from individual animals. Many animals can be tracked over long time-periods with little intrusion on the animal's normal routine. A typical GreenFeed system does not provide continuous data for all animals, all day, every day. However, it can be operated to provide real-field data for many animals every day. This data is ideal to initialize, anchor, and calibrate models that can therefore more-accurately predict diurnal fluxes. In addition, a GreenFeed system as described herein can very quickly, cost-effectively, and unobtrusively identify changes in the rumen and metabolic behavior of individual animals over time. In general, a primary advantage of the GreenFeed system is that it is much easier and less expensive to gather emissions data from a large number of individuals without significant handing of the animals or the associated set-up time, analytical work, and costs. GreenFeed systems are also robust and simple to maintain over a long time-period so the systems can be useful for long-term studies. In addition, components of a GreenFeed system are portable and can be easily moved to new locations as research demands change.

In practice and use, the rations automatically dispensed by a GreenFeed system influence the rumen biology and/or grazing behavior. For example, on very good pasture in South Dakota, animals will still visit a GreenFeed feeder for several minutes each day to consume a supplementary ration of a few cups of alfalfa pellets and have their breath sampled for emissions. In this case, the small amount of "bait" fed to each individual is so similar to the actual forage in composition that the bait will not significantly impact rumen function. Alternatively, the GreenFeed system with its feeder stations/mangers could be set up to deliver a specific mineral mix, feed supplement, or antibiotic to only select animals in the herd. The results on $CH_4$ and $CO_2$ can be monitored with the GreenFeed system. The potential applications, treatment, and deployment options are only limited by a system operator's creativity and their project goals.

Numerous studies can be completed with a GreenFeed system. Monitoring ruminant metabolic gas emissions provides insight into rumen biology as well as in catabolic and anabolic processes. For example, the data indicates that a GreenFeed system can help to differentiate $CH_4$ and $CO_2$ produced in the rumen from $CH_4$ and $CO_2$ emitted directly from the lungs. This data is likely to be quite sensitive to any physiological or behavioral changes that might occur in each individual animal. Therefore, there should be many potential research applications of GreenFeed to enhance the efficiency, improve animal welfare, study animal heath but simultaneously to lower costs for individual producers in the animal husbandry industry.

One study may be performed using a GreenFeed system to study $CH_4$ production and dry matter intake (DMI). Past studies have found that $CH_4$ production is closely related to DMI for individual animals. Therefore, the $CH_4$ measurements obtained from GreenFeed may be used/processed by the GreenFeed data analysis software to estimate the amount of DMI for specific animals in a herd, especially relative to each other. The GreenFeed system may also provide a reasonable estimate in a pasture/range system where it is difficult to estimate DMI for specific animals.

In another case, a GreenFeed system may be used to study $CH_4$ and $CO_2$ emissions in relation to disease detection and prevention. Since DMI for individual animals is linked to $CH_4$ production, health conditions that impact DMI may be quickly reflected in the $CH_4$ and $CO_2$ fluxes. Changes in fluxes, monitored by a GreenFeed system, then could be used to quickly alert the producer of a potential problem (e.g., the GreenFeed server could issue alert communications when predefined threshold changes in fluxes are detected or such an alert may be set on the user system in their data analysis tool kit), which may limit treatment costs and productivity declines. In addition, it is also likely that specific respiratory diseases that limit efficient lung-air exchange will be reflected as changes in respiratory $CH_4$ and $CO_2$ compared to rumen $CH_4$ and $CO_2$. The GreenFeed system may provide data to quickly and effectively monitor such changes.

In another example, a GreenFeed system may be used to study $CH_4$ production, diet, and supplements. $CH_4$ emissions represent lost efficiency to the animal. In addition, $CH_4$ is a greenhouse gas. Reducing $CH_4$ emissions both increases productivity and reduces greenhouse gas emissions. It is well understood that certain feeding strategies and supplements can potentially reduce greenhouse gas emissions. GreenFeed can be used to document the effectiveness of specific treatments and to manage which feeds and supplements are provided to animals in response to measured methane emissions by particular animals or by a herd.

In one study example, a GreenFeed system is used to study $CH_4$, $CO_2$, and animal efficiency. It is well-documented that the $CH_4$ losses of individual animals under identical conditions can vary from each other significantly. The GreenFeed system is ideal for monitoring these differences. Further, GreenFeed-collected and processed data can help to determine the causes of efficiency differences observed to help answer questions such as: "Are $CH_4$ and $CO_2$ flux differences due to environment, behavior, or genetics?"

In another study example, a GreenFeed system may be used to study $CO_2$ emissions and heat stress. Heat Stress increases metabolic rates in mammals. A GreenFeed system can be used to measure the metabolic emissions of $CO_2$ under varied atmospheric conditions. It can also be used to evaluate the differences in heat sensitivity among individuals. In addition, $CH_4$ production rates are likely to be affected if heat stress leads to changes in behavior that are reflected in diet or activity level.

As yet another example of a use for a GreenFeed system, a system may be used to study $CH_4$ and $CO_2$ emissions and heat detection. DMI typically decreases during the onset of an animal's estrus cycle. In addition, animal activity has been documented to significantly increase. Therefore, it is likely that changes in $CH_4$ and $CO_2$ emission rates for specific animal can be an additional indicator that an animal is in estrus.

In another case, a GreenFeed system may be used to study $CH_4$ emissions and pasture quality. Pasture quality changes as a function of grazing intensity and climatic variables. As forage quality decreases, the fraction of gross energy intake lost as $CH_4$ also increases. Therefore, a GreenFeed system may be configured to monitor for or track significant changes in $CH_4$ and $CO_2$ that will effectively act as indicators of when optimal grazing intensity is achieved and/or when there is a need for or may be a benefit of providing one or more additional nutrient supplementation to a herd (e.g., alert an operator when too many animals are on a pasture, when herds should moved to rotate use of pastures, when supplements alone may overcome a deficient pasture, and so on).

As will be appreciated, a GreenFeed system may be used by nearly any manager of a herd of ruminant animals. The inventors have installed GreenFeed in a robotic milking machine, a tie-stall dairy, and in a pasture environment. It will be easy to adapt the same feeder to a feedlot or other dairy environment. In crowded conditions, a GreenFeed system may benefit from normal animal control measures to limit access to the feeder to one animal at a time for each sampling period (e.g., 5 minutes or more per sampling in some cases). In this regard, though, access can be easily automated using typical animal control measures.

The number of cows per GreenFeed feeder or sampling station will depend on the application and the situation. It will be useful for users to estimate the number of feeders required for their specific goals. The GreenFeed unit can be used on multiple animals and in continuous feed situations. Where animals have close access to the unit/feeder most of the time, the feeder will be able to service many animals such as cows (perhaps up to 60). In pasture situations, where the animals such as cows move and do not spend significant time at one specific location, it might be preferred to use more feeders (or fewer animals per feeder/sampling station).

In some embodiments, each animal utilizes a GreenFeed station for at least five minutes total per session. That schedule provides measurements for 6 or 7 eructation events. Eructation rates can vary, but the collected test data indicates that they normally occur every forty seconds for most animals. Therefore, a GreenFeed system user can estimate how much time the animals/cows are to spend at a GreenFeed location and how many GreenFeed units will be used to meet specific project goals. The GreenFeed systems generally have been designed so that each animal can be fed a specific amount of food supplement in a specific time period. In addition, with multiple feeders, specific animals could be allowed to eat at one feeder and others at a different feeder with different food type. Therefore, the animals can be treated differently, and the system is very flexible for adapting to a specific research program.

At this point in the description, it may be useful to describe a typical sampling sequence for a specific animal during use of a GreenFeed system. This description describes an exemplary useful design and also includes potential variations and alternatives to this exemplary (but not limiting) design. First, an animal, preferably a ruminant animal such as a cow, approaches a GreenFeed feeding station. The GreenFeed unit in some preferred embodiments is configured to pivot into the wind (e.g., with the opening to the hood/manger is facing away from the wind and airflow or with the solid body of the hood/manger facing the oncoming wind) so that the animal is facing into the wind with its head inserted into the GreenFeed unit or feeding station. With this wind vane-type rotation of the unit, the wind flow is directed over and around the GreenFeed unit in a way that minimizes turbulence and mixing within the hood/manger where gas sampling occurs.

The shape of the GreenFeed feeding station or hood/manger is optimized so that when occupied by an animal, the airflow into the opening of the hood/manger is smooth and turbulent mixing where the animal's nostrils are located is minimized (or at least reduced to acceptable levels). Alternatively, the GreenFeed feeding station or unit could be located in a barn or other shelter or in an automated milking machine or in a communal water dispensing system so that the effect of variable wind currents and wind directions is minimized. As another alternative, the mixing near the head of the animal could be minimized through the placement of curtains made of a flexible material such as rubber flaps or translucent plastic wind-doors (e.g., the animal inserts their head through movable rubber flaps that may be supported at the top of the opening or at the sides of the opening). As a further alternative, mixing could be restricted with an air curtain, where air is directed through a narrow slit across the open end of the GreenFeed unit to restrict mixing. Alternatively, the plenum that leads into the sample pipe/sample manifold could be replaced by a "fumehood" type cover through which air and the animal's metabolic gases are pulled.

In other words in some embodiments, the GreenFeed stations or units are designed to reproductively minimize mixing and/or to reliably quantify mixing. Without such a design, the stations are most useful for the measurement and monitoring of ratios of metabolic gases, such as $CH_4$ to $CO_2$ ratios and of changes in the ratios of these and other similar gases. However, many embodiments where mixing is controlled and/or quantified are useful for the measurement of the mass fluxes of these gases. Measurement of the mass fluxes of specific metabolic gases is useful in determining ruminant efficiency and the effectiveness of $CH_4$ reduction strategies.

As a second step of the sampling sequence, the animal preferably is equipped with a passive RFID ear tag, an RFID-tagged collar, or an active-RFID ear tag or collar to allow each animal to be identified by the GreenFeed system. Alternatively, the animal may not have any tag or collar, but it can be identified from a camera located in the vicinity of the GreenFeed station, but, in some cases, each animal is not identified except as a member of a local population of such animals. With regard to a third "step" in the sampling sequence, the GreenFeed system contains devices/components for recording the presence of the animal. For example, each GreenFeed unit may contain an RFID reader that can decode the animal's tag and identify a specific individual to the data logger/data analysis station. GreenFeed units also utilize audio and visual cues as an aid to training and to notify animals in the vicinity that they will receive a reward if they visit the unit.

As a fourth or next step in the sampling sequence, based on information collected about the individual animal through independent or through coupled data gathering systems (such as scales to determine animal weight and/or measurements of animal milk production), the GreenFeed system with its analysis software and/or the GreenFeed operators manually determine an optimal allocation of mineral supplement or supplemental feed to be delivered to the animal over a specified time-period. Feed is preferably dispensed at a rate that is no faster than the animal's rate of consumption in order to minimize material left over for the next animal and to discourage "bullying" behavior where a dominant animal attempts to force the animal utilizing the GreenFeed system out. In addition, a system of gates and chutes can be implemented to minimize this crowding behavior if necessary. Preferably, if the animal leaves before his allocation is completely consumed, the dispensing system stops. If the animal approaches at a later time, another portion of the daily ration can be dispensed. In this way, each animal can be encouraged to visit the GreenFeed unit several times per day if the operator desires. Further individual dispensing times can be set so that specific animals are dispensed at specific times of the day.

As a fifth or next step in the sampling sequence for one embodiment, the animal is equipped with an active RFID tag that includes a sensor that is resident in the animal's ear canal. When the animal approaches the GreenFeed unit, its identity and its body temperature are read and recorded in a GreenFeed computer/data logger located in proximity to the GreenFeed unit.

As a sixth or next step in the sampling sequence, when the animal is near the GreenFeed unit, an air sampling pipe/air sampling manifold is activated. The fan turns on and pulls a flow of approximately 100 cubic feet per minute through the GreenFeed air sampling system. In the GreenFeed field unit, the air is first pulled through a plenum including a perforated plate that is immediately adjacent to the animal's nostrils while its head is in a feeding position. The plenum is designed to minimize turbulent mixing of the animal's breath and eructations. In this way, air that is pulled from around the animal's head, over its nostrils and mouth area entrains the animal's metabolic gas emissions into air captured and routed through the air sampling manifold/air sampling pipe. The GreenFeed unit or manger/hood is designed to capture the animal's breath and eructations quickly to minimize mixing with ambient air outside of the unit.

In a seventh or next step, the flow through the air sampling pipe and/or air sampling manifold passes through the plenum and then through an air filter designed to remove dust and large particulates that could affect the performance of sensors. In an eighth or next step of the sampling sequence, the air passes through structures designed to uniformly mix the air across the cross section of the air sample manifold/air sample pipe (e.g., across/through the flow distributer 1428 of sampling assembly 1420 in FIG. 14). In one preferred embodiment, mixing structures include "tabs" attached to the sides of the air sampling pipe 1420 in FIG. 14. Other mixing structures can include restrictors and baffles and/or plastic tubes about 0.25 centimeters (cm) in diameter and 15 cm in length that are bundled together and packed into the air sample pipe in the flow path to create mixing. These tubes serve to help maintain flow in the sample pipe/sample manifold (e.g., sample manifold 1424 of assembly 1420 in FIG. 14).

As a ninth or next step in the sampling sequence, air flowing through the air sample pipe/air sample manifold then flows over sensors configured to measure or sense data relative to moisture, temperature, pressure and velocity. Not all of these measurements are required at all times. The important thing is that the air flow through the sample pipe/sample manifold is very well characterized and can be accurately monitored or inferred.

As a tenth or next step in the sampling sequence, when the animal inserts its head into the Greenfeed unit, a proximity sensor, e.g., an infrared or ultrasonic sensor, detects the position of the animal's head with respect to the sample plenum/sample inlet. The time and position are then recorded such as by the data logger. In addition, the GreenFeed unit can include one or more cameras that will record the presence of an animal and which can also be used to identify specific individuals if tags are not available or used.

As an eleventh step, the RFID and proximity information is then used by the data loggers and/or the data analysis station to make decisions about dispensing feed and recording data from the analytical instruments. In practice, the analytical sensors normally require a significant warm-up time. Therefore, those sensors are operated continuously. Depending on the availability of power, the fan (or air pump) that pushes or preferably pulls air through the sample pipe/sample manifold can be left in operation continuously or it can be switched on when the animal is detected to be present.

As a twelfth step in the sampling process, the animal has approached the GreenFeed unit, the animal has been identified and its supplemental ration and feeding schedule has been determined. The unit with its automated feed hopper operates to dispense a portion of the daily ration at a rate that keeps the animal's head in the unit but also that is slow enough so that the animal occupies the unit for a length of time sufficient to monitor several eructation cycles.

As a thirteenth or next step, the tracer can be released during the measurement period in several different ways. If a tracer-specific sensor is available, it can be turned on when the animal approaches the GreenFeed system and turned off when the animal leaves. During the time that GreenFeed unit is occupied by an animal, it can be switched from a quantitative or, at the very least, a carefully controlled rate of release near the animal's nostrils to an identical release inside the air sampling pipe/air sampling manifold. The ratio of the two values determines the capture rate of the sample.

As an alternative or a fourteenth step, if the analytical system responds to the tracer gas, as is the case for most NDIR instruments designed to measure $CH_4$ but which also respond to propane, for example, then the tracer release can be modulated so that its signal can be differentiated from that of the $CH_4$ emitted by the animal. Preferably, several eructations can be measured, the tracer gas can be released, offsetting the baseline, over several more eructations, and finally the tracer release can be switched to flow inside the air sample pipe/air sample manifold. In another example, when the eructation interval for a specific animal is determined, a pulse of trace gas can be released to create a peak that occurs between eructation events and alternated between external and internal releases.

As an alternative or as a fifteenth step in the sampling sequence, a differential absorbent, such as "Carbo Sieve s3" distributed by Sulpelco, can be packed into a short filter tube. When the tube is placed in line with the $CH_4$ analyzer, the tracer gas (propane or butane) is differentially scrubbed so the signal only includes $CH_4$. When the filter is switched offline, then the analyzer will detect both $CH_4$ and the propane tracer. The ethyl mercaptan oderant added to propane and butane gas can also leaks be differentially scrubbed, for example with iron oxide, if it is suspected that it negatively impacts the animals being sampled.

As yet another alternative or as a sixteenth step, the tracer can be released for selected animals during selected atmospheric mixing conditions. In this way, the capture rate can be determined quantitatively under specific, measured conditions. These capture rates can then be used to develop a simple regression model or numerical relationship that links specific GreenFeed measurements (for example wind speed and wind direction) to measured mixing. This relationship can then be used to predict the capture rate for each animal for each sampling period.

Alternatively or as an seventeenth step in the sampling sequence, changes in moisture measured in the sample pipe compared to ambient measurements are used to correct fluxes for the capture rate changes that occur during a sampling period. For example, the relative humidity measurement may rises from 70% (ambient air) to 90% when the animal inserts its head into the GreenFeed unit. However, the proximity sensor indicates that the head remained in position, yet the relative humidity in the sample pipe/sample manifold dropped to 80% during the sample period, corresponding with an increase in wind speed. The data analysis system may determine that mixing increased by the ratio determined by the flow rate of ambient air and the change in the total mass flow of metabolic gases from the animal into the feeding station or sampling unit.

As a next or eighteenth step, measurements of $CH_4$, $CO_2$, and other metabolic gases are made and recorded such as at one-second intervals. Preferably, the recorded data is accessible by remote computer systems and/or smart phone systems. Alternatively, data is stored on a local data logger for periodic collection, e.g., by technicians remotely polling the logger or physically visiting the unit to retrieve the recorded data.

The GreenFeed system can be operated in an automated mode, where conditional decisions are programmed through a remote computer, or smart phone. Alternatively, the GreenFeed system can be operated in manual mode through a cell phone/Internet link. The animal consumes its ration for the specified time period. It then leaves and the next animal enters and the cycle is repeated. The total time each animal occupies the GreenFeed unit typically does not exceed about eight minutes.

One question that may arise with use of a GreenFeed system is how short-term $CH_4$ flux measurements are related to daily fluxes and what is the uncertainty associated with making periodic measurements. The answers to these questions generally depend on the animal management system. The diurnal cycle of $CH_4$ and $CO_2$ are affected by the frequency of feeding in a confined animal operation or the specific grazing regime in a pasture situation. For confined systems such as a modern dairy, animals are fed continuously, and it is likely that diurnal variability is less than on pasture. In a pasture, grazing is impacted by forage quantity and quality and the proximity of water. In any given system, it is possible to use the GreenFeed data to estimate total daily emissions rates for many animals in an unobtrusive, cost effective way. Generalization of the data involves the utilization of appropriate extrapolation methodologies. This can include numerical models calibrated to field data and/or simple parameterizations based on the frequency and timing of GreenFeed periods for each animal.

In pasture-grazing systems, the animals may exhibit a diurnal cycle of behavior and tend to visit the feeder at specific times. For example, it has been found that cows generally visit a GreenFeed pasture feeder in the morning and evening because it is typically placed near water. It is therefore important to relate a morning and evening measurements to the understood diurnal fluctuations in $CH_4$ emissions observed in pastured animals. By placing the GreenFeed units in strategic locations in the pasture, animals can be enticed to visit the feeder at varied times over a day. Regardless of the particular implementation of a system, the GreenFeed systems are very useful for determining relative emission rates among animals in any system and to detect changes in an individual that occur over time. In a feedlot or dairy, where feed times and visits can be more random, the randomness of the sampling increases the ability to measure the animal's variable emissions over time.

Daily emission can be estimated from one seven-minute sampling period for an animal such as a cow. This example assumes a constant $CH_4$ emission rate over the day. However, numerical models could easily be applied to the spot measurement to better estimate a daily value. The area under a curve at the peaks associated with each eructation may be used to determine average mass of methane per eructation and the number of eructations per day may be used to estimate methane emissions for this animal over a day. For example, in one test, a seven-minute sampling period was used when a cow had its head in a hood or sampling unit. Seven eructations occurred with an average length of about 50 seconds, and the average mass per eructation was determined to be 0.10 grams. If this is then extended over an entire day, it may be estimated that the cow would have 1700 to 1800 eructations in a day (e.g., about 1769 eructations). This would result in the cow having methane emissions of 176 grams per day assuming the monitored rate of average emissions continues throughout the day.

Some embodiments of the feed or sampling station (such as a tie-stall unit for use in dairy operations or the like) may include an auxiliary sample collection system. The auxiliary sample collection system or assembly allows a user to collect a sample in a container or on a filter to take to an analytical laboratory for analysis of constituents that cannot be measured by continuous instruments (such as those installed in the GreenFeed units). A typically auxiliary sample collection assembly includes plumbing that lets the user manually or automatically collect either a quantitative sample at the exit of the sample tube or a qualitative sample at the front end prior to mixing and potential scrubbing by the filter and walls (which may be important for aldehydes and alcohols and other sticky constituents).

The GreenFeed system's data analysis software or the local software provided as part of the controller for the auxiliary sample collection assembly includes programming so that the samples can be collected conditionally. To this end, the controller (with its own software or in response to a control signal from a remote controller/data analysis system/station) determines when an eructation is detected and, in response to such detection, turns on a sample pump of the auxiliary sample collection assembly. Conversely, the controller and its software may be configured to perform sampling only when there are no eructations. Sampling can also be conditional on other data and signals as well. For example, the controller may initiate sampling when the proximity sensor detects the presence of an animal's muzzle in the optimal position or when the animal's respiration is detected within a hood or GreenFeed unit. In some cases, the assembly's controller functions to affect sampling of each breath but avoids eructations.

As discussed above, field or pasture-based units may have batteries that are recharged through the use of one or more solar panels while dairy/stall-based units may be hardwired for power. Numerous other added components or features may be provided with each GreenFeed unit to provide an overall more effective GreenFeed system. For example, a GreenFeed unit may be equipped with sound and light assemblies/devices operated by a local or remote controller to selectively provide tones/sounds audible and visible, respectively, by nearby animals. These audible and visible signals can be used in many different combinations and ways to condition the animals to engage in specifically-desired behavior.

For example, when an animal approaches and its ear tag is read, if it is eligible to get a "treat" a light will turn on and a tone may sound. When the animal inserts its head completely into the GreenFeed and is detected by the proximity sensor, the feed can be dispensed after a small delay. Eventually, the delay between lighting and/or other signals can be increased before a treat is dispensed. In this way, the animal can be effectively trained to place its muzzle in the optimum position long enough for us to collect data for several eructations yet minimize the amount of "reward" dispensed. This has several advantages. It minimizes changes in the animal's diet, it trains the animal to keep its head in the correct position (greatly improving data quality), and it minimizes requirements to service the unit. In other words, the units do not have to be services as often such as to add feed or clean air filters.

Alternatively, the GreenFeed unit may be configured to provide a tone or a different light signal or both when the required data has been successfully collected to cause or encourage the animal to leave. In this case, the signal may even be associated with a small static charge (like that from a cattle prod) to encourage the animal to move on. The charge could possibly be administered through the feeder dish, but this may not be desirable since the animal might then avoid the unit all together. In some cases, the electric charge is administered through a wire hanging down from above the animal's back. Such a system for encouraging an animal to leave a location is used in robotic milking machines and works well. Eventually, a change in the light and/or a tone will be enough to encourage the animal to exit to avoid the shock or other negative feedback (e.g., a release of an oderant to encourage the animal to exit). For example, some GreenFeed units may use propane as a tracer to determine the "capture ratio" in GreenFeed, and the inventors have noted that some animals do not like the odor of the tri-methyl sulfide that is commonly added to propane as an oderant. In some units, a scrubber is used to remove the oderant prior to release of propane when an animal is present such that it would be easy to equip the propane cylinder with a three-way valve to release propane with the oderant as a signal that it is time for the individual to leave the GreenFeed unit. Other odorants could be used as well.

As will be appreciated, there are a lot of potential combinations of stimuli and behaviors that may be used with a GreenFeed unit to encourage or discourage particular actions by animals. Also, a GreenFeed system may include one or more stand-alone training units that have these signaling capabilities and detects the animal's presence and dispenses a "treat." The training unit, though, would not contain gas sensors or any other sensor. It may be configured to only have a simple motion detector and be controlled such that when an animal approaches, it drops feed. The training unit may also contain an RFID reader so that specific animals can be identified and lured in on a schedule.

In one implementation of the techniques described herein, a unit was built for a tie-stall research dairy. In order to fit below the tie-bar of a typical diary, the unit was mounted to a very low three-wheeled cart. The unit was AC-powered but had a power-conditioning system and battery backup so that it can operate for a period of time without AC power. In addition, the unit included a set of sampling valves and a pumping system to collect gas samples for exploratory analytical measurements. The sampling system was very flexible in that it was adapted to be programmed to collect air samples at specified time intervals and it could be set to sample individual eructations.

A number of design improvements or aspects may be included in a typical standalone feeder or GreenFeed unit such as the feeder 910 of FIG. 9 or feeder/manger/hood 1310 of FIG. 13 or in a typical tie-stall dairy unit. These design aspects may be incorporated to make the units easier to use and to move. For example, the top of the food-bin may be kept relatively low in height so that it is easier to fill (e.g., a fill opening at 4 to 6 feet or the like), and the food bin may include a 50 lb (or other sized) food extension to increase the overall storage/dispensing capacity (e.g., up to 100 lbs or more).

The food drop tube in the hood/manger may be located out of the way of the cow's nose. Each hood/manger of a GreenFeed unit may include a food tray or dish and an air intake manifold is positioned adjacent or nearby the food tray/dish. In some embodiments, the intake manifold is made from stainless steel, and it surrounds the animal's muzzle (e.g., with a wall (which may have three sections or be arcuate) extending at least about the sides and front of the animal's muzzle) to further increase the GreenFeed system's breath capture rate uniformity. The unit can be used with or without wing extensions on the feeder that help restrict mixing. Normally, it may be useful to train the animals (such as cows) without the extensions, then add them after a couple days if needed to reduce mixing in the hood/manger. To date, under current field operating conditions, the wings have not been required to obtain useful sampling results. A head position sensor and/or cameras (such as a web camera) may be in-laid or in recessed locations within the feeder/unit so that the animals do not lick or damage the devices.

Figure 17:
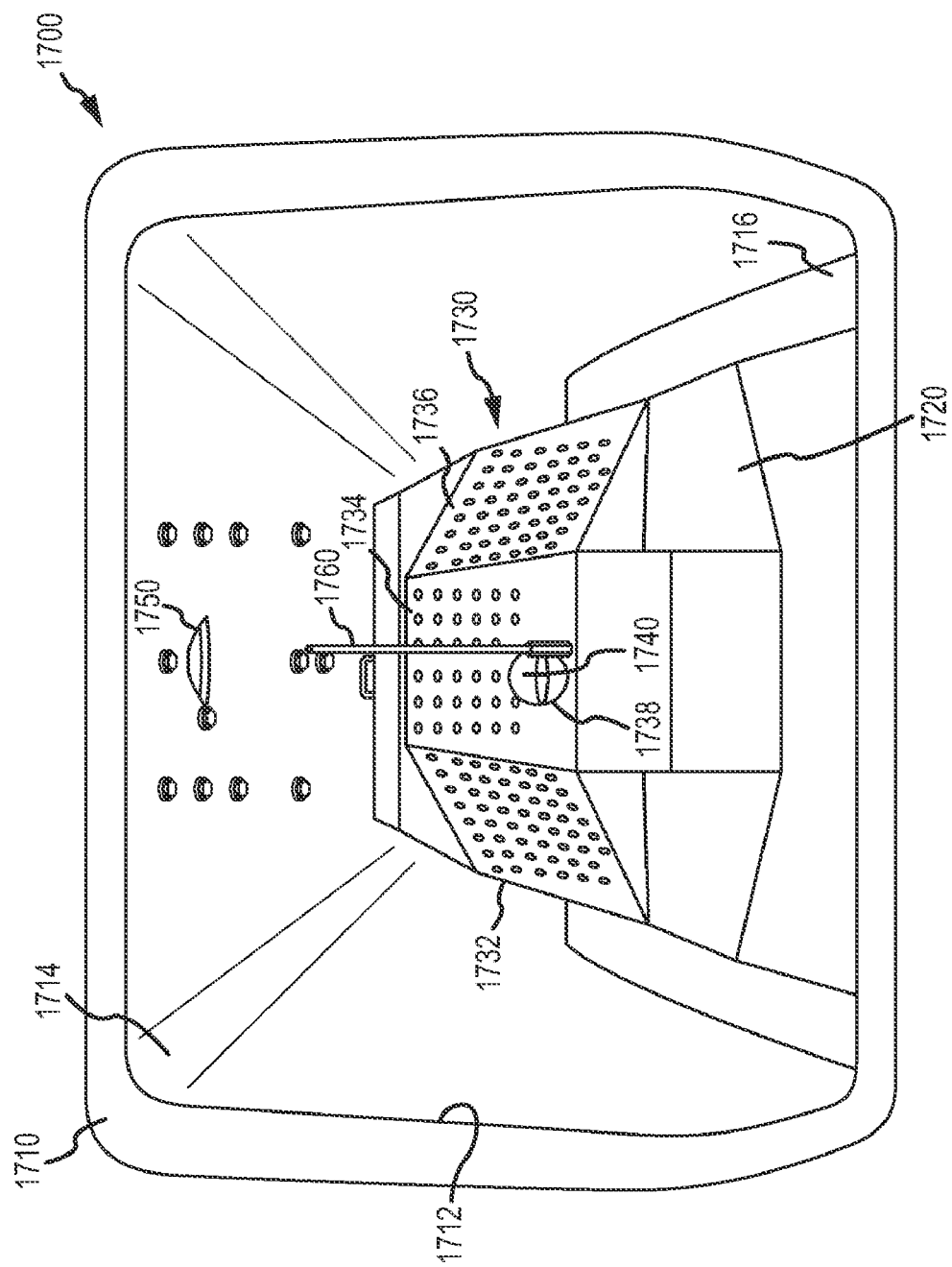
FIG. 17 is a side view (opening side view) of a GreenFeed feeding station showing one embodiment of a hood/manger with its food tray and sampling inlet plenum.

FIG. 17 illustrates a feeding station or GreenFeed unit 1700 showing one arrangement of the interior portion of a manger/hood that is useful for sampling animal's breath. As shown, the feeding station 1700 includes a hood/manger 1710 that may have a hollow body that is generally wedge shaped. The hood 1710 includes an opening on one side for receiving an animal's head and the interior space of the hood 1710 is defined by the inner surfaces 1714 of the hood wall 1710. On a bottom surface or wall 1716 of the hood 1710, a food tray 1720 is positioned and is configured with a recessed surface for receiving food/supplements that may be dispensed from the food bin outlet 1740 (which is typically positioned in a forward location in the hood 1710 so that an animal's nose is not blocking the outlet or so that feed is not dispensed on the animal).

The unit 1700 further includes a sampling intake plenum 1730 that is configured to wrap about the sides and front of an animal's head/muzzle when it is feeding at the tray 1720. To this end, the plenum 1730 includes three inlet surfaces/walls 1732, 1734, 1736 that include a number of inlets through which air/gas for sampling may be drawn out of the hood 1710. The inlet surfaces 1732, 1734, 1736 extend up from the tray 1720 and may be angled inward some amount to better capture the animal's breath/eructations (such as at angles of 15 to 45 degrees or the like). The side surfaces 1732, 1736 may extend toward the opening 1712 at an angle (such as at 30 to 45 degrees) and a distance to provide a desired amount of "wrap" about the animal's muzzle (such as 3 to 10 inches extension toward opening 1712 or the like depending upon the animal's size).

The unit 1700 also includes a recessed inlet or surface 1750 in which a sensor may be provided to sense the presence of an animal's head/nose. This sensor is shown to be positioned directly above the food tray 1720 but may also be positioned elsewhere in the hood 1710 such on a side of the inner wall 1714. Further, the unit 1700 includes a tracer gas outlet 1760 that may include a tube extending to a location proximate to the front sampling plenum wall/surface 1734 or elsewhere in the hood 1710.

The design of the gas collection pipe may also be varied to practice the invention. In some cases, the collection pipe is configured to facilitate uniform horizontal mixing while avoiding stretching the sample along the tube. In addition, the collection pipe or tubing may be configured to create uniform velocity profiles of sampled air/gas so that flow-rates and fluxes have a significantly lower uncertainty. The collection pipe or assembly may also be configured to control (e.g., decrease) the $CH_4$ and $CO_2$ lag times. The lag time is the amount of time between the release of a sample and when it is actually measured by the sensors. In some early embodiments, the lag time was about 17 seconds but in later configurations the lag time is only about 6 seconds.

In practice, a GreenFeed unit or station is configured to include sensors for methane, carbon dioxide, hydrogen, hydrogen sulfide, water vapor, temperature, air velocity, head position, RFID sensors for ear tags, and more. To train and control animal behavior, each unit typically includes signal lights and a tone-generating sound system. These can be used through various programming options to condition the animals to be aware that if they approach the unit at the specified time (day or night) a treat will be dispensed.

The invention claimed is:

1. A method of managing methane emissions from a ruminant, comprising:
   providing a mechanism for dispensing feed to a ruminant into a food tray;

first measuring carbon dioxide and methane in air proximate to the food tray to determine a background gas level;
sensing a ruminant proximate to the food tray in the feed dispensing mechanism;
in response to the sensing of the ruminant, second measuring carbon dioxide and methane in air proximate to the food tray;
with a data analyzing station, processing the first and second measured carbon dioxide and methane concentrations to determine an increase in carbon dioxide and methane concentration; and
with the data analyzing station, determining carbon dioxide and methane fluxes for the ruminant based on a total airflow and on the determined increase in the carbon dioxide and methane.

2. The method of claim 1, operating the data analyzing station to determine, based on the determined carbon dioxide and methane fluxes, a supplement to be presented in feed dispensed by the dispensing feed mechanism to the ruminant to control methane emitted by the ruminant.

3. The method of claim 1, wherein the feed dispensing mechanism includes a gas collection pipe with an inlet adjacent the food tray, a fan moving air over the food tray into the gas collection pipe, and an airflow sensor measuring air flow in the collection pipe to determine the total airflow when the ruminant is sensed to be in the feed dispensing mechanism.

4. The method of claim 3, further comprising operating a tracer system to discharge a quantity of a tracer in the feed dispensing mechanism, sensing a concentration of the discharged tracer in the gas collection pipe, and, with the data analyzing station, quantifying a capture rate for breath emitted by the ruminant during the second measuring step and applying the capture rate to the determined mass fluxes to generate capture rate-adjusted fluxes for the ruminant.

5. The method of claim 3, wherein the gas collection pipe includes a flow distributor providing a mixing of the air flow drawn into the gas collection pipe across the gas collection pipe, whereby mixing of the air flow is provided across a flow path with minimal mixing along the flow path in the gas collection pipe.

6. The method of claim 3, wherein an inlet plenum to the gas collection pipe inlet is positioned in feed dispensing mechanism to extend upward from at least two sides of the food tray, the inlet plenum including a plurality of inlet holes for directing ruminant breath and air into the gas collection pipe inlet.

7. The method of claim 6, further comprising differentiating emissions of methane and carbon dioxide by the ruminant during eructations from emissions of methane and carbon dioxide in tidal air of the ruminant.

8. The method of claim 1, wherein the total air flow is at least about 8 times greater than breath emitted from the ruminant.

9. The method of claim 1, wherein the sensing of the ruminant comprises operating an infrared or ultrasonic head sensor to determine a position of the ruminant's head relative to the food tray including a distance of a portion of the ruminant's head to the head sensor.

10. An apparatus for monitoring methane emissions from a ruminant, comprising:
means to entice a ruminant to voluntarily place its nose and mouth in a position that facilitates measurement of exhaled breath;
a gas collection manifold with an inlet near the nose and mouth position in the ruminant enticement means, the gas collection manifold drawing a flow of air into the inlet;
a methane monitoring device monitoring methane in the gas collection manifold including methane concentrations in exhaled breath of the ruminant and in air in the absence of the ruminant; and
a data analyzing station processing the monitored methane concentrations to determine methane emitted by the ruminant from rumen metabolism.

11. The apparatus of claim 10, further comprising a container dispensing a supplement into the ruminant enticement means for consumption by the ruminant, wherein the container is operable to dispense the supplement in response to the determined methane emitted during rumen metabolism and wherein the supplement is adapted to reduce emission of methane in the exhaled breath of the ruminant.

12. The apparatus of claim 10, wherein the ruminant enticement means comprises a feeder shell with an opening for receiving the nose and mount of the ruminant, the feeder shell including a wedge-shaped body and being pivotal in wind such that the opening faces away from a direction of the wind to limit mixing in the feeder shell.

13. The apparatus of claim 10, wherein the ruminant enticement means includes an animal identifier for identifying the ruminant and a light and sound assembly for selectively emitting light and sound when the identified ruminant is eligible for monitoring or feeding via the apparatus.

14. The apparatus of claim 10, wherein the determined methane emitted by the ruminant is a measure of a flux of methane in the exhaled breath, the measured flux being determined based on total flow in the gas collection manifold.

15. The apparatus of claim 14, further including an airflow sensor measuring the total flow and a tracer release mechanism for selectively discharging a quantity of a trace gas, the data analyzing station further operating to determine a capture rate for the exhaled breath via the inlet based on a monitoring of the trace gas and the measured total flow.

16. The apparatus of claim 10, wherein the data analyzing station further initiates a report on health, dry matter intake, or breeding status for the ruminant based on a comparison of the determined methane to a threshold methane value.

17. A method for monitoring and controlling methane production by a ruminant, comprising:
with a proximity sensor, determining a ruminant has positioned its nose and mouth into a hood of a feeding station;
while the ruminant accesses the hood, measuring a level of methane and a level of carbon dioxide in air flow and concurrently measuring a level of a tracer in the air flow;
measuring the air flow to determine a total air flow in a collection pipe;
with a data analyzing processor, processing the measured level of the tracer to determine a capture rate of breath of the ruminant in the collection pipe; and
with the data analyzing processor, determining mass fluxes of methane and carbon dioxide for the ruminant.

18. The method of claim 17, further comprising, with a processing module run by a processor, modifying a prescribed ration stored in memory to include a differing type or amount of one or more dietary supplements in the prescribed ration of nutritional supplement and feed, wherein the modified prescribed ration is used when operating a supplement and feed dispenser supplying the feeder for the ruminant, whereby methane production by the ruminant is controlled.

19. The method of claim 17, further comprising, with the data analyzing processor, determining a food supply for the ruminant has a quality below a threshold value and communicating an alert reporting a change in food supply based on the quality to a user system.

20. The method of claim 17, wherein the feeding station includes a fan drawing the air flow into the collection pipe and wherein the hood includes an inlet plenum with a plurality of holes positioned about a periphery of a food tray, the proximity sensor positioned in the hood to detect when the ruminant has positioned its nose or mouth proximate to the food tray.

21. A method for monitoring and controlling methane production by a ruminant, comprising:
   when a ruminant accesses a feeder dispenser, reading data from a tag on the ruminant identifying the ruminant;
   accessing a methane production monitoring database in memory with the identifying data to determine a feed mix associated with the ruminant;
   operating a dispenser to dispense the feed mix into the feed dispenser;
   while the ruminant accesses the feed dispenser to feed, measuring a level of methane and a level of carbon dioxide in breath of the ruminant;
   with a processing module run by a processor, determining a metabolic efficiency of the ruminant and modifying a nutritional supplement in the feed mix based on the metabolic efficiency to reduce methane production by the ruminant; and
   generating a report in a user interface of a user system that includes the metabolic efficiency, an identifier for the ruminant, and at least one other ruminant management parameter.

22. The method of claim 21, wherein the other ruminant management parameter includes caloric intake or dry matter intake.

23. The method of claim 21, further including measuring a quantity of a tracer gas during the measuring of the methane and carbon dioxide and determining a capture rate for the ruminant breath based on the measured tracer gas and total airflow, wherein the metabolic efficiency comprises a mass flux of methane determined based on the capture rate and the total airflow.

24. The method of claim 23, wherein the tracer gas comprises propane.

25. The method of claim 21, further comprising tagging the ruminant when the metabolic efficiency is determined to be below a predetermined threshold limit.

* * * * *